United States Patent
Gil et al.

(10) Patent No.: US 11,617,778 B2
(45) Date of Patent: Apr. 4, 2023

(54) IONIC SELF-ASSEMBLING PEPTIDES

(71) Applicant: 3-D Matrix, Ltd., Tokyo (JP)

(72) Inventors: Eun Seok Gil, Acton, MA (US); Elton Aleksi, West Roxbury, MA (US); Naoki Yamamoto, Yamanashi Prefecture (JP)

(73) Assignee: 3-D Matrix, Ltd., Tokyo (JP)

( * ) Notice: Subject to any disclaimer, the term of this patent is extended or adjusted under 35 U.S.C. 154(b) by 0 days.

(21) Appl. No.: 16/503,039

(22) Filed: Jul. 3, 2019

(65) Prior Publication Data

US 2020/0009214 A1    Jan. 9, 2020

Related U.S. Application Data

(60) Provisional application No. 62/693,877, filed on Jul. 3, 2018.

(51) Int. Cl.
| | | |
|---|---|---|
| *A61K 38/10* | (2006.01) | |
| *A61P 19/04* | (2006.01) | |
| *A61K 9/06* | (2006.01) | |
| *A61K 9/08* | (2006.01) | |
| *A61K 38/39* | (2006.01) | |
| *A61K 47/02* | (2006.01) | |
| *A61K 45/06* | (2006.01) | |

(52) U.S. Cl.
CPC ................ *A61K 38/10* (2013.01); *A61K 9/06* (2013.01); *A61K 9/08* (2013.01); *A61K 38/39* (2013.01); *A61K 47/02* (2013.01); *A61P 19/04* (2018.01); *A61K 45/06* (2013.01)

(58) Field of Classification Search
CPC .................................................. A61K 38/10
See application file for complete search history.

(56) References Cited

U.S. PATENT DOCUMENTS

2018/0340188 A1\* 11/2018 Gebeyehu .......... C07K 5/06095
2018/0360904 A1  12/2018 Nagano et al.

FOREIGN PATENT DOCUMENTS

| EP | 2314325 A2 | 4/2011 |
| WO | 2011131671 A1 | 10/2011 |
| WO | 2017210416 A1 | 12/2017 |
| WO | 2020008377 A2 | 1/2020 |

OTHER PUBLICATIONS

Zhang et al. Rational Design of Charged Peptides that Self-Assemble into Robust Nanofibers as Immune-Functional Scaffolds. Acta Biomater. Epub Mar. 30, 2017; 551;183-193 (Year: 2017).\*
Batra et al. Self-assembling peptide discovery: overcoming human bias with machine learning. Nature Portfolio, 2021; DOI: https://doi.org/10.21203/rs.3.rs-505801/v1 (Year: 2021).\*
Bowie et al. Deciphering the Message in Protein Sequences: Tolerance to Amino Acid Substitutions. Science, 1990, 247:1306-1310 (Year: 1990).\*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine ResidueJ. Cell Biol. 111:2129-2138, 1990 (Year: 1990).\*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).\*
Bork. Powers and Pitfalls in Sequence Analysis: The 70% Hurdle. Genome Research, 2000, 10:398-400 (Year: 2000).\*
Greenspan et al. 1999. Defining epitopes: It's not as easy as it seems; Nature Biotechnology, 17:936-937 (Year: 1999).\*
Zhang Hangyu, et al: "Rational design of charged peptides that self-assemble into robust nanofibers as immune-functional scaffolds", Acta Biomaterialia, Elsevier, Amsterdam, NL. vol. 55, Mar. 30, 2017 (Mar. 30, 2017), pp. 183-193, XP085034271, ISSN: 1742-7061, DOI: 10.1016/J.ACTBIO.2017.03.041.
Yuqiao Sun et al: "Self-assembly behaviors of molecular designer functional RADA 16-I peptides: influence of motifs, pH, and assembly time", Biomedical Materials, Institute of Physics Publishing, Bristol, GB, vol. 12, No. 1, Dec. 9, 2016 (Dec. 9, 2016), p. 15007, XP020312994, ISSN: 1748-605X, DOI: 10.1088/1748-605X/12/1/015007 [retrieved on Dec. 9, 2016].
International Search Report and Written Opinion corresponding to PCT/IB2019/055661, dated Feb. 27, 2020, 9 pages.
International Preliminary Report on Patentability, PCT/IB2019/055661, dated Jan. 1, 2021, 10 pages.

\* cited by examiner

*Primary Examiner* — Vanessa L. Ford
*Assistant Examiner* — Sandra Dillahunt
(74) *Attorney, Agent, or Firm* — IP Supra, PLLC; Constantine Linnik; Beth L. Smiley

(57) ABSTRACT

Provided herein are ionic self-assembling peptides, pharmaceutical compositions comprising the peptides, and methods of using and making the same.

32 Claims, 17 Drawing Sheets
Specification includes a Sequence Listing.

FIGS. 20A-C
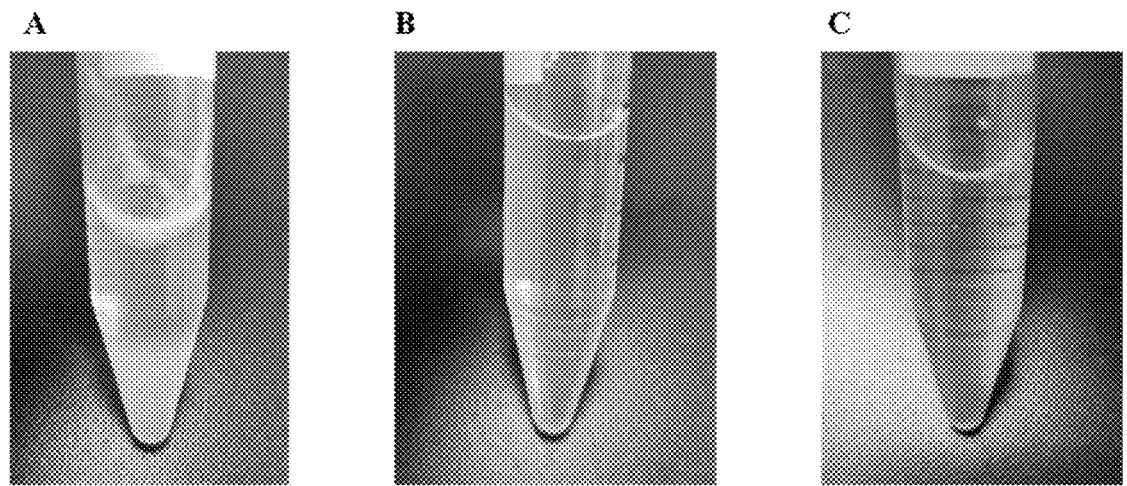
FIGS. 21A-B
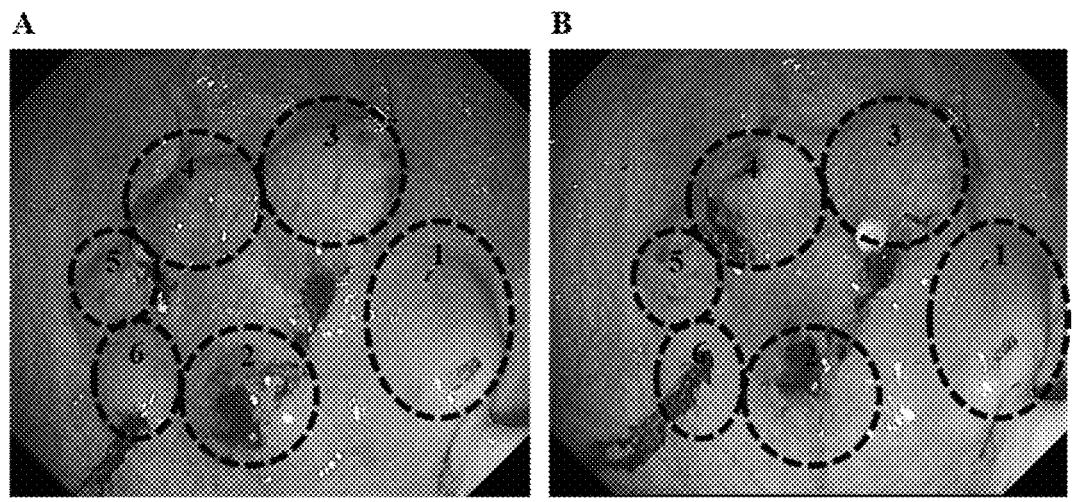

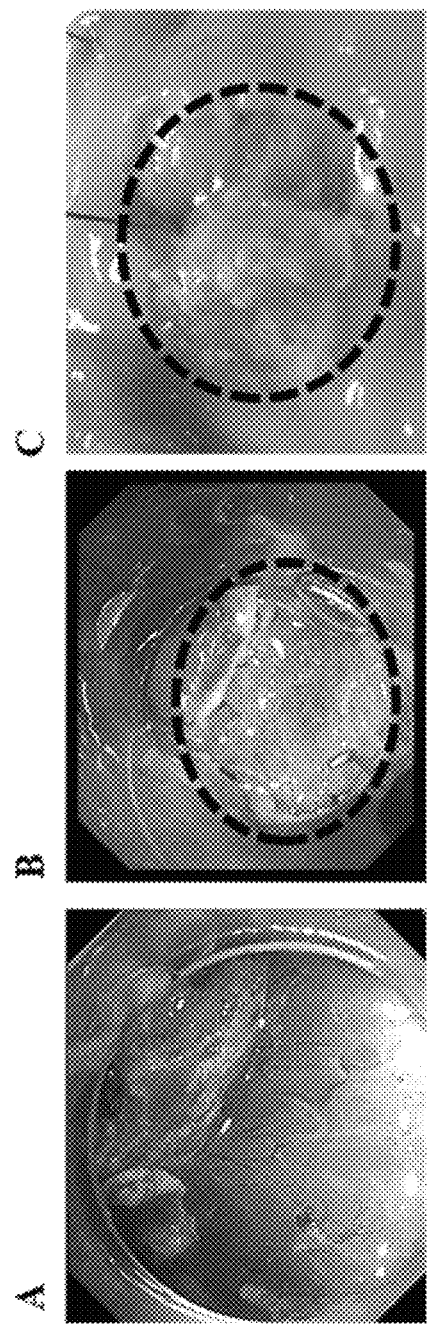
FIGS. 22A-C

IONIC SELF-ASSEMBLING PEPTIDES

CLAIM OF PRIORITY

This application claims the benefit of U.S. Provisional Application Ser. No. 62/693,877, filed on Jul. 3, 2018. The entire contents of the foregoing are incorporated herein by reference.

SEQUENCE LISTING

The instant application contains a Sequence Listing which has been submitted electronically in ASCII format and is hereby incorporated by reference in its entirety. Said ASCII copy, created on Jul. 1, 2019, is named 46406-0029001 SEQ.txt and is 22,093 bytes in size.

FIELD OF THE INVENTION

The disclosure generally relates to self-assembling peptides, pharmaceutical compositions comprising the self-assembling peptides, and methods of using the same.

BACKGROUND

Self-assembling peptides have been developed for various purposes, including scaffolding for tissue engineering and regenerative medicine, drug delivery, three-dimensional tissue culture, and hemostasis. Examples of such self-assembling peptides include β-sheet peptides (1) with alternating positively and negatively charges and hydrophobic residues (e.g., RADA16 (SEQ ID NO: 91), IEIK13 (SEQ ID NO: 92), and KLDL12 (SEQ ID NO: 93)), (2) with alternating sequences of non-ionic, polar residues and hydrophobic residues, and (3) with repeating non-ionic, polar residues. However, such self-assembling peptides have practical limitations. For example, pharmaceutical compositions including these self assembling peptides with alternating positively and negatively charges and hydrophobic residues (e.g., RADA16 (SEQ ID NO: 91)) must be formulated at acidic pH in order to solubilize the peptides, which can cause cell and/or tissue damage upon administration to a subject. Thus, there remains a need for improved self-assembling peptides that can be used for therapeutic applications.

SUMMARY OF THE INVENTION

The present disclosure is based, at least in part, on the development of ionic self-assembling peptides having specific combinations of ionic polar amino acids, hydrophobic amino acids, and non-ionic polar amino acids. Previously described self-assembling peptides typically include equivalent amounts of amino acid residues having net-negative charge and net-positive charge at neutral pH. These peptides are formulated at acidic or basic pH to charge the peptides such that the peptides remained in solution, and such that the compositions comprising the peptides were flowable and injectable. If formulated at neutral pH, phase separation and precipitation of the peptides was observed. For example, RADA16 (SEQ ID NO: 91) has four positive charges and four negative charges at neutral pH. As shown in FIG. 20A, when formulated at pH 7.5 RADA 16 (SEQ ID NO: 91) precipitates.

In contrast, the inclusion of ionic polar amino acids in the self-assembling peptides provided herein results in peptides having non-zero net charge at neutral pH, thereby allowing for the peptides to be formulated at neutral pH. Advantageously, the ionic self-assembling peptides provided herein can be formulated at neutral pH and remain soluble and stable in solution. Without wishing to be bound by any particular theory, pharmaceutical compositions comprising the ionic self-assembling peptides described herein may be formulated at neutral pH and administered to a subject without inducing tissue damage that may be associated with pharmaceutical compositions having acidic or basic pH. Moreover, the ionic self-assembling peptides can be used to make improved hydrogels having advantageous physical characteristics under physiological conditions. For example, aqueous solutions of the self-assembling peptides may be produced which remain stable, and are flowable and injectable under physiological conditions. Upon gelation, the self-assembling peptides may form hydrogels having shear-thinning, thixotropic, and theological properties that are useful in clinical, industrial, and/or research applications.

In some aspects, the disclosure provides self-assembling peptides and pharmaceutical compositions comprising the self-self assembling peptides, wherein the self-assembling peptide comprises or consist of an amino acid sequence as set forth in: $[(X)i(Y)j(Z)k(Y)l]m(X)n$ (Formula I), $[(Y)i(X)j(Y)k(Z)l]m(Y)n$ (Formula II), $[(Z)i(Y)j(X)k(Y)l]m(Z)n$ (Formula III), or $[(Y)i(Z)j(Y)k(X)l]m(Y)n$ (Formula IV), wherein each (X) is independently an ionic, polar amino acid, wherein each (Y) is independently a hydrophobic amino acid, wherein each (Z) is independently a non-ionic, polar amino acid, wherein each i, j, k, and I is independently an integer≥1, wherein m is an integer≥2, and wherein n=0 or an integer≥1. In some embodiments, at least one of i, i, k, and l is independently an integer of 1. In some embodiments, at least one of i, j, k, and l is independently an integer of 2. In some embodiments, each of i, j, k, and l is 1. In some embodiments, m is independently an integer of 2, 3, or 4.

In some embodiments, the self-assembling peptide comprises or consists of an amino acid sequence as set forth in Formula I. In some embodiments, the self-assembling peptide comprises or consists of an amino acid sequence as set forth in Formula II. In some embodiments, the self-assembling peptide comprises or consists of an amino acids sequence as set forth in Formula III. In some embodiments, the self-assembling peptide comprises or consists of an amino acid sequence as set forth in Formula IV.

In some embodiments, each (X) is a basic amino acid (e.g., arginine, lysine, histidine, or ornithine). In some embodiments, each (X) is an acidic amino acid (e.g., aspartic acid or glutamic acid).

In some embodiments, each (Y) is either alanine, valine, leucine, isoleucine, methionine, phenylalanine, tryptophan, or glycine.

In some embodiments, each (Z) is either serine, threonine, tyrosine, cysteine, glutamine, asparagine, or methionine.

In some embodiments, the self-assembling peptide comprises or consists of an amino acid sequence as set forth in SEQ ID NOs: 1-20 and 94-96.

In some embodiments, the self-assembling peptide comprises an N-terminal functional group, a C-terminal functional group, or both. In some embodiments, the N-terminal functional group is either an acetyl, a formyl, pyroglutamyl (pGlu), biotin, polyethylene glycol (PEG), urea, alkylamine, a carbamate, a sulfonamide, dansyl, 2,4-dintrophenyl, fluorescein, 7-methoxycoumarin acetic acid, 9-fluorenylmethyl-oxycarbonyl, palmitic acid, succinyl, chloroacetyl, maleimide, benzyloxycarbonyl, bromoacetyl, nitrilotriacetyl, tertbutoxycarbonyl, 4-hydroxyphenylpropionic acid, allyloxycarbonyl, butyric acid, a fatty acid, or trityl. In some embodiments, the C-terminal functional group is either an amido, an N-alkyl amide, an aldehyde, an ester, an alcohol, para-nitroanilide (pNA), 7-amino-4-methylcoumarin (Amc), a hydrazide, hydroxamic acid, chloromethylketone, p-nitroaniline, para-nitrophenol, hydroxysucinimide ester, fluoromethylketone, cysteamide, 9-fluorenemethyl (Fm) ester, allyl ester, 2,4-dimethoxybenzyl ester, 2-phenylisopropyl ester, p-nitrobenzyl ester, and 2-chlorotrityl ester. In some embodiments, the self-assembling peptide comprises or consists of an amino acid sequence as set forth in SEQ ID NOs: 21-40 and 97-99.

In some embodiments, the self-assembling peptide comprises at least one (e.g., one, two, three, four, or more) biologically active peptide motif. In some embodiments, the at least one biologically active peptide motif is present at the N-terminal end of the self-assembling peptide. In some embodiments, the at least one biologically-active peptide motif is present at the C-terminal end of the self-assembling peptide. In some embodiments, the at least one biologically-active peptide motif is derived from laminin-1, collagen TV, fibronectin, elastin, bone marrow homing peptide 1, bone marrow homing peptide 2, or myelopeptide. In some embodiments, the at least one biologically-active peptide motif comprises or consists of an amino acid sequence as set forth in any one of SEQ ID NOs: 1-70. In some embodiments, the self-assembling peptide comprises or consists of an amino acid sequence as set forth in SEQ ID NOs: 71-90.

In some embodiments, the pharmaceutical composition comprises a tonicity agent. In some embodiments, the tonicity agent comprises one or more salts selected from the group consisting of NaCl, KCl, $MgCl_2$, $CaCl_2$, $NH_4Cl$, $Na_2HPO_4$, $KH_2PO_4$, and $CaSO_4$. In some embodiments, the tonicity agent further comprises one or more sugars selected from the group consisting of dextrose, mannitol, glycerin, sucrose, and trehalose. In some embodiments (e.g., when the tonicity agent is one or more salts), the tonicity agent is present at a concentration of about 0.01 M to about 0.3 M. In some embodiments (e.g., when the tonicity agent is one or more salts), the tonicity agent is present at a concentration of about 0.15 M. In some embodiments (e.g., when the tonicity agent is one or more sugars), the tonicity agent is present at a concentration of about 0.1 to 10% (w/v). In some embodiments e.g., when the tonicity agent is one or more sugars), the tonicity agent is present at a concentration of about 10% (w/v). In some embodiments, the tonicity agent increases rheological properties of the composition or hydrogel peptide comprising the self-assembling peptides described herein.

In some embodiments, the pharmaceutical composition has a pH of from about 6 to about 8. In some embodiments, the pharmaceutical composition has a pH of from about 7 to about 7.5. In some embodiments, the net charge of the self-assembling peptide in the pharmaceutical composition is greater than or equal to +1 or less than or equal to −1. In some embodiments, the net charge of the self-assembling peptide in the pharmaceutical composition is from about +1 to about +6 (e.g., +1, +2, +3, +4, +5, or +6). In some embodiments, the net charge of the self-assembling peptide in the pharmaceutical composition is from about −1 to about −6 (e.g., −1, −2, −3, −4, −5, or −6).

In some embodiments, the concentration of the self-assembling peptide is the pharmaceutical composition is from about 0.01% (w/v) to about 10% (w/v). In some embodiments, the concentration of the self-assembling peptide is the pharmaceutical composition is from about 0.1% (w/v) to about 5% (w/v). In some embodiments, the concentration of the self-assembling peptide is the pharmaceutical composition is from about 0.5% (w/v) to about 1.5% (w/v). In some embodiments, the concentration of the self-assembling peptide is the pharmaceutical composition is about 1% (w/v).

In some embodiments, the pharmaceutical composition comprises an isolated cell (e.g., a stem cell). In some embodiments, the isolated cell is a mammalian cell. In some embodiments, the mammalian cell is an immune cell, a stem cell, chondrocyte progenitor cells, pancreatic progenitor cells, myoblasts, fibroblasts, keratinocytes, neuronal cells, glial cells, astrocytes, pre-adipocytes, adipocytes, vascular endothelial cells, endothelial progenitor cells, mesenchymal cells, neural stem cells, immune cells, (e.g., B-cells and I-cells), smooth muscle progenitor cells, cardiac myocytes, fetal dermal fibroblasts, epidermal keratinocytes, myoblasts, and capillary endothelial cells.

In some embodiments, the pharmaceutical composition comprises at least one (e.g., one, two, three, four, five, or more) bioactive agent. In some embodiments, the bioactive agent is a hormone, a growth factor, insulin, an enzyme, an siRNA, an shRNA, an anti sense-RNA, an anti-sense-DNA, an mRNA, an antibiotic, an antibody, or an anti-inflammatory agent.

In some embodiments, the pharmaceutical composition is an aqueous solution. In some embodiments, the pharmaceutical composition is a hydrogel.

In some embodiments, the pharmaceutical composition is a hydrogel having a storage modulus of at least about 10 Pascal (Pa) (e.g., about 25 Pa, about 50 Pa, about 100 Pa, about 150 Pa, about 250 Pa, about 500 Pa, about 750 Pa, about 1000 Pa, or more).

In another aspect, the disclosure provides articles of manufacture comprising the self-assembling peptides or the pharmaceutical composition described herein. In some embodiments, the article is a syringe, a vial, an auto-injector, tubing, or a catheter.

In another aspect, the disclosure provides methods of treating a subject in need thereof, comprising administering an effective amount of a self-assembling peptide or of a pharmaceutical composition described herein to the subject.

In yet another aspect, the disclosure provides methods of promoting tissue repair or regeneration in a subject in need thereof, comprising contacting a tissue of the subject with a self-assembling peptide or a pharmaceutical composition described herein, thereby promoting tissue repair or regeneration of the tissue. In some embodiments, the tissue is skin, bone, cartilage, neural tissue, ligament, tendon, vascular tissue, or muscle. In some embodiments, the tissue is optic tissue. In some embodiments, the tissue is cardiac tissue. In some embodiments, the subject has a congenital disease or disorder resulting in a need for the tissue repair or regeneration. In some embodiments, the subject has suffered an injury (e.g., surgery, trauma, stroke, tumor, or a disease or disorder) resulting in a need for the tissue repair or regeneration.

In another aspect, the disclosure provides methods of promoting wound healing in a subject in need thereof, comprising contacting a wound of the subject with (or, alternatively, administering to a subject's wound) an effective amount of a self-assembling peptide or a pharmaceutical composition described herein, thereby promoting wound healing and/or antimicrobial activity. In some embodiments, the wound comprises or consists of an abrasion, a burn, a chap, a detrition, a cut, an ulcer, a laceration, an incision, or a scratch.

In another aspect, the disclosure provides methods of stopping or preventing (or, alternatively, reducing) bleeding at a site within a subject, comprising contacting the site with (or, alternatively, administering to a subject's wound) a self-assembling peptide or a pharmaceutical composition described herein, thereby creating a physical barrier thereby stopping or preventing (or reducing) bleeding at the site within the subject.

In another aspect, the disclosure provides methods of excising a lesion from a site in the gastrointestinal tract of a subject, comprising contacting submucosa below the lesion with (or, alternatively, administering to the submucosa below the lesion) a self-assembling peptide or a pharmaceutical composition described herein, in an amount sufficient to lift the lesion; and excising the lesion from the site in the gastrointestinal tract of the subject. In some embodiments, the lesion comprises a polyp, an ulcer, or a tumor. In some embodiments, the lesion is present in a region of the gastrointestinal tract of the subject selected from a mouth, a throat, an esophagus, a stomach, a small intestine, a large intestine, a colon and a rectum.

In yet another aspect, the disclosure provides methods of culturing a cell that include contacting the cell with a pharmaceutical composition described herein.

In another aspect, provided herein is a method of treating a pulmonary bulla in a subject, comprising:
 introducing a delivery device to a target area of the pulmonary bulla of the subject; positioning an end of the delivery device in the target area in which a treatment of the pulmonary bulla is desired;
 administering, through the delivery device, a self-assembling peptide or a pharmaceutical composition described herein in an effective amount and in an effective concentration to the target area to form a barrier under physiological conditions of the target area to treat the pulmonary bulla;
 removing the delivery device from the target area; and
 collapsing the pulmonary bulla prior or subsequent to administering the solution.

In another aspect, provided herein is a method for mitigating adhesion to a biological tissue, the method comprising administering to the biological tissue an effective amount of a self-assembling peptide or a pharmaceutical composition described herein, to thereby mitigate adhesion to the biological tissue.

In another aspect, provided herein is a method of filling a bone void in a subject, comprising
 introducing a delivery device to a bone of a subject;
 positioning an end of the delivery device proximate a void in the bone where promotion of bone growth is desired;
 administering a self-assembling peptide or a pharmaceutical composition described herein in a concentration sufficient to form a hydrogel scaffold under physiological conditions through the delivery device; and
 removing the delivery device.

In another aspect, provided herein is a method of treating dry eye in a subject, comprising administering to an eye of the subject an effective amount of a self-assembling peptide or a pharmaceutical composition described herein.

The present invention further provides self-assembling peptides comprising or consisting of an amino acid sequence as set forth in: [(X)i(Y)j(Z)k(Y)l]m(X)n (Formula I), [(Y)i(X)j(Y)k(Z)l]m(Y)n (Formula II), [(Z)i(Y)j(X)k(Y)l]m(Z)n (Formula III), or [(Y)i(Z)j(Y)k(X)l]m(Y)n (Formula IV), for use in any of the methods described herein.

Other features and advantages of the invention will be apparent from the following detailed description and figures, and from the claims.

BRIEF DESCRIPTION OF THE DRAWINGS

FIG. 6 shows shear-thinning properties of an aqueous pharmaceutical compositions including 1% (w/v) KLNL12 (SEQ ID NO: 21) at pH 7.5, as reflected by changing viscosity in response to various shear rates.

FIG. 7 shows shear-thinning properties of an aqueous pharmaceutical compositions including 1% (w/v) IQIK13 (SEQ ID NO: 28) at pH 7.5, as reflected by changing viscosity in response to various shear rates.

FIG. 8 shows shear-thinning properties of an aqueous pharmaceutical compositions including 1% (w/v) NLEL12 (SEQ ID NO: 33) at pH 7.5, as reflected by changing viscosity in response to various shear rates.

FIG. 9 shows shear-thinning properties of an aqueous pharmaceutical compositions including 1% (w/v) KLNL12 (SEQ ID NO: 21) containing 0.9% NaCl at pH 7.5, as reflected by changing viscosity in response to various shear rates.

FIG. 10 shows shear-thinning properties of an aqueous pharmaceutical compositions including 1% NLEL12 (SEQ ID NO: 33) containing 0.9% NaCl at pH 7.5, as reflected by changing viscosity in response to various shear rates.

FIG. 11 shows thixotropic properties of an aqueous pharmaceutical compositions including 1% (w/v) KLNL12 (SEQ ID NO: 21) containing 0.9% NaCl at pH 7.5, as reflected by changes in mechanical strength after shear stress is removed.

FIG. 12 shows thixotropic properties of an aqueous pharmaceutical compositions including 1% NLEL12 (SEQ ID NO: 33) containing 0.9% NaCl at pH 7.5, as reflected by changes in mechanical strength after shear stress is removed.

FIG. 13 shows changes in rheological properties of an aqueous pharmaceutical compositions including 1% (w/v) KLNL12 (SEQ ID NO: 21) at pH 7.5, as reflected by increased mechanical strength after exposure to DMEM.

FIG. 14 shows changes in rheological properties of an aqueous pharmaceutical compositions including 1% (w/v) KIQI13 (SEQ ID NO: 29) at pH 7.5, as reflected by increased mechanical strength after exposure to DMEM.

FIG. 15 shows changes in rheological properties an aqueous pharmaceutical compositions including 1% (w/v)

NLEL12 (SEQ ID NO: 33) at pH 7.5, as reflected by increased mechanical strength after exposure to DMEM.

Figure 16:
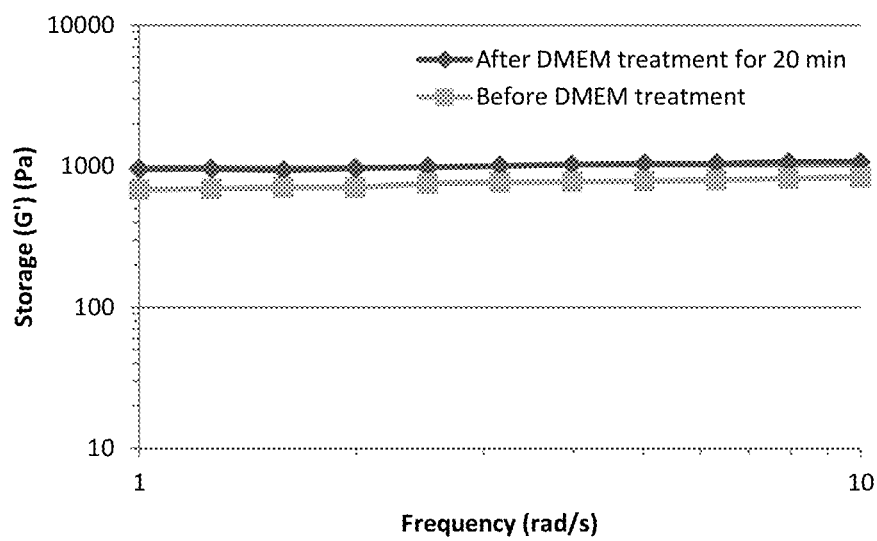
Figure 17:
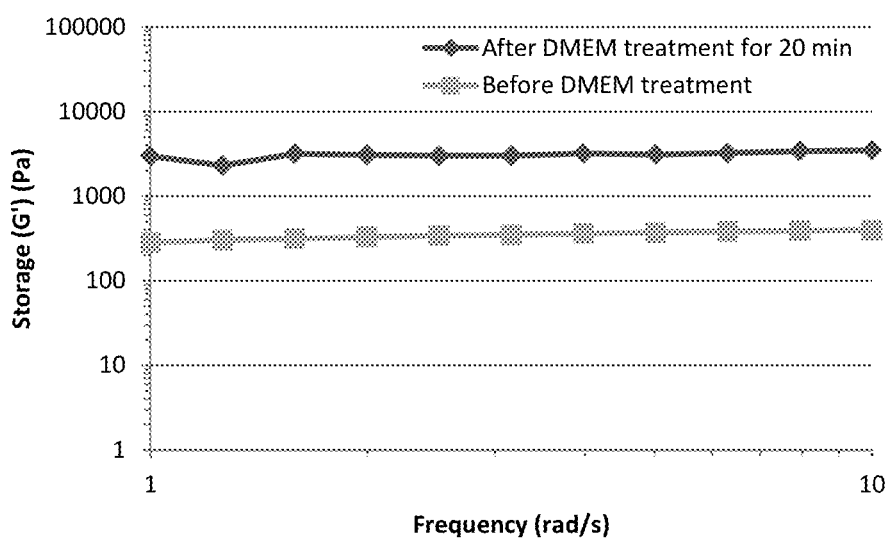
Figure 18:
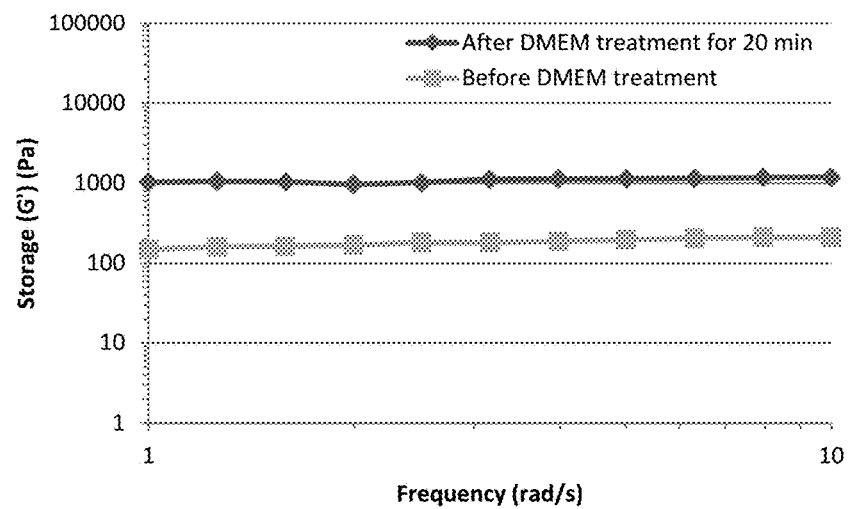

FIGS. 16-18 show changes in rheological properties of exemplary aqueous pharmaceutical compositions including the self-assembling peptides KLNL12 (SEQ ID NO: 21), KIQI13 (SEQ ID NO: 29), or NLEL12 (SEQ ID NO: 33), in response to exposure to DMEM.

FIG. 16 shows changes in rheological properties of an aqueous pharmaceutical compositions including 1% (w/v) KLNL12 (SEQ ID NO: 21) containing 0.9% NaCl at pH 7.5, as reflected by increased mechanical strength after exposure to DMEM.

FIG. 17 shows changes in rheological properties of an aqueous pharmaceutical compositions including 1% (w/v) KIQI13 (SEQ ID NO: 29) containing 0.9% NaCl at pH 7.5, as reflected by increased mechanical strength after exposure to DMEM.

FIG. 18 shows changes in rheological properties of an aqueous pharmaceutical compositions including 1% NLEL12 (SEQ ID NO: 33) containing 0.9% NaCl at pH 7.5, as reflected by increased mechanical strength after exposure to DMEM.

Figure 19:
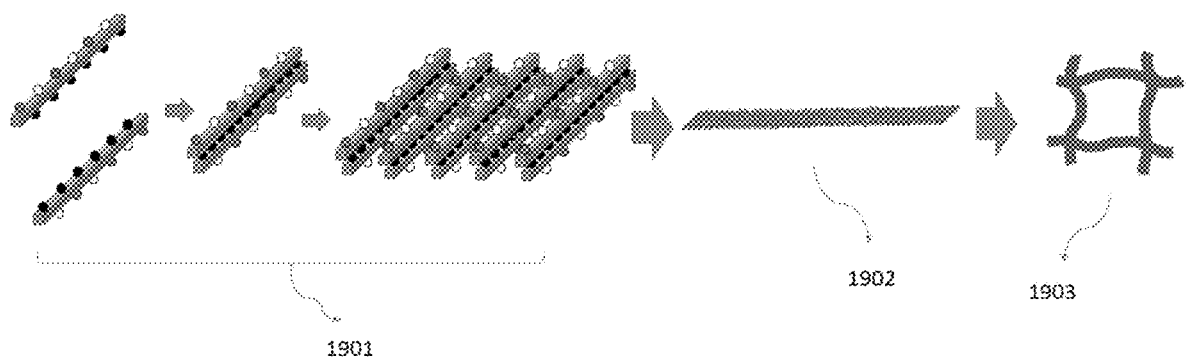
Figures 23A, 23B, 23C, 23D:
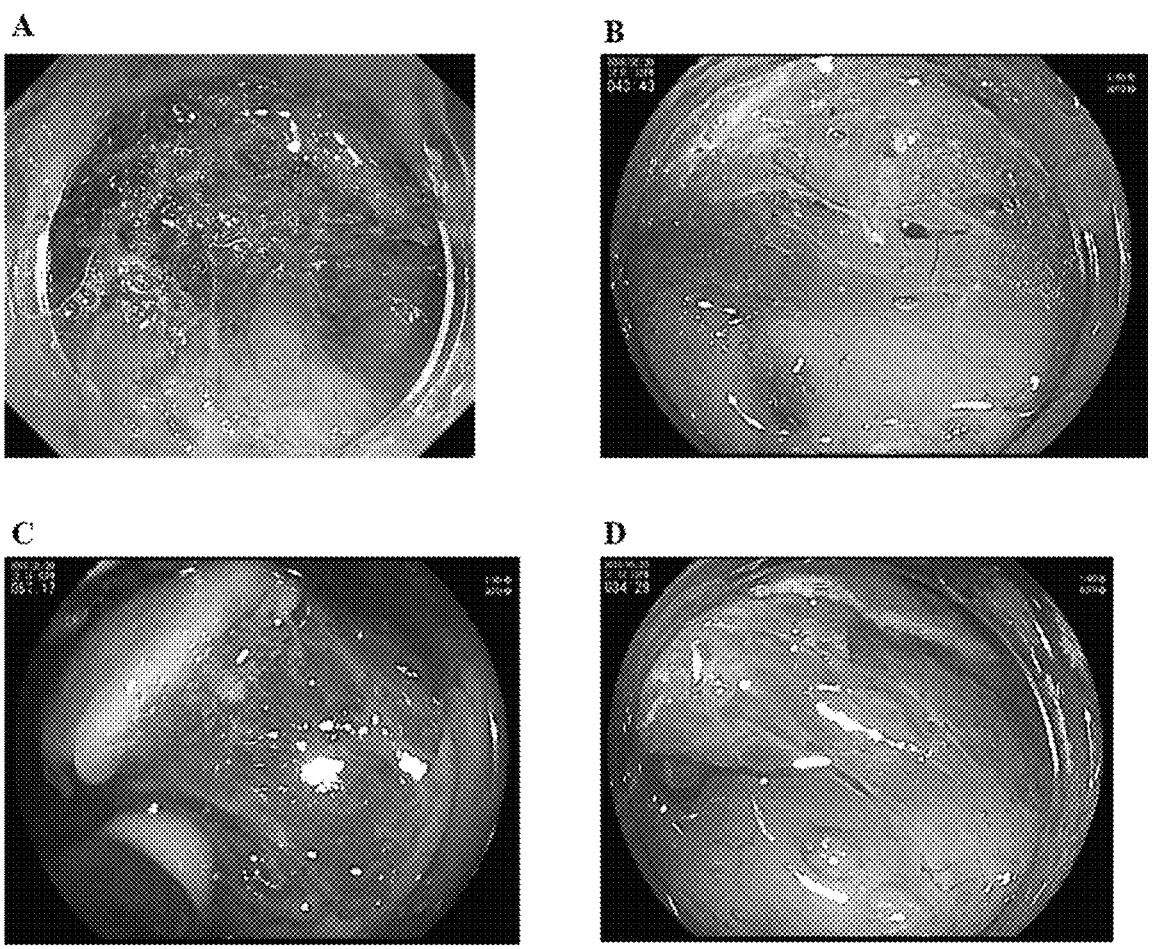

FIG. 19 is a schematic representation of macromolecular structures that can be formed by the self-assembling peptide of the invention.

FIGS. 20A-20C below are photographs showing the appearance of aqueous pharmaceutical compositions including the specified self-assembling peptide at pH 7.5. FIG. 20A is a photograph showing the appearance of an aqueous pharmaceutical composition including RADA16 (SEQ ID NO: 91), pH 7.5.

FIG. 20B is a photograph showing the appearance of an aqueous pharmaceutical composition including KLNL12 (SEQ ID NO: 21), pH 7.5.

FIG. 20C is a photograph showing the appearance of an aqueous pharmaceutical composition including NLEL12 (SEQ ID NO: 33), pH 7.5.

FIGS. 21A and 21B show the appearance of pig stomach submucosa following injections of the specified pharmaceutical compositions after 0-5 minutes (FIG. 21A) and after 15-20 minutes (FIG. 21B). Injection sites are indicated with dotted black ovals: (1) 2 mL of 0.1% (w/v) KLNL12 (SEQ ID NO: 21), 0.9% (w/v) NaCl pH 7.5; (2) 2 mL of 0.1% (w/v) NLKL12 (SEQ ID NO: 23), 0.9% (w/v) NaCl pH 7.5; (3) 2 mL of 0.1% (w/v) KIQI13 (SEQ ID NO: 29), 0.9% (w/v) NaCl pH 7.5; (4) 2 mL of 0.2% (w/v) RADA16 (SEQ ID NO: 91) pH 2.5; (5) 2 mL of MucoUp®; (6) 2 mL of saline pH 7.5.

FIGS. 22A-22C show the appearance of dissected pig stomach submucosa following injections of either 2 mL saline at pH 7.5 (FIG. 22A), or 2 mL of an aqueous pharmaceutical composition including 0.2% (w/v) RADA16 (SEQ ID NO: 91) at pH 2.5 (FIG. 22B), or 2 ml of an aqueous pharmaceutical composition including 0.2% (w/v) RADA16 (SEQ ID NO: 91), 0.9% NaCl (w/v) at pH 2.5 (FIG. 22C). Black ovals indicate areas that were white and had a cloudy undefined appearance.

FIGS. 23A, 23B, 23C, and 23D show the appearance of pig stomach submucosa following injections of 2 mL of a pharmaceutical composition including 0.1% KLNL12 (SEQ ID NO: 21), 0.9% NaCl, at pH 7.5 (FIG. 23A); 2 mL of a pharmaceutical composition including 0.2% NLEL12 (SEQ ID NO: 33), 0.9% NaCl, at pH 7.5 (FIG. 23B); 2 mL of a pharmaceutical composition including 0.2% QLEL12 (SEQ ID NO: 35), 0.9% NaCl, at pH 7.5 (FIG. 23C); or 2 mL of a pharmaceutical composition including 0.2% LELQ12 (SEQ ID NO: 36), 0.9% NaCl, at pH 7.5.

Figure 24A:
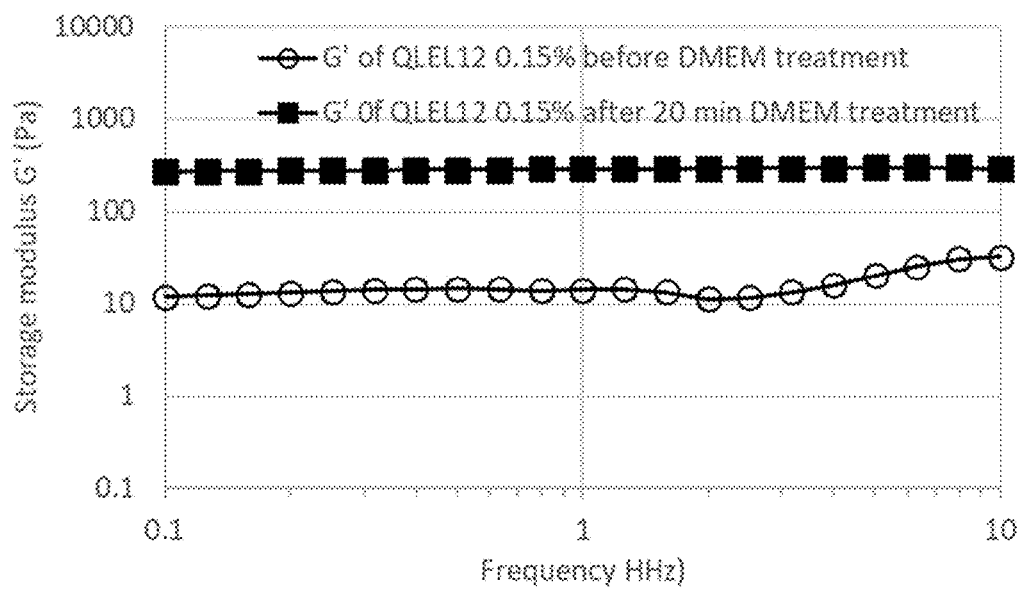

FIG. 24A shows changes in rheological properties of an aqueous pharmaceutical compositions including 0.15% (w/v) QLEL12 (SEQ ID NO: 35) with 0.9% NaCl (w/v) at pH 7.5, as reflected by increased mechanical strength after exposure to DMEM.

Figure 24B:
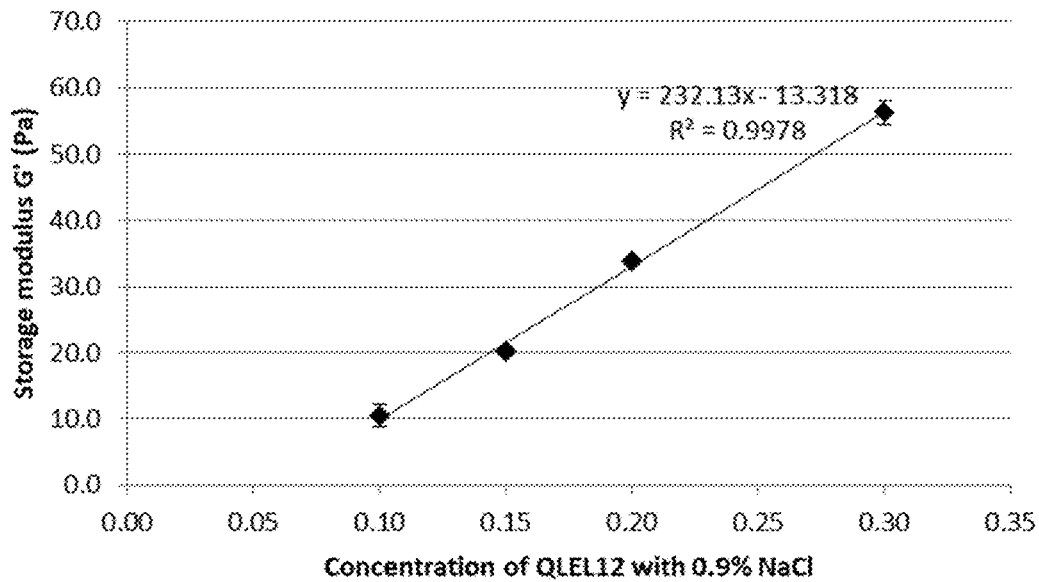

FIG. 24B shows rheological properties of an aqueous pharmaceutical compositions including QLEL12 (SEQ ID NO: 35) with 0.9% NaCl (w/v) at pH 7.5 at various concentrations between 0.1% (w/v) and 0.3% (w/v); linear regression was performed.

FIGS. 25A-25D shows elevation heights and lifting capability of the submucosal layer in the canine stomach and colon after injecting 0.5 mL of QLEL12 (SEQ ID NO: 35) with 0.9% NaCl (w/v) at pH 7.5 at various concentrations between 0.1% (w/v) and 0.3% (w/v).

These and other advantages of the present technology will be apparent when reference is made to the following description.

DETAILED DESCRIPTION

Definitions

Unless otherwise defined herein, scientific and technical terms used in this disclosure shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification.

Chemistry terms used herein are used according to conventional usage in the art, as exemplified by "The McGraw-Hill Dictionary of Chemical Terms," Parker S., Ed., McGraw-Hill, San Francisco, Calif. (1985).

All of the publications, patents and published patent disclosures referred to in this disclosure are specifically incorporated by reference herein. In case of conflict, the present specification, including its specific definitions, will control.

The term "self-assembling", as used herein, refers to the ability of certain peptides to spontaneously self-associate into higher order structures (e.g., β-sheets). For example, pharmaceutical compositions comprising self-assembling peptides in the form of a solution transition to a gel state when the self-assembling peptides self-associate. In some embodiments, the interaction between and among individual self-assembling peptides are reversible, such that the composition may reversibly transition between a gel state and a solution state. The interactions between and among individual self-assembling peptides may be non-covalent interactions including hydrogen bonds, ionic interactions, electrostatic interactions (e.g., via van der Waals forces), and hydrophobic interactions. In various embodiments, the self-assembled peptide nanostructure comprises peptides in β-sheets. The nanostructure can be a nanofiber, or a network of nanofibers. For illustrative purposes, FIG. 19 shows the assembly of self-assembling peptides into β sheets 1901. These β sheets can self-assemble into a nanofiber 1902. A plurality of nanofibers 1902 can self-assemble into a membrane network 1903. In some embodiments, the self-assembly of the peptides described herein into higher order structures is responsive to one or more environmental triggers (e.g., change in one or more of pH, temperature, ionic strength, osmolarity, osmolality, applied pressure, applied shear stress, etc.).

As used herein, the term "administering" is intended to include, but is not limited to, applying, introducing or injecting a self-assembling peptide and/or a pharmaceutical composition comprising a self-assembling peptide described herein.

As used herein, the term "amino acid residue" or "amino acid" includes natural and synthetic amino acid residues including D- and L-amino acids; alpha-, beta- and gamma-amino acids; chemically-modified amino acids; naturally-occurring non-proteogenic amino acids; rare amino acids; and chemically synthesized compounds that have properties known in the art to be characteristic of an amino acid.

As used herein, the phrases "therapeutically effective amount", "effective amount" or "effective dose" refer to an amount of pharmaceutical composition that when delivered to a subject provides a therapeutic or aesthetic benefit in the treatment, prevention, or management of a tissue, disease and/or disorder. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "hydrogel" refers to a composition comprising a three dimensional network of self-assembling peptides. The term hydrogel may be used to refer to a network of self-assembling peptides in a dry state (xerogel) or in a wet state. In a wet state, the hydrogel may include a high water content (e.g., between about 90% to about 99.9% water). Hydrogels have many desirable properties for biomedical applications. For example, hydrogels can be manufactured such that they are nontoxic and compatible with tissue. In addition, hydrogels are usually highly permeable to water, ions, and small molecules.

As used herein the term "isolated" in reference to cells refers to a cell that has been mechanically separated from the environment from which it is found in nature.

As used herein, the term "tonicity agent" refers to an agent which may be used to regulate the osmotic pressure of the pharmaceutical compositions described herein. Exemplary tonicity agents, include, but are not limited to sodium chloride, calcium chloride, potassium chloride, potassium phosphate, and sugars (e.g., dextrose and sucrose). In some embodiments, the tonicity agent is sodium chloride. The tonicity agent can increase rheological properties of a solution or composition (e.g., hydrogel) comprising the self-assembling peptides disclosed herein.

A "pharmaceutical composition," as used herein, refers to a composition comprising a self-assembling peptide and other components, such as a physiologically suitable carrier and/or excipient.

As used herein, the terms "proteins" and "peptides" are used interchangeably to refer to a polymer of amino acid residues connected to the other by peptide bonds between the alpha-amino and carboxy groups of adjacent residues. The terms "protein", and "peptide include polymers having modified amino acid residues (e.g., phosphorylated, amidated, or glycated amino acid residues) and amino acid analogs.

As used herein, the term "subject" refers to either a human or non-human animal. The term includes, but is not limited to, mammals (e.g., humans, other primates, pigs, rodents (e.g., mice and rats or hamsters), rabbits, guinea pigs, cows, horses, cats, dogs, sheep, and goats). In some embodiments, the subject is a human. In some embodiments, the subject is an adult human subject. In some embodiments, the subject is a pediatric human subject.

The term "wound" used herein refers to a trauma in a tissue of a subject (e.g., a human subject) such as an abrasion, a burn, a chap, a detrition, a cut, an ulcer, a laceration, an incision, or a scratch.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Citation or identification of any document in this application is not an admission that such document is available as prior art to the present invention.

Other features and advantages of the invention will be apparent from the following detailed description, and from the claims.

Pharmaceutical Compositions and Self-Assembling Peptides

In one aspect, the disclosure provides self-assembling peptides and pharmaceutical compositions comprising at least one self-assembling peptide described herein. The self-assembling peptides spontaneously assemble into higher order structures via intermolecular and intramolecular electrostatic interactions when present in an aqueous solution. These higher order structures include β-sheets, nanofiber structures, and three-dimensional network or mesh structures. When these higher order structures form aqueous solutions may become hydrogels having a variety of desirable properties. In addition to the self-assembling peptides, the pharmaceutical compositions may also include other additives such as tonicity agents, buffers, pharmaceutically-acceptable excipients, biomolecules, therapeutic agents, and cells.

In some embodiment, the self-assembling peptides are biodegradable. As used herein, "biodegradable" refers to materials that degrade or break down upon interaction with a physiological environment into components that can be metabolized or excreted by a subject over a period of time ranging from minutes to years (e.g., one day, two days, three days, four days, five days, six days, seven days, two weeks, three weeks, four weeks, two months, three months, six months, one year, two years, or more). In some embodiments, the self-assembling peptides may degrade via cleavage of the peptide chain, for example, via hydrolysis or enzymatic cleavage. Although the self-assembling peptides (and higher order structures (e.g., scaffolds) formed by the self-assembling peptides) may be biodegradable, these higher order structures preferably maintain their structural integrity for a period of time required for their intended use.

The self-assembling peptides provided herein comprise or consist of an amino acid sequence as set forth in $$[(X)i(Y)j(Z)k(Y)l]m(X)n \quad \text{(Formula I)},$$

$$[(Y)i(X)j(Y)k(Z)l]m(Y)n \quad \text{(Formula II)},$$

$$[(Z)i(Y)j(X)k(Y)l]m(Z)n \quad \text{(Formula III), or}$$

$$[(Y)i(Z)j(Y)k(X)l]m(Y)n \quad \text{(Formula IV)},$$

wherein each (X) is independently an ionic, polar amino acid, wherein each (Y) is independently a hydrophobic amino acid, wherein each (Z) is independently a non-ionic, polar amino acid, wherein each i, j, k, and l is independently an integer≥1, wherein m is an integer≥2, and wherein n=0 or an integer≥1. In some embodiments, each i, j, k, and l is independently an integer of 1. In some embodiments, each i, j, k, and l is independently an integer of 2. In some embodiments, each i, j, k, and l is independently an integer of 3. In some embodiments, n is 0. In some embodiments, n is an integer≥1 (e.g., 1, 2, 3, 4, 5, 6, 7, 8, 9, 10, 11, 12, or more). In some embodiments, m is an integer of 1. In some embodiments, m is an integer≥2 (e.g., 2, 3, 4, 6, 7, 8, 9, 10, 11, 12, or more). In some embodiments, m is an integer of 2, 3, or 4. In some embodiments, each (X) is the same amino acid, each (Y) is the same amino acid, and/or each (Z) is the same type of amino acid residue.

In some embodiments, the self-assembling peptide comprises or consists of an amino acid sequence as set forth in [(X)i(Y)j(Z)k(Y)l]m(X)n (Formula I), wherein each (X) is independently an ionic, polar amino acid, wherein each (Y) is independently a hydrophobic amino acid, wherein each (Z) is independently a non-ionic, polar amino acid, wherein each i, j, k, and l is independently an integer≥1, wherein m is an integer≥2, and wherein n=0 or an integer≥1. In some embodiments, each i, j, k, and l is independently an integer of 1. In some embodiments, each i, j, k, and l is independently an integer of 2. In some embodiments, each i, j, k, and l is independently an integer of 3. In some embodiments, n is 0. In some embodiments, n is an integer≥1 (e.g., 1, 2, 3, 4, 5, 6, 7, 8, 9, 10, 11, 12, or more). In some embodiments, m is an integer of 1. In some embodiments, m is an integer≥2 (e.g., 2, 3, 4, 6, 7, 8, 9, 10, 11, 12, or more). In some embodiments, m is an integer of 2, 3, or 4.

In some embodiments, the self-assembling peptide comprises or consists of an amino acid sequence as set forth in [(Y)i(X)j(Y)k(Z)l]m(Y)n (Formula II), wherein each (X) is independently an ionic, polar amino acid, wherein each (Y) is independently a hydrophobic amino acid, wherein each (Z) is independently a non-ionic, polar amino acid, wherein each i, j, k, and l is independently an integer≥1, wherein m is an integer≥2, and wherein n=0 or an integer≥1. In some embodiments, each i, j, k, and l is independently an integer of 1. In some embodiments, each i, j, k, and l is independently an integer of 2. In some embodiments, each i, j, k, and l is independently an integer of 3. In some embodiments, n is 0. In some embodiments, n is an integer≥1 (e.g., 1, 2, 3, 4, 5, 6, 7, 8, 9, 10, 11, 12, or more). In some embodiments, m is an integer of 1. In some embodiments, m is an integer≥2 (e.g., 2, 3, 4, 6, 7, 8, 9, 10, 11, 12, or more). In some embodiments, m is an integer of 2, 3, or 4.

In some embodiments, the self-assembling peptide comprises or consists of an amino acid sequence as set forth in [(Z)i(Y)j(X)k(Y)l]m(Z)n (Formula III), wherein each (X) is independently an ionic, polar amino acid, wherein each (Y) is independently a hydrophobic amino acid, wherein each (Z) is independently a non-ionic, polar amino acid, wherein each i, j, k, and l is independently an integer≥1, wherein m is an integer≥2, and wherein n=0 or an integer≥1. In some embodiments, each i, j, k, and l is independently an integer of 1. In some embodiments, each i, j, k, and l is independently an integer of 2. In some embodiments, each i, j, k, and l is independently an integer of 3. In some embodiments, n is 0. In some embodiments, n is an integer≥1 (e.g., 1, 2, 3, 4, 5, 6, 7, 8, 9, 10, 11, 12, or more). In some embodiments, m is an integer of 1. In some embodiments, m is an integer≥2 (e.g., 2, 3, 4, 6, 7, 8, 9, 10, 11, 12, or more). In some embodiments, m is an integer of 2, 3, or 4.

In some embodiments, the self-assembling peptide comprises or consists of an amino acid sequence as set forth in [(Y)i(Z)j(Y)k(X)l]m(Y)n (Formula IV), wherein each (X) is independently an ionic, polar amino acid, wherein each (Y) is independently a hydrophobic amino acid, wherein each (Z) is independently a non-ionic, polar amino acid, wherein each i, j, k, and l is independently an integer≥1, wherein m is an integer≥2, and wherein n=0 or an integer≥1. In some embodiments, each i, j, k, and l is independently an integer of 1. In some embodiments, each i, j, k, and l is independently an integer of 2. In some embodiments, each i, j, k, and l is independently an integer of 3. In some embodiments, n is 0. In some embodiments, n is an integer≥1 (e.g., 1, 2, 3, 4, 5, 6, 7, 8, 9, 10, 11, 12, or more). In some embodiments, m is an integer of 1. In some embodiments, m is an integer≥2 (e.g., 2, 3, 4, 6, 7, 8, 9, 10, 11, 12, or more). In some embodiments, m is an integer of 2, 3, or 4.

In some embodiments, the self-assembling peptide comprises or consists of an amino acid sequence as set forth in [(X)i(Y)j(Z)k(Y)l]m (Formula V), wherein each (X) is independently an ionic, polar amino acid, wherein each (Y) is independently a hydrophobic amino acid, wherein each (Z) is independently a non-ionic, polar amino acid, wherein each i, j, k, and l is independently an integer≥1, wherein m is an integer≥2, and wherein n=0 or an integer≥1. In some embodiments, each i, j, k, and l is independently an integer of 1. In some embodiments, each i, j, k, and l is independently an integer of 2. In some embodiments, each i, j, k, and l is independently an integer of 3. In some embodiments, n is 0. In some embodiments, n is an integer≥1 (e.g., 1, 2, 3, 4, 5, 6, 7, 8, 9, 10, 11, 12, or more). In some embodiments, m is an integer of 1. In some embodiments, m is an integer≥2 (e.g., 2, 3, 4, 6, 7, 8, 9, 10, 11, 12, or more). In some embodiments, m is an integer of 2, 3, or 4.

In some embodiments, the self-assembling peptide comprises or consists of an amino acid sequence as set forth in [(Y)i(X)j(Y)k(Z)l]m (Formula VI), wherein each (X) is independently an ionic, polar amino acid, wherein each (Y) is independently a hydrophobic amino acid, wherein each (Z) is independently a non-ionic, polar amino acid, wherein each i, j, k, and l is independently an integer≥1, wherein m is an integer≥2, and wherein n=0 or an integer≥1. In some embodiments, each i, j, k, and l is independently an integer of 1. In some embodiments, each i, j, k, and l is independently an integer of 2. In some embodiments, each i, j, k, and l is independently an integer of 3. In some embodiments, n is 0. In some embodiments, n is an integer≥1 (e.g., 1, 2, 3, 4, 5, 6, 7, 8, 9, 10, 11, 12, or more). In some embodiments, m is an integer of 1. In some embodiments, m is an integer≥2 (e.g., 2, 3, 4, 6, 7, 8, 9, 10, 11, 12, or more). In some embodiments, m is an integer of 2, 3, or 4.

In some embodiments, the self-assembling peptide comprises or consists of an amino acid sequence as set forth in [(Z)i(Y)j(X)k(Y)l]m (Formula VIII), wherein each (X) is independently an ionic, polar amino acid, wherein each (Y) is independently a hydrophobic amino acid, wherein each (Z) is independently a non-ionic, polar amino acid, wherein each i, j, k, and l is independently an integer≥1, wherein m is an integer≥2, and wherein n=0 or an integer≥1. In some embodiments, each i, j, k, and l is independently an integer of 1. In some embodiments, each i, j, k, and l is independently an integer of 2. In some embodiments, each i, j, k, and l is independently an integer of 3. In some embodiments, n is 0. In some embodiments, n is an integer≥1 (e.g., 1, 2, 3, 4, 5, 6, 7, 8, 9, 10, 11, 12, or more). In some embodiments, m is an integer of 1. In some embodiments, m is an integer≥2 (e.g., 2, 3, 4, 6, 7, 8, 9, 10, 11, 12, or more). In some embodiments, m is an integer of 2, 3, or 4.

In some embodiments, the self-assembling peptide comprises or consists of an amino acid sequence as set forth in [(Y)i(Z)j(Y)k(X)l]m (Formula VIII), wherein each (X) is independently an ionic, polar amino acid, wherein each (Y) is independently a hydrophobic amino acid, wherein each (Z) is independently a non-ionic, polar amino acid, wherein each i, j, k, and l is independently an integer≥1, wherein m is an integer≥2, and wherein n=0 or an integer≥1. In some embodiments, each i, j, k, and l is independently an integer of 1. In some embodiments, each i, j, k, and l is independently an integer of 2. In some embodiments, each i, j, k, and l is independently an integer of 3. In some embodiments, n is 0. In some embodiments, n is an integer≥1 (e.g., 1, 2, 3, 4, 5, 6, 7, 8, 9, 10, 11, 12, or more). In some embodiments, m is an integer of 1. In some embodiments, m is an integer≥2 (e.g., 2, 3, 4, 6, 7, 8, 9, 10, 11, 12, or more). In some embodiments, m is an integer of 2, 3, or 4.

Each (X) in the self-assembling peptides of Formulas I-IV may be an acidic amino acid or a basic amino acid. For example, in some embodiments, each (X) is a basic amino acid, including but not limited to arginine, lysine, histidine, and ornithine. In some embodiments, each (X) is an acidic amino acid, including, but not limited to aspartic acid and glutamic acid.

Each (Y) in the self-assembling peptides of Formulas I-IV may be an alanine, a valine, a leucine, an isoleucine, a methionine, a phenylalanine, a tryptophan, or a glycine.

Each (Z) is selected from the group consisting of the group consisting of serine, threonine, tyrosine, cysteine, glutamine, asparagine, and methionine.

The pharmaceutical compositions described herein may comprise one type of self-assembling peptide or multiple different types of self-assembling peptides. For example, in some embodiments, a pharmaceutical composition provided herein may comprise one type of self-assembling peptide (e.g., a self-assembling peptide comprising or consisting of an amino acid sequence as set forth in Formula I). In some embodiments, the pharmaceutical compositions described herein comprise two or more types (e.g., two, three, four, five, six, seven eight, nine, ten, or more types) of self-assembling peptides. When a pharmaceutical composition provided herein comprises more than one type of self-assembling peptide, the self-assembling peptides may all comprise amino acid sequences as set forth in a single Formula (i.e., one of Formulas I-IV) or may comprise amino acid sequences as set forth in different Formulas. When multiple types of self-assembling peptides are present in a pharmaceutical composition provided herein, the different types of peptides can be capable of interacting and forming higher order structures (e.g., β-sheets).

In some embodiments, the self-assembling peptide comprises or consists of between about 8 amino acid residues and about 50 amino acid residues. In some embodiments, the self-assembling peptide comprises or consists of between about 8 amino acid residues and 18 amino acid residues. For instance, the self-assembling peptide may comprise 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 40 amino acid residues. The self-assembling peptide size may be such that a tertiary structure of the self-assembling peptide does not disrupt the ability of the peptide to form a higher order structure (e.g., a nanofiber or a β-sheet) with other self-assembling peptides. In some embodiments, the self-assembling peptides comprise or consist of about 12 amino acid residues. In some embodiments, the self-assembling peptides comprise or consist of about 13 amino acid residues. In some embodiments, the self-assembling peptides comprise or consist of about 14 amino acid residues. In some embodiments, the self-assembling peptides comprise or consist of about 15 amino acid residues. In some embodiments, the self-assembling peptides comprise or consist of about 16 amino acid residues. In some embodiments, the self-assembling peptides comprise or consist of about 17 amino acid residues. In some embodiments, the self-assembling peptides comprise or consist of about 18 amino acid residues. In some embodiments, the self-assembling peptides comprise or consist of about 19 amino acid residues. In some embodiments, the self-assembling peptides comprise or consist of about 20 amino acid residues. In some embodiments, the self-assembling peptides comprise or consist of about 21 amino acid residues. In some embodiments, the self-assembling peptides comprise or consist of about 22 amino acid residues. In some embodiments, the self-assembling peptides comprise or consist of about 23 amino acid residues. In some embodiments, the self-assembling peptides comprise or consist of about 24 amino acid residues. In some embodiments, the self-assembling peptides comprise or consist of about 25 amino acid residues. In some embodiments, the self-assembling peptides comprise or consist of about 26 amino acid residues. In some embodiments, the self-assembling peptides comprise or consist of about 27 amino acid residues. In some embodiments, the self-assembling peptides comprise or consist of about 28 amino acid residues. In some embodiments, the self-assembling peptides comprise or consist of about 29 amino acid residues. In some embodiments, the self-assembling peptides comprise or consist of about 30 amino acid residues.

Exemplary self-assembling peptides are provided below in Table 1. The exemplary self-assembling peptides of Table 1 include alternating ionic, polar amino acid residues, hydrophobic amino acid residues, and non-ionic, polar amino acid residues. In some embodiments, the pharmaceutical compositions provided herein comprise a self-assembling peptide comprising or consisting of an amino acid sequence as set forth in SEQ NOs: 1-20 and 94-96.

TABLE 1

Exemplary self-assembling peptides

| SEQ ID NO: | Sequence | Number of residues |
|---|---|---|
| 1 | KLNLKLNLKLNL | 12 |
| 2 | LNLKLNLKLNLK | 12 |
| 3 | NLKLNLKLNLKL | 12 |
| 4 | LKLNLKLNLKLN | 12 |
| 5 | KLNLKLNLKLNLK | 13 |
| 6 | KLNLKLNLKLNLKLNLK | 17 |
| 7 | IQIKIQIKIQIK | 12 |
| 8 | IQIKIQIKIQIKI | 13 |
| 9 | KIQIKIQIKIQIK | 13 |
| 10 | QIKIQIKIQIKIQ | 13 |
| 11 | IKIQIKIQIKIQI | 13 |

TABLE 1-continued

Exemplary self-assembling peptides

| SEQ ID NO: | Sequence | Number of residues |
|---|---|---|
| 12 | INIKINIKINIKI | 13 |
| 13 | NLELNLELNLEL | 12 |
| 14 | NLDLNLDLNLDL | 12 |
| 15 | QLELQLELQLEL | 12 |
| 16 | LELQLELQLELQ | 12 |
| 17 | KANAKANAKANA | 12 |
| 18 | KVNVKVNVKVNV | 12 |
| 19 | RANARANARANARANA | 16 |
| 20 | KLTLKLTLKLTL | 12 |
| 94 | IEITIEITIEITI | 13 |
| 95 | ITIKITIKITIKI | 13 |
| 96 | KIQIKIQIKIQI | 12 |

In some embodiments, the self-assembling peptides may comprise one or more functional groups. In some embodiments, the functional group prevents or delays the degradation of the self-assembling peptides. In some embodiments, the self-assembling peptide comprises an N-terminal functional group. In some embodiments, the self-assembling peptide comprises a C-terminal functional group. In some embodiments, the self-assembling peptide comprises both an N-terminal functional group and a C-terminal functional group. For example, in some embodiments, the functional groups prevent or delay the degradation of the self-assembling peptides by enzymes (e.g., in vivo) (e.g., acetyl, formyl, chloroacetyl, benzyloxycarbonyl, bromoacetyl, tert-butoxycarbonyl, 9-fluorenylmethyloxycarbonyl, allyloxycarbonyl, methyl ester, benzyl ester, or t-butyl ester). Exemplary N-terminal functional groups include, but are not limited to, an acetyl, a formyl, pyroglutamyl (pGlu), biotin, polyethylene glycol (PEG), urea, alkylamine, a carbamate, a sulfonamide (e.g., 4-toluenesulfonyl, 4-nitrobenzenesulfonyl), dansyl, 2,4-dintrophenyl, fluorescein, 7-methoxycoumarin acetic acid, 9-fluorenylmethyloxycarbonyl, palmitic acid, succinyl, chloroacetyl, maleimide, benzyloxycarbonyl, bromoacetyl, nitrilotriacetyl, tertbutoxycarbonyl, 4-hydroxyphenylpropionic acid, allyloxycarbonyl, butyric acid, a fatty acid (e.g., hexanoic acid, octanoic acid, decanoic acid, palmitic acid, stearic acid, myristic acid, and lauric acid), and trityl. Exemplary C-terminal functional groups include, but are not limited to, an amido, an N-alkyl amide, an aldehyde, an ester (e.g., a methyl ester, a benzyl ester, or a t-butyl ester), an alcohol, para-nitroanilide (pNA), 7-amino-4-methylcoumarin (Amc), a hydrazide, hydroxamic acid, chloromethylketone, p-nitroaniline, paranitrophenol, hydroxysucinimide ester, fluoromethylketone, cysteamide, 9-fluorenemethyl (Fm) ester, allyl ester, 2,4-dimethoxybenzyl ester, 2-phenylisopropyl ester, p-nitrobenzyl ester, and 2-chlorotrityl ester.

In some embodiments, the self-assembling peptides described herein can comprise an N-terminal acetyl group and/or a C-terminal amine group. For example, exemplary self-assembling peptides comprising both of these functional groups are provided below in Table 2. In some embodiments, the pharmaceutical compositions provided herein comprise a self-assembling peptide comprising or consisting of an amino acid sequence as set forth in SEQ ID NOs: 21-40 and 97-99.

TABLE 2

Exemplary self-assembling peptides comprising an N-terminal acetyl group and a C-terminal amine group

| SEQ ID NO: | Name | Sequence | Number of residues |
|---|---|---|---|
| 21 | KLNL12 | Ac-KLNLKLNLKLNL-NH2 | 12 |
| 22 | LNLK12 | Ac-LNLKLNLKLNLK-NH2 | 12 |
| 23 | NLKL12 | Ac-NLKLNLKLNLKL-NH2 | 12 |
| 24 | LKLN12 | Ac-LKLNLKLNLKLN-NH2 | 12 |
| 25 | KLNL13 | Ac-KLNLKLNLKLNLK-NH2 | 13 |
| 26 | KLNL17 | Ac-KLNLKLNLKLNLKLNLK-NH2 | 17 |
| 27 | IQIK12 | Ac-IQIKIQIKIQIK-NH2 | 12 |
| 28 | IQIK13 | Ac-IQIKIQIKIQIKI-NH2 | 13 |
| 29 | KIQI13 | Ac-KIQIKIQIKIQIK-NH2 | 13 |
| 30 | QIKI13 | Ac-QIKIQIKIQIKIQ-NH2 | 13 |
| 31 | IKIQ13 | Ac-IKIQIKIQIKIQI-NH2 | 13 |
| 32 | INIK13 | Ac-INIKINIKINIKI-NH2 | 13 |
| 33 | NLEL12 | Ac-NLELNLELNLEL-NH2 | 12 |
| 34 | NLDL12 | Ac-NLDLNLDLNLDL-NH2 | 12 |
| 35 | QLEL12 | Ac-QLELQLELQLEL-NH2 | 12 |
| 36 | LELQ12 | Ac-LELQLELQLELQ-NH2 | 12 |
| 37 | KANA12 | Ac-KANAKANAKANA-NH2 | 12 |
| 38 | KVNV12 | Ac-KVNVKVNVKVNV-NH2 | 12 |
| 39 | RANA16 | Ac-RANARANARANARANA-NH2 | 16 |
| 40 | KLTL12 | Ac-KLTLKLTLKLTL-NH2 | 12 |
| 97 | IEIT13 | Ac-IEITIEITIEITI-NH2 | 13 |
| 98 | ITIK13 | Ac-ITIKITIKITIKI-NH2 | 13 |
| 99 | KIQI12 | Ac-KIQIKIQIKIQI-NH2 | 12 |

In some embodiments, the self-assembling peptides described herein comprise at least one biologically-active peptide motif. Without wishing to be bound by any particular theory, biologically-active peptide motifs may facilitate one or more biological processes in, over or surrounding a pharmaceutical composition (e.g., a hydrogel) described herein, including, for example, cell adhesion, differentiation, proliferation, recruitment, and/or homing; neurite outgrowth; bioactive molecule recruitment (e.g., as a binding site for the bioactive molecule), retention, and/or reconstitution. The biologically active peptide motif may be present anywhere along the amino acid sequence of the self-assembling peptide and preferably does not interfere with the ability of the self-assembling peptide to form a higher order structure (e.g., a nanofiber or a β-sheet) via intramolecular interactions or intermolecular interactions with other self-assembling peptides. For example, in some embodiments, the biologically-active peptide motif is present at the N-terminal end of the self-assembling peptide. In some embodiments, the biologically-active peptide motif is present at the C-terminal end of the self-assembling peptide. The self-assembling peptide can comprise one or more (e.g., one, two, three, four, five, six, seven, eight, or more) biologically active peptide motifs. When the self-assembling peptide comprises more than one biologically-active peptide motifs, each motif may be of the same type or each motif may be different. Exemplary biologically active peptide motifs may be derived from proteins such as laminin-1, collagen IV, fibronectin, elastin, bone marrow homing peptide 1, bone marrow homing peptide 2, or myelopeptide. Non-limiting examples of biologically active motifs are provided below in Table 3. In some embodiments, a self-assembling peptide provided herein comprises a biologically active peptide motif comprising an amino acid sequence as set forth in SEQ ID NOs: 41-70.

TABLE 3

Exemplary biologically active peptide motifs.

| SEQ ID NO: | Peptide Amino Acid Sequence | Protein |
|---|---|---|
| 41 | AASIKVAVSADR | Laminin-1 |
| 42 | CSRARKQAASIKVAVSADR | Laminin-1 |
| 43 | YIGSR | Laminin-1 |
| 44 | PDGSR | Laminin-1 |
| 45 | RYVVLPR | Laminin-1 |
| 46 | KAFDITYVRLKF | Laminin-1 |
| 47 | TAGSCLRKFSTM | Collagen IV |
| 48 | RNIAEIIKDI | Laminin-1 |
| 49 | YVRL | Laminin-1 |
| 50 | IRVTLN | Laminin-1 |
| 51 | TTVKYIFR | Laminin-1 |

TABLE 3-continued

Exemplary biologically active peptide motifs.

| SEQ ID NO: | Peptide Amino Acid Sequence | Protein |
|---|---|---|
| 52 | SIKIRGTY | Laminin-1 |
| 53 | RQVFQVAYIIIKA | Laminin-1 |
| 54 | FQIAYVIVKA | Laminin-1 |
| 55 | GQLFHVAYIIIKA | Laminin-1 |
| 56 | FHVAYVLIKA | Laminin-1 |
| 57 | LENGEIVSLVNGR | Laminin-1 |
| 58 | LGTIPG | fibronectin |
| 59 | DGEA | fibronectin |
| 60 | REDV | fibronectin |
| 61 | GVGVP | elastin |
| 62 | GVGVAP | elastin |
| 63 | IKVAV | Laminin-1 |
| 64 | PFSSTKT | Bone marrow homing peptide 2 |
| 65 | SKPPGTSS | Bone marrow homing peptide 1 |
| 66 | SDPGYIGSR | Laminin-1 |
| 67 | RNIAELLKDI | Laminin-1 |
| 68 | PRGDSGYRGDSG | Collagen IV |
| 69 | GFLGFPT | myelopeptide |
| 70 | YGPDSGR | Laminin-1 |

In some embodiments, the self-assembling peptide comprises a biologically active peptide motif shown below in Table 4. In some embodiments, the self-assembling peptide comprises or consists of an amino acid sequence as set forth in SEQ ID NOs: 71-90.

TABLE 4

Exemplary self-assembling peptides comprising biologically-active peptide motifs.

| SEQ ID NO: | Name | Amino Acid Sequence | Number of residues |
|---|---|---|---|
| 71 | KLNL12YIG | Ac-KLNLKLNLKLNLGYIGSR-NH2 | 18 |
| 72 | KLNL12PDG | Ac-KLNLKLNLKLNLGPDGSR-NH2 | 18 |
| 73 | KLNL12GVG | Ac-KLNLKLNLKLNLGGVGVAP-NH2 | 19 |
| 74 | KLNL12PFS | Ac-KLNLKLNLKLNLGPFSSTKT-NH2 | 20 |
| 75 | KLNL12PRG | Ac-KLNLKLNLKLNLGPRGDSGYRGDSG-NH2 | 25 |
| 76 | KIQI13YIG | Ac-KIQIKIQIKIQIKGYIGSR-NH2 | 19 |
| 77 | KIQI13PDG | Ac-KIQIKIQIKIQIKGPDGSR-NH2 | 19 |
| 78 | KIQI13GVG | Ac-KIQIKIQIKIQIKGGVGVAP-NH2 | 20 |
| 79 | KIQI13PFS | Ac-KIQIKIQIKIQIKGPFSSTKT-NH2 | 21 |

TABLE 4-continued

Exemplary self-assembling peptides comprising biologically-active peptide motifs.

| SEQ ID NO: | Name | Amino Acid Sequence | Number of residues |
|---|---|---|---|
| 80 | KIQI13PRG | Ac-KIQIKIQIKIQIKGPRGDSGYRGDSG-NH2 | 26 |
| 81 | NLEL12YIG | Ac-NLELNLELNLELGYIGSR-NH2 | 18 |
| 82 | NLEL12PDG | Ac-NLELNLELNLELGPDGSR-NH2 | 18 |
| 83 | NLEL12GVG | Ac-NLELNLELNLELGGVGVAP-NH2 | 19 |
| 84 | NLEL12PFS | Ac-NLELNLELNLELGPFSSTKT-NH2 | 20 |
| 85 | NLEL12PRG | Ac-NLELNLELNLELGPRGDSGYRGDSG-NH2 | 25 |
| 86 | RANA16YIG | Ac-RANARANARANARANAGYIGSR-NH2 | 22 |
| 87 | RANA16PDG | Ac-RANARANARANARANAGPDGSR-NH2 | 22 |
| 88 | RANA16GVG | Ac-RANARANARANARANAGGVGVAP-NH2 | 23 |
| 89 | RANA16PFS | Ac-RANARANARANARANAGPFSSTKT-NH2 | 24 |
| 90 | RANA16PRG | Ac-RANARANARANARANAGPRGDSGYRGDSG-NH2 | 29 |

The concentration of self-assembling peptide present in the pharmaceutical compositions provided herein may be varied in order to change the rheological properties of the composition. In some embodiments, the pharmaceutical compositions may comprise between about 0.01% (w/v) and about 10% (w/v) of a self-assembling peptide described herein. In some embodiments, the pharmaceutical compositions may comprise between about 0.1% (w/v) and about 5% (w/v) of a self-assembling peptide described herein. In some embodiments, the pharmaceutical compositions may comprise between about 0.1% (w/v) and about 2% (w/v) of a self-assembling peptide described herein. In some embodiments, the pharmaceutical compositions may comprise between about 0.5% (w/v) and about 3% (w/v) of a self-assembling peptide described herein. In some embodiments, the pharmaceutical compositions may comprise between about 0.5% (w/v) and about 1.5% (w/v) of a self-assembling peptide described herein. In some embodiments, the pharmaceutical compositions may comprise between about 1% (w/v) and about 3% (w/v) of a self-assembling peptide described herein. In some embodiments, the pharmaceutical compositions comprise about 0.5%, about 1% (w/v), about 1.5% (w/v), about 2% (w/v), about 2.5% (w/v), about 3% (w/v), about 3.5% (w/v), about 4% (w/v), about 4.5% (w/v), or about 5% (w/v) of a self-assembling peptide described herein.

In some embodiments, the pharmaceutical compositions may be an aqueous solution or a hydrogel, or it may be dehydrated (e.g., a powder). Hydrogels formed by the self-assembling peptides described herein may be porous or solid. In some embodiments, the hydrogels comprise pores having an average diameter of from about 1 nm to about 2,000 µm, of from about 10 nm to about 1,000 µm, of from about 10 nm to about 500 µm, of from about 10 nm to about 100 µm, of from about 10 nm to about 1µm, of from about 5 nm to about 500 nm, or of from about 5 nm to about 250 nm.

In some embodiments, the pharmaceutical compositions provided herein may be hydrogels of different sizes and geometric shapes, including films and particles, e.g., nanoparticles or microparticles. In some embodiments, the pharmaceutical composition may be layered onto a surface (e.g., a hydrogel). The pharmaceutical composition particle size will vary depending on the particular use intended for such a particle. In general, particles can have at least one dimension in the range from about 1000 µm to about 2000 µm (e.g., about 1,000 µm, about 1,100 µm, 1,200 µm, 1,300 µm, 1,400 µm, 1,500 µm, 1,600 µm, 1,700 µm, 1,800 µm, 1,900 µm, or 2,000 µm).

The self-assembling peptides described herein may be advantageously formulated at physiological pH and the self-assembling peptide(s) therein remain soluble and stable. In some embodiments, the pharmaceutical compositions described herein have a pH of from about 5 to about 8. In some embodiments, the pharmaceutical compositions have a pH of from about 6. to about 8. In some embodiments, the pharmaceutical compositions have a pH of from about 5.5. to about 7.5. In some embodiments, the pharmaceutical compositions have a pH of from about 6 to about 7.4. In some embodiments, the pharmaceutical compositions have a pH of from about 6.5 to about 7.5. In some embodiments, the pharmaceutical compositions have a pH of from about 7 to about 7.5. In some embodiments, the pharmaceutical compositions have a pH of about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. The pH of a pharmaceutical composition described herein may be regulated by including a buffer system. Alternatively, the self-assembling peptides may act as a buffer in the pharmaceutical compositions. The pH of the pharmaceutical composition may be adjusted using one or more acids or bases such as sodium hydroxide, potassium hydroxide, hydrochloric acid, phosphoric acid, sodium carbonate and sodium hydrogen carbonate.

In some embodiments, the pharmaceutical compositions may comprise a buffer such as phosphate buffered saline (PBS). In some embodiments, the pharmaceutical compositions may comprise a medium for cell culture, including, but not limited to Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (SAFC Biosciences) and Iscove's Modified Dulbecco's Medium.

The pharmaceutical compositions described herein can be formulated such that the pH of the composition is neutral or physiological (e.g., a pH of from about 6 to about 8) and the self-assembling peptides therein have a non-zero net charge. Without wishing to be bound by any particular theory, when formulated at neutral or physiological pH, the non-zero net charge of the self-assembling peptides enables the peptides to readily form electrostatic interactions with molecules of the opposite charge. This property can be advantageously used to promote adhesion of the pharmaceutical composition to a desired surface. This is particularly advantageous in clinical applications where the pharmaceutical compositions are applied to tissue enriched with biomolecules (e.g., glycoproteins) having a non-zero net charge.

Moreover, without wishing to he bound by any particular theory, self-assembling peptides described herein having a net positive charge when formulated at physiological pH, are particularly advantageous in therapeutic applications as they may be bactericidal and/or bacteriostatic. Thus, the self-assembling peptides may be readily used in a variety of applications where reduced bacterial burden is desired.

In some embodiments, the net charge of the self-assembling peptide is greater than or equal to +1 or less than or equal to −1 when the pharmaceutical composition has a pH of from about 5 to about 8. In some embodiments, the net charge of the self-assembling peptide is from about +1 to about +6 (e.g., +1, +2, +3, +4, +5, or +6) when the pharmaceutical composition has a pH of from about 5 to about 8 (e.g., 7.4). In some embodiments, the net charge of the self-assembling peptide is from about −1 to about −6 (e.g., −1, −2, −3, −4, −5, or −6) when the pharmaceutical composition has a pH of from about 5 to about 8 (e.g., 7.4).

In some embodiments, the pharmaceutical compositions provided herein have an elastic modulus in the range between about 10 Pascal (Pa) to about 10,000 Pa. As used herein, the term "elastic modulus" refers to a composition's tendency to be deformed elastically (i.e., non-permanently) when a force is applied to it. Generally, the elastic modulus of an object is defined as the slope of its stress-strain curve in the elastic deformation region. Specifying how stress and strain are to be measured, including directions, allows for many types of elastic moduli to be defined. Young's modulus (E) describes tensile elasticity, or the tendency of an object to deform along an axis when opposing forces are applied along that axis; it is defined as the ratio of tensile stress to tensile strain. It is often referred to simply as the elastic modulus. The shear modulus or modulus of rigidity (G or μ) describes an object's tendency to shear (the deformation of shape at constant volume) when acted upon by opposing forces; it is defined as shear stress over shear strain. The shear modulus is part of the derivation of viscosity. The bulk modulus (K) describes volumetric elasticity, or the tendency of an object to deform in all directions when uniformly loaded in all directions; it is defined as volumetric stress over volumetric strain and is the inverse of compressibility. The bulk modulus is an extension of Young's modulus to three dimensions. In some embodiments, a pharmaceutical composition described herein (e.g., a hydrogel) has a storage modulus of at least about 10 Pa. In some embodiments, a pharmaceutical composition described herein has a storage modulus of at least about 50 Pa. In some embodiments, a pharmaceutical composition described herein has a storage modulus of at least about 100 Pa. In some embodiments, a pharmaceutical composition described herein has a storage modulus of at least about 500 Pa. In some embodiments, a pharmaceutical composition described herein has a storage modulus of at least about 1,000 Pa. In some embodiments, a pharmaceutical composition described herein has a storage modulus of between about 10 Pa and about 5,000 Pa. In some embodiments, a pharmaceutical composition described herein has a storage modulus of between about 50 Pa and about 500 Pa. In some embodiments, a pharmaceutical composition described herein has a storage modulus of between about 10 Pa and about 1,000 Pa. In some embodiments, a pharmaceutical composition described herein has a storage modulus of between about 500 Pa and about 5,000 Pa.

In some embodiments, increased ionic strength may increase the stiffness and/or gelation kinetics of the self-assembling peptides present in the pharmaceutical compositions described herein. In some embodiments, increased ionic strength may be physiological ionic strength. The ionic strength of the pharmaceutical compositions may be increased when the compositions are administered into and/or onto a subject (e.g., a human subject). Alternatively, the ionic strength of the pharmaceutical compositions described herein may be increased by admixing the compositions with one or more tonicity agents. Exemplary tonicity agents include, but are not limited to, sodium chloride, calcium chloride, potassium chloride, and potassium phosphate. In some embodiments, the pharmaceutical compositions described herein do not include a tonicity agent. In some embodiments, the pharmaceutical compositions described herein comprise between about 0.01 M to about 0.3 M tonicity agent. In some embodiments, the pharmaceutical compositions described herein comprise between about 0.1 M to about 0.3 M tonicity agent. In some embodiments, the pharmaceutical compositions described herein comprise between about 0.1M to about 0.2 M tonicity agent. In some embodiments, the pharmaceutical compositions described herein comprise 0.01 M, 0.02 M, 0.03 M, 0.04 M, 0.05 M, 0.06 M, 0.07 M, 0.08 M, 0.09 M, 0.1 M, 0.15 M, 0.2 M, 0.25 M, or 0.3 M tonicity agent.

In some embodiments, the pharmaceutical compositions described herein are formulated such that they are hypoosmotic in relation to the site of administration in a subject. In some embodiments, the pharmaceutical compositions described herein are formulated such that they are isoosmotic in relation to the site of administration in a subject. In some embodiments, the pharmaceutical compositions described herein are formulated such that they are hyperosmotic in relation to the site of administration in a subject.

In some embodiments, the pharmaceutical compositions described herein comprise a cell (e.g., an isolated cell). In some embodiments, the pharmaceutical composition (e.g., a hydrogel) can enhance the viability of a cell therein thereby facilitating the delivery of viable cells to a desired site (e.g., an injured or defective body tissue). In some embodiments, the pharmaceutical composition is an aqueous solution that comprises between about $10^4$ to about $10^8$ cells/mL (e.g., $10^4$, $10^5$, $10^6$, $10^7$ cells/mL). In some embodiments, the pharmaceutical composition is an aqueous solution that comprises between about $10^4$ to about $10^6$ cells/mL. In some embodiments, the pharmaceutical composition comprises one cell type. In some embodiments, the pharmaceutical composition comprises more than one cell type (e.g., two, three, four, five, or more cell types).

Any appropriate cell may be comprised in the pharmaceutical compositions, depending on the desired application. For example, in some embodiments the pharmaceutical composition (e.g., a hydrogel) is seeded with an animal cell or a plant cell. When a hydrogel, the cells may be encapsulated within the hydrogel. In some embodiments, the pharmaceutical composition comprises a mammalian cell. Exemplary mammalian cells, include, but are not limited to, stem cells (embryonic stem cells, mesenchymal stem cells, bone-marrow derived stem cells, hematopoietic stem cells, neural stem cells, and hair follicular stem cells), chondrocyte progenitor cells, pancreatic progenitor cells, myoblasts, fibroblasts, keratinocytes, neuronal cells, glial cells, astrocytes, pre-adipocytes, adipocytes, vascular endothelial cells, endothelial progenitor cells, mesenchymal cells, neural stem cells, immune cells, (e.g., B-cells and T-cells), smooth muscle progenitor cells, cardiac myocytes, fetal dermal fibroblasts, epidermal keratinocytes, myoblasts, and capillary endothelial cells. In some embodiments, the cell is a genetically-modified cell (e.g., a cell modified to express and secrete a desired compound such as a growth factor, a differentiation factor, a cytokine, a chimeric antigen receptor, or an antibody or a fragment thereof). In some embodiments, the cell is a tissue culture cell line cell. Exemplary tissue culture cell line cells include, but are not limited to, C166 cells, C6 glioma cell line, AML12, HeLa cells, and Chinese Hamster Ovary cells (CHO cells).

In some embodiments, the pharmaceutical compositions provided herein comprise a bioactive molecule, including but not limited to, an extracellular matrix protein (e.g., fibronectin, vitronectin, and laminin), a cytokine, a growth factor, a differentiation factor, insulin, a nucleic acid, a vitamin, a fatty acid, and a therapeutic agent.

Exemplary growth factors and cytokines include, but are not limited to, stem cell factor (SCF), granulocyte-colony stimulating factor (G-CSF), granulocyte-macrophage stimulating factor (GM-CSF), stromal cell-derived factor-1, vascular endothelial growth factor (VEGF), platelet derived growth factor (PDGF), an angiopoeitin, epidermal growth factor (EGF), basic fibroblast growth factor (bFGF), hepatocyte nuclear factor-1 (HNF-1), nerve growth factor (NGF), bone morphogenetic protein (BMP), fibroblast growth factor (FGF), hepatocyte growth factor, insulin-like growth factor (IGF-1), interleukin (IL)-3, IL-la, IL-Iβ, IL-6, IL-7, IL-8, IL-11, and IL-13, colony- stimulating factors, thrombopoietin, erythropoietin, fit3-ligand, and tumor necrosis factor α (TNFα).

In some embodiments, the bioactive molecule is a therapeutic agent. As used herein, the term "therapeutic agent" refers to a compound used in the diagnosis, treatment, or prevention of a disease or disorder in a subject. Any therapeutic agent known to be of benefit in the diagnosis, treatment or prevention of a disease or disorder may be included in a pharmaceutical compositions provided herein. Therapeutic agents include pharmacologically active compounds (e.g., antibiotics and anti-inflammatory agents), hormones, DNA (e.g., plasmid DNA), RNA, siRNA, shRNA, anti-sense RNA, proteins (e.g., antibodies and fragments thereof, and enzymes), lipids, pro-inflammatory molecules, and combinations thereof. Any of the therapeutic agents may be combined to the extent such combination is biologically compatible. The amount of therapeutic agent in the pharmaceutical composition will depend on various factors including, for example, the effective dose of therapeutic agent required for a particular course of action and the required period of time for release of the therapeutic agent. Additional exemplary therapeutic agents and appropriate dosing amounts and regimens are described, for example, in Harrison's Principles of Internal Medicine, 19th Edition, Eds. D. L. Kasper et al., McGraw-Hill, New York, N.Y. (2015); Physician's Desk Reference, 71st Edition, Montvale, N.J., Physician's Desk Reference Inc. (2016); and Goodman and Gilman's: The Pharmacological Basis of Therapeutics, 13th Edition, Eds. L. L. Brunton et al., McGraw-Hill, New York, N.Y. (2018); each of which is incorporated herein by reference.

Uses of the Self-Assembling Peptides and Pharmaceutical Compositions

The self-assembling peptides and pharmaceutical compositions described herein may be used in a variety of in vitro and in vivo applications, including cell culture applications and clinical applications.

Cell Culture

In some embodiments, the self-assembling peptides and pharmaceutical compositions described herein may be used in the culture of cells (e.g., isolated human cells). For instance, hydrogels comprising the self-assembling peptides described herein may be substrates for cell culture. As described above, hydrogels formed by the self-assembling peptides described herein may comprise one or higher order structures (e.g., nanofibers and three-dimensional mesh) that provide a spatiotemporal substrate for cells. Advantageously, since the hydrogels can be formulated at physiological pH, they may provide an adequate environment for cell growth and proliferation.

Any of the cell types described in detail above may be cultured in the hydrogels described herein. Cells may be seeded directly onto a preformed hydrogel or they may be admixed with an aqueous pharmaceutical composition, which upon gelation forms a hydrogel. The liquid phase of the hydrogel may be supplemented with one or more culture medium components (e.g., growth factors and serum) to provide the necessary factors to promote cell survival and proliferation. Appropriate conditions and factors necessary to sustain cell survival and growth are known in the art (see, e.g., Freshney, Culture of Animal Cells: A Manual of Basic Technique, Wiley-Liss, New York, N.Y. (2000); and Cells: A Laboratory Manual (Spector, D. L., Goldman, R. D. and Leinwand, L. A., eds.), Cold Spring Harbor Laboratory Press, Cold Spring Harbor, N.Y. (1998).

The self-assembling peptides and pharmaceutical compositions provided herein may be used in a variety of applications including, for example, to perform cell culture, in cosmetics (e.g., skin and hair care products), for tissue engineering, as coating agents (e.g., for medical devices such as contact lenses), as lubricants (e.g., in ophthalmic solutions or as joint lubricants), as hemostatic agents, as desiccants, as bone filler material, as artificial vitreous bodies, as artificial lenses, as drug delivery devices, as water retention materials, and in biomaterial applications.

Clinical Applications

In some embodiments, the self-assembling peptides and pharmaceutical compositions described herein may be used in a variety of clinical applications. Thus, provided herein are various methods of treating a subject by administering an effective amount of a pharmaceutical composition described herein to a specific site in or on a subject. As described above, a particular advantage of the pharmaceutical compositions described herein is that they may be formulated at physiological pH (e.g., from about pH 6 to about pH 8), and therefore may result in reduced pain and reduced tissue damage upon contact with the subject, as compared to pharmaceutical compositions of self-assembling peptides that are formulated at acidic or basic pH.

The amount, for example, volume or concentration, of pharmaceutical compositions that is administered (for example, applied or injected) to a subject may vary depending upon the form of the pharmaceutical composition (e.g., as an aqueous solution or hydrogel) and the route of administration utilized. The exact formulation, route of administration, volume, and amount of pharmaceutical composition can be chosen in view of the subject's condition and in view of the particular target area or location to which the pharmaceutical composition is administered. Specific dosage and treatment regimens for any particular subject may depend upon a variety of factors, including the specific self-assembling peptide, the dimension of the area that is being treated, the desired thickness of the resulting hydrogel (when an aqueous solution is administered), and the length of time of treatment. Other factors that may affect the specific dosage and treatment regimens include the age, body weight, health status, sex, time of administration, rate of degradation, the severity and course of the disease, condition or symptoms. In some embodiments, the pharmaceutical composition may be administered in a single dose. In other embodiments, the pharmaceutical composition may be administered in more than one dose (e.g., two, three, four, five, six, or more doses).

In some embodiments, a pharmaceutical composition in the form of a pre-polymerized hydrogel is administered to a subject. In some embodiments, the pharmaceutical composition is a hydrogel that is formed in vitro and administered to the desired location in the subject.

In some embodiments, a pharmaceutical composition in the form of an aqueous solution is administered to a subject. A hydrogel may be formed in vivo after administration of the aqueous solution. Since the self-assembling peptides polymerize in response to changes in tonicity, the hydrogel may form upon contact with a subject during the administration or shortly thereafter.

The pharmaceutical compositions may be administered by introducing a delivery device at or near a predetermined or desired target area of a subject. The delivery device may be a conventional device or designed to accomplish at least one of to reach a specific target area, achieve a specific dosing regimen, deliver a specific target volume, amount, or concentration, and deliver accurately to a target area. Suitable delivery devices include, but are not limited to, syringes, pipettes, tubes, catheters, syringe catheters, auto-injectors, and other needle-based device to the predetermined or desired target area of a subject. The gauge of a syringe needle may be selected to provide an adequate flow of a pharmaceutical composition from the syringe to the target area.

The effective amount may comprise volumes of from about 0.1 milliliters (mL) to about 100 mL of a pharmaceutical composition (if administered as an aqueous solution). In some embodiments, an effective amount may be from about 0.1 mL to about 10 mL of pharmaceutical composition.). In some embodiments, an effective amount may be from about 0.5 mL to about 5 mL of pharmaceutical composition. In some embodiments, an effective amount may be from about 1 mL to about 5 mL of pharmaceutical composition. In some embodiments, an effective amount may be about 0.5 mL of pharmaceutical composition. In some embodiments, an effective amount may be about 1.0 mL of pharmaceutical composition. In some embodiments, an effective amount may be about 1.5 mL of pharmaceutical composition. In some embodiments, an effective amount may be about 2.0 mL of pharmaceutical composition. In some embodiments, an effective amount may be about 2.5 mL of pharmaceutical composition. In some embodiments, an effective amount may be about 0.1 mL to about 5 mL per $cm^2$ of target area. In some embodiments, an effective amount may be about 1 mL per $cm^2$ of target area. In some embodiments, an effective amount may be about 2 mL per $cm^2$ of target area.

The pharmaceutical compositions may be administered to a subject by any appropriate route known in the art including, without limitation, injection, implantation, microinjection, and direct application. Administration via injection includes, without limitation, cutaneous, intramuscular, intradermal, subdermal, and subcutaneous injections.

In some embodiments, the pharmaceutical composition is administered (e.g., injected or implanted) to a subject in a single dose at one location to produce the desired result. In some embodiments, the pharmaceutical composition is administered as several doses to produce the desired result. In some embodiments, when multiple doses of the pharmaceutical composition are administered, each administration occurs after a specific period of time, e.g., 1 day, 2 days, 3 days, 4 days, 5 days, 6 days, 1 week, 2 weeks, 1 month, 2 months, 3 months, or more.

In some embodiments, a hydrogel that has formed or is present at a site in a subject may be removed by contacting the hydrogel with a solution including a hypotonic concentration of tonicity agent as compared to the hydrogel. In some embodiments, a hydrogel that has formed or is present at a site in a subject may be removed by contacting the hydrogel with water. In some embodiments, a hydrogel that has formed or is present at a site in a subject may be removed by contacting the hydrogel with a solution that is hypotonic in relation to the site in the subject. In some embodiments, a hydrogel that has formed or is present at a site in a subject may be removed by contacting the hydrogels with a solution that is isotonic with sugars (e.g., dextrose and sucrose) to the site in the subject. In some embodiments, a hydrogel that has formed or is present at a site in a subject may be removed by contacting the hydrogels with a solution that is isotonic with salts bearing low ionic strength (e.g., NaCl—"Normal Saline") compared to the salts in body fluid.

The hydrogel may be contacted with the solution for a sufficient period of time to disrupt (e.g., disrupt the structure or morphology) of the hydrogel and/or cause the hydrogel to detach from the site in the subject. In some embodiments, the hydrogel is contacted with the solution for about 5 minutes, for about 10 minutes, for about 20 minutes, for about 30 minutes, for about 1 hour, for about 2 hours, for about 3 hours, or more.

In some embodiments, a pharmaceutical composition described herein may be used as a delivery device to specifically target release of a bioactive molecule or therapeutic agent. In some embodiments, the pharmaceutical composition may be formulated such that the composition allows for the spontaneous release of a bioactive molecule or therapeutic agent (e.g., after administration to a subject). In some embodiments, the pharmaceutical composition may be formulated such that the pharmaceutical composition allows for the controlled release of a bioactive molecule or therapeutic agent. In some embodiments, the bioactive molecule or therapeutic agent is released from the pharmaceutical composition (e.g., a hydrogel) for a prolonged period of time (e.g., from about 12 hours to about 2 months). In some embodiments, the bioactive molecule or therapeutic agent is released from the pharmaceutical composition for about 12 hours, one day, two days, three days, four days, five days, six days, one week, two weeks, three weeks, one month, two months, three months, or more. The release kinetics will vary according to the amino acid sequence of the self-assembling peptide present in the pharmaceutical composition, the concentration of the self-assembling peptide in the pharmaceutical composition, and the biochemical and physical properties of the bioactive molecule or therapeutic agent.

1. Gastrointestinal Obstruction

The self-assembling peptides and pharmaceutical compositions described herein may be used to prevent gastrointestinal obstruction in a subject. Methods of preventing gastrointestinal obstruction in a subject using a pharmaceutical composition comprising self-assembling peptides are known in the art and can be adapted for delivering the pharmaceutical compositions and self-assembling peptides described herein (see, e.g., U.S. Pat. No. 9,724,448, the entire contents of which are expressly incorporated herein by reference). For example, endoscopic mucosal resection (EMR) and endoscopic submucosal dissection (ESD) are primary surgical options for the resection of lesions, such as polyps, ulcers, and cancerous tumors in the gastrointestinal tract (see, e.g., Wallace (2017) Gastroenterol. Hepatol. (NY) 13(6): 371-4). Although EMR and ESD are minimally invasive procedures, obstructions in the gastrointestinal tract can be caused by scar contraction/shrinking during the healing process. One form of gastrointestinal obstruction may be a stenosis, a narrowing in a tubular organ or structure, such as the gastrointestinal tract, which may lead to a partial or full obstruction in the gastrointestinal tract. Methods of preventing stenosis in the gastrointestinal tract of a subject (e.g., in one or more of the mouth, throat, esophagus, stomach, small intestine, large intestine, colon or rectum) are provided. In some embodiments, an effective amount of a pharmaceutical compositions (e.g., an aqueous solution) described herein are administered using a medical device (e.g., a syringe, pipette, tube, syringe catheter, catheter, or endoscope) to a site in the gastrointestinal tract of the subject. In some embodiments, the aqueous solution forms a hydrogel at the site of administration thereby allowing for the prevention of stenosis at the site of administration. In some embodiments, the self-assembling peptides may facilitate mucosal epithelium formation to prevent or reduce post-operative scar formation, which may contribute to the prevention or reduction in gastrointestinal obstruction or stenosis. In some embodiments, the hydrogel provides a scaffold for the infiltration of cells that promote healing of the site of administration of the hydrogel.

In some embodiments, a pharmaceutical composition provided herein (e.g., an aqueous solution) may be administered (e.g., by injection) to submucosa at a site in the gastrointestinal tract of a subject prior to performing an excision of a lesion (e.g., using EMR or ESD). The submucosa is a thin connective tissue layer with a lax structure. In some embodiments, injection of the pharmaceutical composition to the submucosa forms a bulla and lifts the lesion above, thereby facilitating removal of the lesion. In some embodiments, the pharmaceutical composition elevates the submucosa for a period of time from about 20 minutes to about 1 hour. In some embodiments, the pharmaceutical composition elevates the submucosa for about 20 minutes, about 30 minutes, about 40 minutes, about 50 minutes, about 1 hour, about 2 hours, about three hours, about four hours, about five hours, or more.

2. Tissue Repair or Regeneration

The self-assembling peptides and pharmaceutical compositions described herein may be used to promote or enhance the repair or regeneration of tissue in a subject. The self-assembling peptides and pharmaceutical compositions may promote or enhance distinct types of tissue including, but not limited to, skin, bone, cartilage, neural tissue, ligaments, tendons, vascular tissue, and muscle (e.g. cardiac tissue). In some embodiments, the subject has a congenital disease or condition resulting in a need for tissue repair or regeneration. In some embodiments, the subject has experienced an injury resulting in a need for tissue regeneration. The injury may occur as a result of surgery, trauma, stroke, tumor, a disease or disorder (e.g., a neurodegenerative disease or disorder). The methods and compositions described herein may restore the structural and/or functional integrity of the tissue (e.g., to the structural and/or functional state of the tissue prior to an injury). Methods for promoting tissue regeneration using hydrogels comprising self-assembling peptides are known in the art and can be adapted for use with the self-assembling peptides and hydrogels described herein (see, e.g., U.S. Pat. No. 7,846,891 and U.S. Publication Nos. 2016/0362451 and 2017/0128172, the entire contents of each which are expressly incorporated herein by reference).

In some embodiments, the self-assembling peptides and pharmaceutical compositions described herein may be used to ameliorate or treat the effects of tissue degeneration of an organ, to repair an injury to an organ or other body structure or to form an organ or other body structure. Such organs or body structures include, but are not necessarily limited to, vascular tissue, brain, nervous tissue, esophagus, fallopian tube, heart, intestines, gallbladder, kidney, liver, lung, ovaries, pancreas, prostate, bladder, bone, spinal cord, spleen, stomach, testes, thymus, thyroid, trachea, ureter, urethra, uterus, and skin.

The repair and regeneration of tissue can be enhanced by supplying bioactive molecules such as growth factors, cell adhesion molecules, integrins, etc. with the self-assembling peptides and pharmaceutical compositions. In some embodiments, the bioactive molecules are present in the pharmaceutical composition. In some embodiments, cells that produce one or more bioactive molecules are present in the pharmaceutical composition. For example, genetically-modified, cells that produce and/or secrete one or more bioactive molecules may be present in the pharmaceutical composition.

The self-assembling peptides and pharmaceutical compositions described herein may be used to promote the regeneration or repair of ocular tissue (e.g., an optic nerve, corneal stromal layer and lens cortex). For example, the self-assembling peptides and pharmaceutical compositions described herein may be used to treat a subject having a retinopathy or a retinal/macular disorder.

In some embodiments, the self-assembling peptides and pharmaceutical compositions described herein may be used to promote or enhance repair or regeneration of neural tissue at a site of injury in a subject. For example, when administered to a site of injury, the pharmaceutical compositions described herein provide an environment that is permissive for the repair or regeneration of neural tissue and axon growth at the site of injury.

3. Wound Healing and Anti-Microbial Dressing

The self-assembling peptides and pharmaceutical compositions described herein may be used to promote wound healing or skin reconstruction or treat a wound (e.g., a burn) in a subject in need thereof. For example, the pharmaceutical compositions described herein may be directly applied to a wound or may be adapted for use with a gauze or a sheet in order to promote healing of the wound, promote skin reconstruction, or treat the wound. For example, in some embodiments, the pharmaceutical compositions described herein may be injected into biopsy sites or wound sites created by a surgical intervention (e.g., removal of a tumor). The pharmaceutical compositions described herein may also be used to facilitate healing in chronic wounds, such as skin lesions and diabetic ulcers. Methods for promoting wound healing or skin reconstruction and for treating wounds using self-assembling peptides are known in the art and can be adapted for use with the self-assembling peptides and pharmaceutical compositions described herein (see, e.g., U.S. Publication No. 2011/0002880, and International Publication No. WO 2017/210416, the entire contents of each of which are expressly incorporated herein by reference).

In some embodiments, the self-assembling peptides and pharmaceutical compositions described herein may be used as anti-microbial agents. In some embodiments, the self-assembling peptides and pharmaceutical compositions described herein may be used as an anti-microbial dressing.

4. Hemostasis

The self-assembling peptides and pharmaceutical compositions described herein may be used to promoted hemostasis in a subject. The self-assembling peptides and pharmaceutical compositions described herein may be used to stop or control blood loss from vessels (e.g., an artery, a vein, an aorta) and organs of the body of a subject (e.g., during surgery or after a traumatic injury). Methods for promoting hemostasis in a subject are known in the art and may be adapted for use with the self-assembling peptides and pharmaceutical compositions described herein (see, e.g., International Publication No. WO2017/210421, the entire contents of which are expressly incorporated herein by reference).

In some embodiments, the self-assembling peptides and pharmaceutical compositions described herein may be used to create a physical barrier to stop or prevent bleeding during a surgical or endoscopic procedures (e.g., during a hepatectomy, a splenectomy, a vaginoplasty, a cholecystectomy, a coronary bypass, or a femoral bypass). In some embodiments, the self-assembling peptides and pharmaceutical compositions described herein may be used to stop or prevent exudative hemorrhage from blood vessels and parenchyma of solid organs. In some embodiments, the self-assembling peptides and pharmaceutical compositions described herein may be used to stop or prevent exudative hemorrhage from vascular anastomosis (e.g. anastomosis to a native or artificial vessel). In some embodiments, the self-assembling peptides and pharmaceutical compositions described herein may be used to stop or prevent exudative hemorrhage from a small vessel or capillary vessel of the gastrointestinal tract of a subject (e.g., during an endoscopic sub-mucosal dissection (EMD) of the gastrointestinal tract, a laparoscopic resection of the gastrointestinal tract, or an endoscopic mucosal resection (EMR) of the gastrointestinal tract.

5. Local Drug/Therapeutic Agent Delivery

In one aspect, the present disclosure provides a combination composition comprising (i) self-assembling peptides comprising a self-assembling peptide or pharmaceutical composition described herein, and (ii) one or more payload agents (e.g., therapeutic agents), wherein a combination composition has a storage modulus of about 0.1 to about 100 Pa (e.g., at 5 rad/sec of frequency and 0.1 Pa of oscillation stress), and/or the combination composition has a viscosity in the range of about 0.5 Pa to about 50,000 Pa at room temperature. In some embodiments, one or more payload agents (e.g., therapeutic agents) of a combination composition are distributed substantially homogeneously within the combination composition.

In another aspect, the self-assembling peptides and pharmaceutical compositions described herein may be used for local delivery of drugs and/or therapeutic agents to diseased and/or defected sites in the body. Drugs/therapeutics can be mixed with peptide solution and injected using a needle, nozzle, or catheter. Drugs can be delivered and localized in the tissue, and then can be slowly released before hydrogel is absorbed in the body.

The term "agent" as used herein refers to a compound or entity of any chemical class including, for example, polypeptides, nucleic acids, saccharides, lipids, small molecules, metals, or combinations thereof. In some embodiments, an agent is or comprises a natural product in that it is found in and/or is obtained from nature. In some embodiments, an agent is or comprises one or more entities that are man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention comprise small molecules, antibodies, antibody fragments, aptamers, nucleic acids (e.g., siRNAs, shRNAs, DNA/RNA hybrids, antisense oligonucleotides, mRNA, CRISPR systems, and ribozymes), peptides, peptide mimetics, etc. In some embodiments, the agent is or comprises a polymer. In some embodiments, the agent is not a polymer and/or is substantially free of any polymer. In some embodiments, the agent contains at least one polymeric moiety. In some embodiments, the agent lacks or is substantially free of any polymeric moiety. In some embodiments, the agent is a cell and/or tissue. In some embodiments, the agent is or comprises a cellular lysate. In some embodiments, the agent is or comprises cellular material and/or multi-cellular material (e.g., micro-column grafts and/or micro-grafts).

As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

In some particular embodiments, combination compositions of the invention comprise one or more payload agents, e.g., therapeutic agents or detection agents. Such agents comprise, e.g., a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is or comprises a natural product in that it is found in and/or is obtained from nature. In some embodiments, an agent is or comprises one or more entities that are man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention comprise small molecules (e.g. antibiotics, anticancer drugs, antipain drugs, antiinflammatory drugs, steroids, anti-psychotics), antibodies, antibody fragments, aptamers, nucleic acids (e.g., siRNAs, shRNAs, DNA/RNA hybrids, antisense oligonucleotides, ribozymes), peptides, peptide mimetics, proteins, fusion proteins, vaccines, anti-coagulants, cytokines, hormones, enzymes, blood factors, extracellular matrix components, etc. In some embodiments, an agent may be selected from the group consisting of micrograft tissue, drugs (e.g., antibiotics), and biologies (e.g., growth factors and/or other molecules/proteins). In some embodiments, an agent is a cytokine (e.g., epidermal growth factor, nerve growth factor, transforming growth factor-alpha and beta, platelet-derived growth factor, insulin-like growth factor, vascular endothelial growth factor).

In some embodiments, a self-assembling peptide or pharmaceutical composition described herein combined with one or more payload agents (e.g., therapeutic agents) is used to treat a disease or disorder, e.g., a disease or disorder known to be or suspected to be treated by a therapeutic agent described herein (e.g., infection, cancer, cardiovascular disease, neurological disease), and/or used in wound-healing, bone/cartilage repair/regeneration, soft tissue regeneration. A self-assembling peptide or pharmaceutical composition described herein combined with one or more payload agents (e.g., therapeutic agents) can be administered to a subject in a variety of ways, and administration is not limited to any particular method. In some embodiments, a self-assembling peptide or pharmaceutical composition described herein combined with one or more payload agents (e.g., therapeutic agents) is administered to a subject by, or is applied to, a device, medical device, implant, dental implant, breast implant, prosthesis, needle, stent, or catheter. Additional methods of administration are described in, e.g., Patent Application Nos. U52011-0002880; WO/2008/073395; US2011/0201541; US 2014-0329914; US 2015-0105336; WO/2014/136081; WO/2014/141143, and U.S. Pat. No. 7,846,891, each of which are herein incorporated by reference in their entirety for any and all purposes.

Additional methods and embodiments can be found in WO 2017/120092, which is herein incorporated by reference in its entirety for any and all purposes.

6. Air Leakage Occlusion

In some embodiments, the self-assembling peptides and pharmaceutical compositions described herein may be used for air leakage occlusion. In some embodiments, the self-assembling peptides and pharmaceutical compositions described herein may be used for treating a pulmonary bulla. In embodiments, a method of treating a pulmonary bulla and/or an air leakage in a subject is provided. The method may comprise introducing a delivery device to a target area of the pulmonary bulla of the subject. The method may also comprise positioning an end of the delivery device in the target area in which treatment of a pulmonary bulla is desired. The method may also comprise administering through the delivery device a solution comprising a self-assembling peptide or pharmaceutical composition described here in an effective amount and in an effective concentration to the target area to form a barrier under physiological conditions of the target area to treat the pulmonary bulla. The method may also comprise removing the delivery device from the target area.

Additional methods and embodiments can be found in WO 2013/030673, WO 2015/138473, U.S. Pat. No. 10,245,299, each of which are herein incorporated by reference in their entirety for any and all purposes.

7. Prevention and Reduction of Adhesion

In some embodiments, the self-assembling peptides and pharmaceutical compositions described herein may be used for preventing or mitigating biological tissue adhesion. In various embodiments, the invention provides a method for mitigating adhesion to a biological tissue, the method comprising administering an effective amount of the self-assembling peptides and pharmaceutical compositions described herein to the biological tissue, wherein the self-assembling peptides and pharmaceutical compositions described herein mitigates adhesion to the biological tissue.

In various aspects, the invention provides a method of promoting anti-adhesion, comprising: introducing a delivery device to a target area; positioning an end of the delivery device in the target area at which anti-adhesion is desired; administering through the delivery device a solution comprising a self-assembling peptide or pharmaceutical composition decribed herein in an effective amount and in an effective concentration to the target area to promote anti-adhesion; and removing the delivery device from the target area.

In some embodiments the biological tissue comprises an epicardium, intraperitoneum, cecum, intestine, preferentially large intestine, and/or colon. In some embodiments, the target area comprises an epicardium, intraperitoneum, cecum, intestine, preferentially large intestine, and/or colon.

Additional methods and embodiments can be found in US 2019-0091376 A1, which is herein incorporated by reference in its entirety for any and all purposes.

8. In Vitro Cell Culture

In some embodiments, the self-assembling peptides and pharmaceutical compositions described herein may be used for 2D cell culture and/or 3D cell culture.

9. Bone Void Filler

In some embodiments, the self-assembling peptides and pharmaceutical compositions described herein may be used for filling a bone void.

In some embodiments, a method of filling a bone void in a subject is provided. In some embodiments, the method may involve introducing a delivery device to a bone of a subject, positioning an end of the delivery device proximate a void in the bone where promotion of bone growth is desired, administering through the delivery device a solution comprising a self-assembling peptide or pharmaceutical composition of the disclosure in an effective amount and in a concentration in a range of about 0.1 w/v percent to about 5 w/v percent peptide to form a hydrogel scaffold under physiological conditions to promote bone growth at the target site, and removing the delivery device from the subject.

In one or more embodiments, the self-assembling peptides and pharmaceutical compositions described herein may be used as a bone void filler (BVF) that resorbs and is replaced with bone during a healing process following administration at a target site. The peptide hydrogel may be placed into bony voids or gaps of the skeletal system. In certain embodiments, self-assembling peptides and self-assembled structures thereof may be used as cell culture supports for the repair and replacement of various tissues and as a scaffold to encapsulate living cells. The self-assembling peptides and pharmaceutical compositions described herein may promote tissue regeneration and the production of related extracellular matrix proteins. In at least some embodiments, the self-assembling peptides and pharmaceutical compositions described herein are non-immunogenic and represents an improvement over existing materials for this indication, including demineralized freeze-dried bone allograft (DFDBA) preparations.

Additional methods and embodiments can be found in US 2017-0128622 A1, which is herein incorporated by reference in its entirety for any and all purposes.

10. Artificial tears for Dry Eye

In some embodiments, the self-assembling peptides and pharmaceutical compositions described herein may be used to treat dry eye. In some embodiments, the self-assembling peptides and pharmaceutical compositions described herein may be used for artificial tears.

11. Articular Cartilage Repair

In some embodiments, the self-assembling peptides and pharmaceutical compositions described herein may be used to repair articular cartilage. In some embodiments, the self-assembling peptides and pharmaceutical compositions described herein may be used as an injectable composition. Without being bound by theory, injectable hydrogels comprising the self-assembling peptides and pharmaceutical compositions described herein can enhance its therapeutic efficacy and improve its ease of administration. An ideal injectable scaffold for cartilage regeneration should typically meet the following criteria: (i) ease of administration under physiological conditions, (ii) guaranteed injectability (gelation upon injection via either chemical or physical cross-linking), (iii) excellent biocompatibility and potential biodegradability, (iv) the ability to mimic cartilaginous ECM features and promote chondrogenic potential of cells, (v) the ability to easily fill defect sites inside the joint and integrate with the surrounding native cartilage tissue rather than shifting readily and (vi) a sustained release profile if associated with local drug delivery.

12. Cosmetic use (a Dermal Filler in Cosmetic Surgery)

In some embodiments, the self-assembling peptides and pharmaceutical compositions described herein may be used as a dermal filler. In some embodiments, the self-assembling peptides and pharmaceutical compositions described herein may be used as an injectable composition. Without being bound by theory, injectable hydrogels comprising the self-assembling peptides and pharmaceutical compositions described herein can enhance its therapeutic efficacy and improve its ease of administration. An ideal injectable scaffold for cartilage regeneration should typically meet the following criteria: (i) ease of administration under physiological conditions, (ii) guaranteed injectability (gelation upon injection via either chemical or physical cross-linking), (iii) excellent biocompatibility and potential biodegradability, (iv) the ability to mimic cartilaginous ECM features and promote chondrogenic potential of cells, (v) the ability to easily fill defect sites inside the joint and integrate with the surrounding native cartilage tissue rather than shifting readily and (vi) a sustained release profile if associated with local drug delivery.

In some embodiments, the self-assembling peptides and pharmaceutical compositions described herein may be used to plump lips. In some embodiments, the self-assembling peptides and pharmaceutical compositions described herein may be used to fill or smooth wrinkles. In some embodiments, the self-assembling peptides and pharmaceutical compositions described herein may be used soften facial creases. In some embodiments, the self-assembling peptides and pharmaceutical compositions described herein may be used to enhance shallow contours. In some embodiments, the self-assembling peptides and pharmaceutical compositions described herein may be used to reconstruct contour deformities in the face of a subject. In some embodiments, the self-assembling peptides and pharmaceutical compositions described herein may be used to improve the appearance of recessed scars. In some embodiments, the self-assembling peptides and pharmaceutical compositions described herein may be used to decrease or remove the shadow beneath the lower eye lids.

Kits

In another aspect, the disclosure provides kits and articles of manufacture comprising the pharmaceutical compositions and/or the self-assembling peptides described herein. The kits may include directions for the appropriate preparation and/or use of the components therein. The kits may further include useful tools for preparation and/or delivery of the pharmaceutical compositions or self-assembling peptides to subject (e.g., a human subject), as described herein.

In some embodiments, the kit contains separate containers, dividers or compartments for the pharmaceutical composition and informational material. For example, the pharmaceutical composition can be contained in a bottle, vial, or syringe, and the informational material can be contained in a plastic sleeve or packet. In some embodiments, the separate elements of the kit are contained within a single, undivided container. For example, the pharmaceutical composition or self-assembling peptide may be contained in a bottle, vial or syringe that has attached thereto the informational material in the form of a label.

In some embodiments, the kit comprises a plurality, e.g., a pack, of individual containers, each containing one or more unit dosage forms of the pharmaceutical composition or self-assembling peptide. For example, the kit may comprise a plurality of syringes, ampules, foil packets, or blister packs, each containing a single unit dose of the pharmaceutical composition or self-assembling peptide. In some embodiments, a component of the kit is stored in a sealed vial, for example, with a rubber or silicone closure (for example, a polybutadiene or polyisoprene closure). In some embodiments, a component of the kit is stored under inert conditions (for example, under nitrogen or another inert gas such as argon). In some embodiments, a component of the kit is stored under anhydrous conditions (for example, with a desiccant). In some embodiments, a component of the kit is stored in a light blocking container such as an amber vial. In some embodiments, the containers of the kits can be air tight and/or waterproof.

The kits may further comprise solutions including tonicity agents. These solutions may be packaged separately, or in combination with, pharmaceutical compositions comprising a self-assembling peptide provided herein.

Articles of manufacture, including for example, syringes, auto-injectors, tubing, and catheters (e.g., with or without a guidewire) are also provided. In some embodiments, the articles of manufacture may be pre-filled with a self-assembling peptide, or pharmaceutical composition described herein. These articles of manufacture may be separate from or included in a kit described herein.

Further aspects and embodiments of the present invention are set out in the following numbered paragraphs:

1. A pharmaceutical composition comprising a self-assembling peptide, wherein the self-assembling peptide comprises an amino acid sequence as set forth in:

$$[(X)i(Y)j(Z)k(Y)l]m(X)n \qquad \text{Formula I,}$$

$$[(Y)i(X)j(Y)k(Z)l]m(Y)n \qquad \text{Formula II,}$$

[(Z)i(Y)j(X)k(Y)l]m(Z)n    Formula or

[(Y)i (Z)j(Y)k(X)l]m (Y)n    Formula IV, wherein each (X) is independently an ionic, polar amino acid, wherein each (Y) is independently a hydrophobic amino acid, wherein each (Z) is independently a non-ionic, polar amino acid, wherein each i, j, k, and l is independently an integer≥1, wherein m is an integer≥2, and wherein n=0 or an integer≥1.

2. The pharmaceutical composition of paragraph 1, wherein e self assembling peptide comprises an amino acid sequence as set forth in Formula I.

3. The pharmaceutical composition of paragraph 1, wherein the self-assembling peptide comprises an amino acid sequence as set forth in Formula II.

4. The pharmaceutical composition of paragraph 1, wherein the self-assembling peptide comprises an amino acid sequence as set forth in Formula 5. The pharmaceutical composition of paragraph 1, wherein the self-assembling peptide comprises an amino acid sequence as set forth in Formula IV.

6. The pharmaceutical composition of any one of paragraphs 1-5, wherein each (X) is a basic amino acid.

7. The pharmaceutical composition of paragraph 6, wherein the basic amino acid is selected from the group consisting of arginine, lysine, histidine and ornithine.

8. The peptide of any one of paragraphs 1-5, wherein each (X) is an acidic amino acid.

9. The peptide of paragraph 8, wherein the acidic amino acid is selected from the group consisting of aspartic acid and glutamic acid.

10. The pharmaceutical composition of any one of paragraphs 1-9, wherein each (Y) is selected from the group consisting of alanine, valine, leucine, isoleucine, methionine, phenylalanine, tryptophan, and glycine.

11. The pharmaceutical composition of any one of paragraphs 1-10, wherein each (Z) is selected from the group consisting of the group consisting of serine, threonine, tyrosine, cysteine, glutamine, asparagine, and methionine.

12. The pharmaceutical composition of any one paragraphs 1-11, wherein at least one of j, k, and l is independently an integer of 1.

13. The pharmaceutical composition of any one of paragraphs 1-12, wherein at least one of i, j, k, and l is independently an integer of 2.

14. The pharmaceutical composition of any one of paragraphs 1-13, wherein m is independently an integer of 2 or 3.

15. The pharmaceutical composition of any one of paragraphs 1-14, wherein the self-assembling peptide comprises an amino acid sequence as set forth in SEQ ID NOs: 1-20.

16. The pharmaceutical composition of any one of paragraphs 1-15, wherein the self-assembling peptide comprises an N-terminal functional group, a C-terminal functional group, or both.

17. The pharmaceutical composition of paragraph 16, wherein the N-terminal functional group is selected from the group consisting of an acetyl, a formyl., pyroglutamyl (pGlu), biotin, polyethylene glycol (PEG), urea, alkylamine, a carbamate, a sulfonamide, dansyl, 2,4-dintrophenyl, fluorescein, 7-methoxycoumarin acetic acid, 9-fluorenylmethyloxycarbonyl, palmitic acid, succinyl, chloroacetyl, maleimide, benzyloxycarbonyl, bromoacetyl, nitrilotriacetyl, tertbutoxycarbonyl, 4-hydroxyphenylpropionic acid, allyloxycarbonyl, butyric acid, a fatty acid, and trityl.

18. The pharmaceutical composition of paragraph 16, wherein the C-terminal functional group is selected from the group consisting of an amido, an N-alkyl amide, an aldehyde, an ester an alcohol, para-nitroanilide (pNA), 7-amino-4-methylcoumarin (Amc), a hydrazide, hydroxamic acid, chloromethylketone, p-nitroaniline, para-nitrophenol, hydroxysucinimide ester, fluoromethylketone, cysteamine, 9-fluorenemethyl (Fm) ester, allyl ester, 2,4-dimethoxybenzyl ester, 2-phenylisopropyl ester, p-nitrobenzyl ester, and 2-chlorotrityl ester.

19. The pharmaceutical composition of any one of paragraphs 1-16, wherein the self-assembling peptide comprises an amino acid sequence as set forth in SEQ ID NOs: 21-40.

20. The pharmaceutical composition of any one of paragraphs 1-19, wherein the self-assembling peptide further comprises at least one biologically-active peptide motif.

21. The pharmaceutical composition of any one of paragraphs 1-20. wherein the at least one biologically-active peptide motif is present at the N-terminal end of the self-assembling peptide.

22. The pharmaceutical composition of any one of paragraphs 1-20, wherein the at least one biologically-active peptide motif is present at the C-terminal end of the self-assembling peptide.

23. The pharmaceutical composition of any one of paragraphs 20-22, wherein the at least one biologically-active peptide motif is derived from laminin-1, collagen IV, fibronectin, elastin, bone marrow homing peptide 1, bone marrow homing peptide 2, or myelopeptide.

24. The pharmaceutical composition of any one of paragraphs 20-22, wherein the at least one biologically-active peptide motif comprises an amino acid sequence as set forth in any one of SEQ ID NOs: 41-70.

25. The pharmaceutical composition of any one of paragraphs 1-20, wherein the self-assembling peptide comprises an amino acid sequence as set forth in SEQ NOs: 71-90.

26. The pharmaceutical composition of any one of paragraphs 1-25, further comprising a tonicity agent.

27. The pharmaceutical composition of paragraph 26, wherein the tonicity agent is present at a concentration of about 0.01 M to about 0.3 M.

28. The pharmaceutical composition of paragraph 26, wherein the tonicity agent is present at a concentration of about 0.15 M.

29. The pharmaceutical composition of any one of paragraphs 1-28, having a pH of from about 6 to about 8.

30. The pharmaceutical composition of any one of paragraphs 1-28, having a pH of from about 7 to about 7.5.

31. The pharmaceutical composition of paragraph 29 or paragraph 30, wherein the net charge of the self-assembling peptide is greater than or equal to +1 or less than or equal to −1.

32. The pharmaceutical composition of paragraph 29 or paragraph 30, wherein the net charge of the self-assembling peptide is from about +1 to about +6.

33. The pharmaceutical composition of paragraph 29 or paragraph 30, wherein the net charge of the self-assembling peptide is from about −1 to about −6, 34. The pharmaceutical composition of any one of paragraphs 1-33, wherein the concentration of the self-assembling peptide from about 0.01% (w/v) to about 10% (w/v).

35. The pharmaceutical composition of any one of paragraphs 1-33, wherein the concentration of the self-assembling peptide is from about 0.1% (w/v) to about 5% (w/v).

36. The pharmaceutical composition of any one of paragraphs 1-33, wherein the concentration of the self-assembling peptide is from about 0.5% (w/v) to about 1.5% (w/v).

37. The pharmaceutical composition of any one of paragraphs 1-33, wherein the concentration of the self-assembling peptide is about 1% w/v).

38. The pharmaceutical composition of any one of paragraphs 1-37. further comprising an isolated cell.

39. The pharmaceutical composition of paragraph 38, wherein the isolated cell is a mammalian cell.

40. The pharmaceutical composition of paragraph 38 or paragraph 39, wherein the mammalian cell is an immune cell, a stem cell, chondrocyte progenitor cells, pancreatic progenitor cells, myoblasts, fibroblasts, keratinocytes, neuronal cells, glial cells, astrocytes, pre-adipocytes, adipocytes, vascular endothelial cells, endothelial progenitor cells, mesenchymal cells, neural stem cells, immune cells, (e.g., B-cells and T-cells), smooth muscle progenitor cells, cardiac myocytes, fetal dermal fibroblasts, epidermal keratinocytes, myoblasts, and capillary endothelial cells.

41. The pharmaceutical composition of any one of paragraphs 1-40, wherein the pharmaceutical composition further comprises a bioactive agent.

42. The pharmaceutical composition of paragraph 41, wherein the bioactive agent is selected from the group consisting of a hormone, a growth factor, insulin, an enzyme, an siRNA, an shRNA, an antisense-RNA, an antibiotic, an antibody, and an anti-inflammatory agent.

43. The pharmaceutical composition of any one of paragraphs 1-42, wherein the pharmaceutical composition is an aqueous solution.

44. The pharmaceutical composition of any one of paragraphs 1-42, wherein the pharmaceutical composition is a hydrogel.

45. The pharmaceutical composition of paragraph 44, wherein the pharmaceutical composition is a hydrogel, and wherein the hydrogel comprises a storage modulus of at least about 10 Pascal (Pa).

46. An article of manufacture comprising the pharmaceutical composition of any one of paragraphs 1-45.

47. The article of manufacture of paragraph 46, wherein the article is a syringe, a vial, an auto-injector tubing, or a catheter.

48. A method of treating a subject in need thereof, comprising administering an effective amount of the pharmaceutical composition according to any one of paragraphs 1-45 to the subject.

49. A method of promoting tissue repair or regeneration in a subject in need thereof, comprising contacting a tissue of the subject with the pharmaceutical composition according to any one of paragraphs 1-45, thereby promoting tissue repair or regeneration of the tissue.

50. The method of paragraph 49, wherein the tissue is skin, bone, cartilage, neural tissue, ligament, tendon, vascular tissue, or muscle.

51. The method of paragraph 49, wherein the tissue is optic tissue.

52. The method of paragraph 49, wherein the tissue is cardiac tissue.

53. The method of any one of paragraphs 49-52, wherein the subject has a congenital disease or disorder resulting in a need for the tissue repair or regeneration.

54. The method of any one of paragraphs 49-52, wherein the subject has suffered an injury resulting in a need for the tissue repair or regeneration.

55. The method of paragraph 54, wherein the injury is a result of surgery, trauma, stroke, tumor, or a disease or disorder, 56. A method of promoting wound healing in a subject in need thereof, comprising contacting a wound of the subject with the pharmaceutical composition according to any one of paragraphs 1-45, thereby promoting wound healing.

57. The method of paragraph 56, wherein the wound comprises an abrasion, a burn, a chap, a detrition, a cut, an ulcer, a laceration, an incision, or a scratch.

58. A method of stopping or preventing a bleeding at a site within a subject, comprising contacting the site with the pharmaceutical composition according to any one of paragraphs 1-45, wherein the pharmaceutical composition creates a physical barrier thereby stopping or preventing bleeding at the site within the subject.

59. A method of excising a lesion from a site in the gastrointestinal tract of a subject, comprising:
a. contacting submucosa below the lesion with a pharmaceutical composition according to any one of paragraphs 1-45, thereby lifting the lesion; and
b. excising the lesion from the site in the gastrointestinal tract of the subject.

60. The method of paragraph 59, wherein the lesion comprises a polyp, an ulcer, or a tumor.

61. The method of paragraph 59 or paragraph 60, wherein the lesion is present in a region of the gastrointestinal tract of the subject selected from a mouth, a throat, an esophagus, a stomach, a small intestine, a large intestine, a colon, and a rectum.

62. A method of culturing a cell, comprising contacting the cell with the pharmaceutical composition according to any one of paragraphs 1-45.

The following examples are illustrative and not restrictive. Many variations of the technology will become apparent to those of skill in the art upon review of this disclosure. The scope of the technology should, therefore, be determined not with reference to the examples, but instead should be determined with reference to the appended claims along with their full scope of equivalents.

EXAMPLES

Materials and Methods

The following materials and methods were utilized to conduct the experiments described in the Examples below.
Peptide Synthesis All peptides utilized in the Examples herein were synthesized by conventional solid peptide synthesis using an automated peptide synthesizer.
Viscosity Determination Peptides formulated as aqueous solutions (200 µL), were placed between the plates of a rheometer (DHR-1, TA Instruments, 20 mm plates at a measuring geometry of 500 µm) and the viscosity was measured from $0.001$ $s^{-1}$ to $100$ $s^{-1}$ shear rate. Thixotropic Measurements Peptides formulated as aqueous solutions (200 µL), were placed between the plates of a rheometer (DHR-1, TA Instruments, 20 mm plates at a measuring geometry of 500 µm) and the sample was exposed to a fast plate rotation at $1000$ $s^{-1}$ of shear rate for 1 minute and the storage modulus was measured at 1 rad $s^{-1}$ angular frequency for 10 minutes.
Frequency Sweep Test Peptides formulated as aqueous solutions were placed between the plates of a rheometer (DHR-1, TA Instruments, 20 mm plates at a measuring geometry of 500 µm or 40 mm cone and plate at a measuring geometry of 2.0° of cone angle) and frequency stress sweep tests were performed at 0.1 Hz to 10 Hz of frequency with 0.1% of strain; measurements were performed after 2 minutes of relaxation time at 37° C. To do frequency sweep tests after exposure to Dulbecco's Modified Eagle Medium (DMEM), 10 mL of DMEM was added in chamber surrounding the plates, the sample in plates was submerged into the DMEM and the frequency test was performed as described after 20 minutes.

Endoscopic Mucosal Resection and Endoscopic Submucosal Dissection

An in vivo porcine animal model was used to perform endoscopic mucosal and submucosal dissections as described in Uraoka et al. (2009) Drug Des. Devel. Ther. 2:131-8, incorporated herein by reference. Briefly, 2 mL of select peptide formulations were injected in between the muscle and submucosal layer in stomach of a pig and the submucosa was dissected using electro-knife. The gross appearance of the injection site and of dissected submucosal tissues at the injection sites were analyzed.

Example 1

Determination of Net Charge of Exemplary Self-Assembling Peptides in Formulations at Varying pH Ranges Several exemplary self-assembling peptides described herein (Table 5; SEQ ID NO: 21-40) were designed to have a net charge, positive or negative, when formulated at pH 7.5. In contrast, previously-described self-assembling peptides have a net zero charge at the same pH. The net charges of the exemplary self-assembling peptides in solution at pH 7.5 was determined and is shown in Table 5. While the previously described self-assembling peptides RADA16, IEIK13, and KLD12 (SEQ ID NO: 91-93, respectively) have about zero net charge at pH 7.5, the newly developed self-assembling peptides had a net positive or net negative charge at the same pH.

Figure 1:
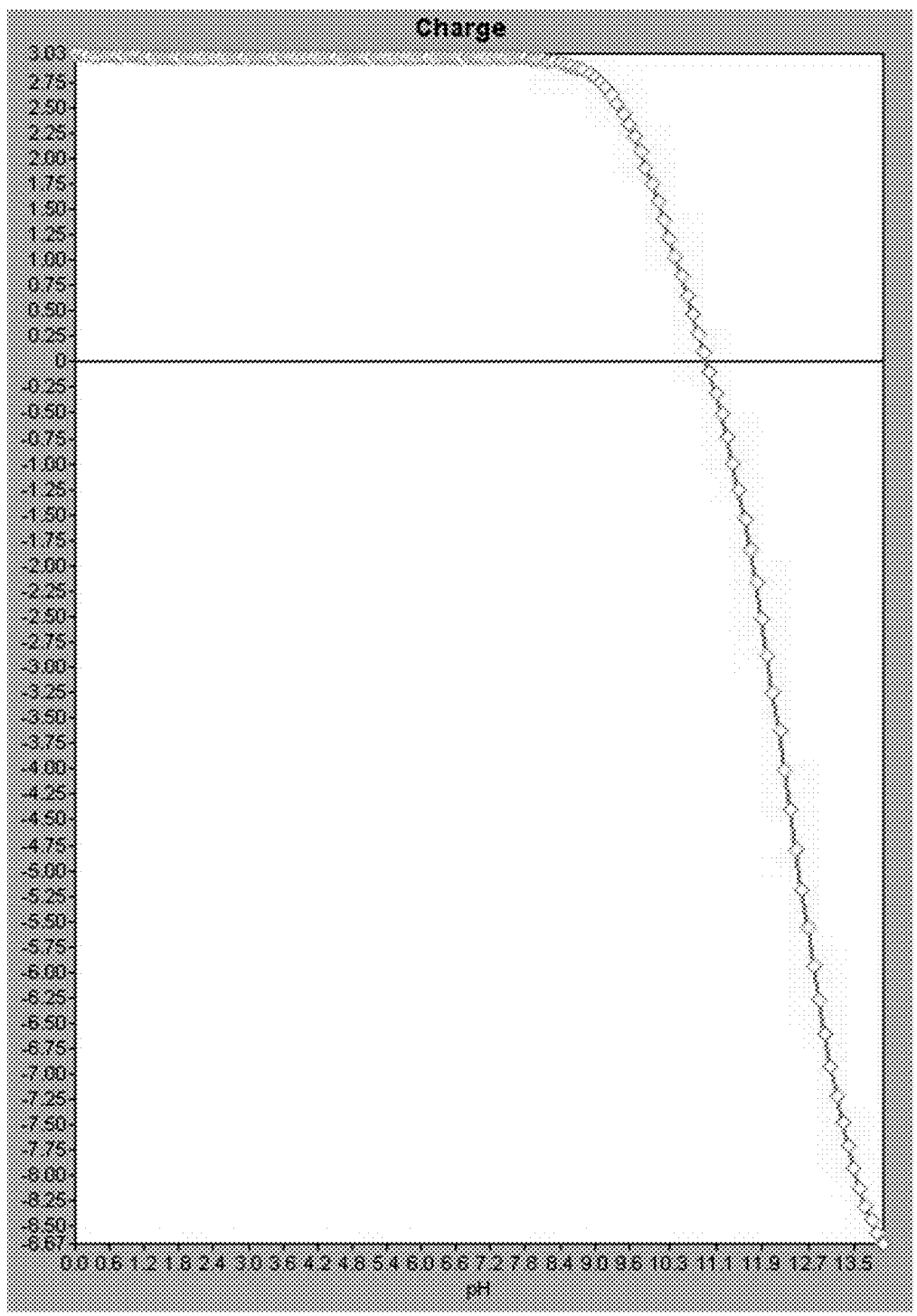
FIG. 1 shows net charge measurements of KLNL12 (SEQ ID NO: 21) at various pH.
Figure 2:
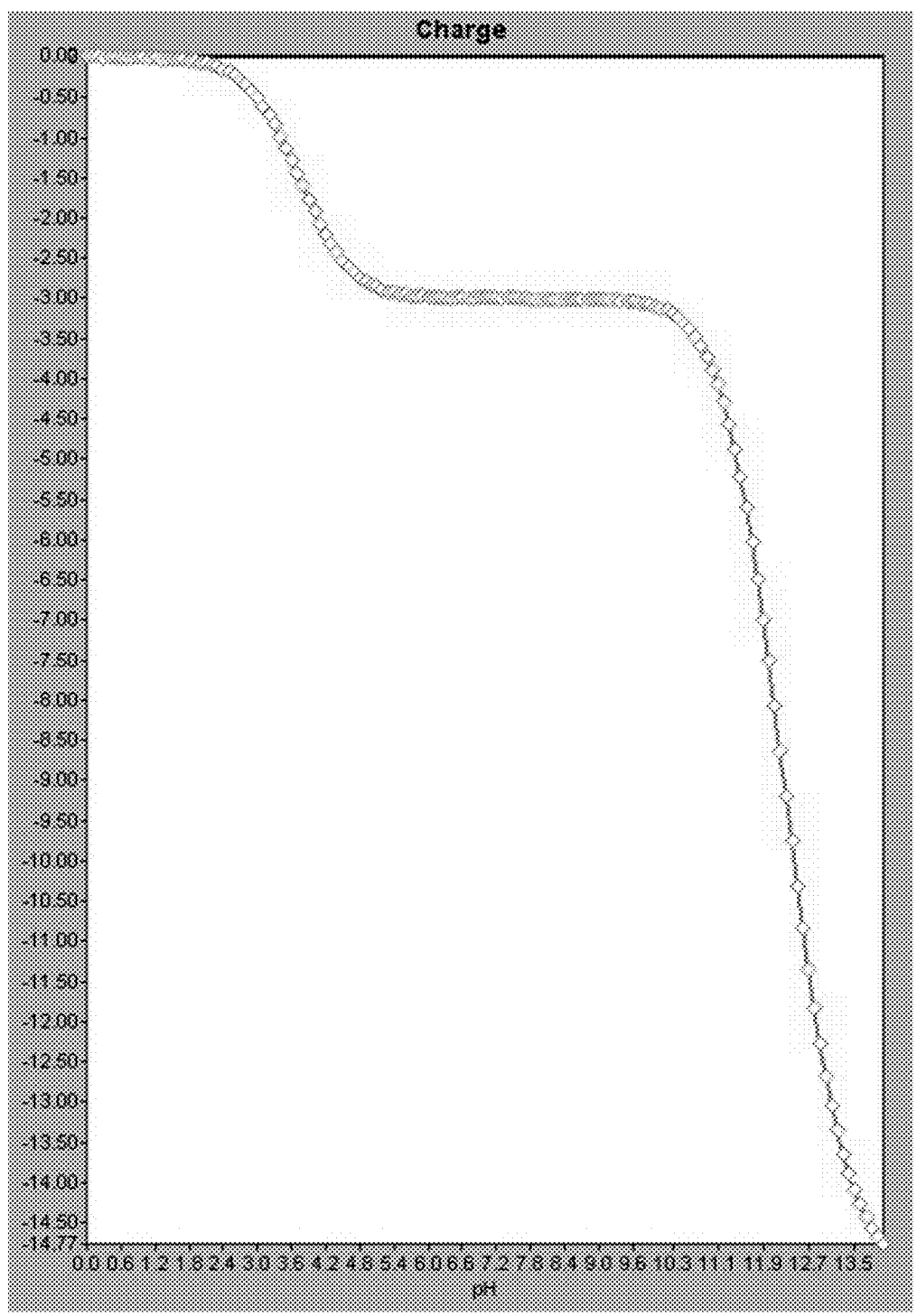
FIG. 2 shows net charge measurements of NLEL12 (SEQ ID NO: 33) at various pH.
Figure 3:
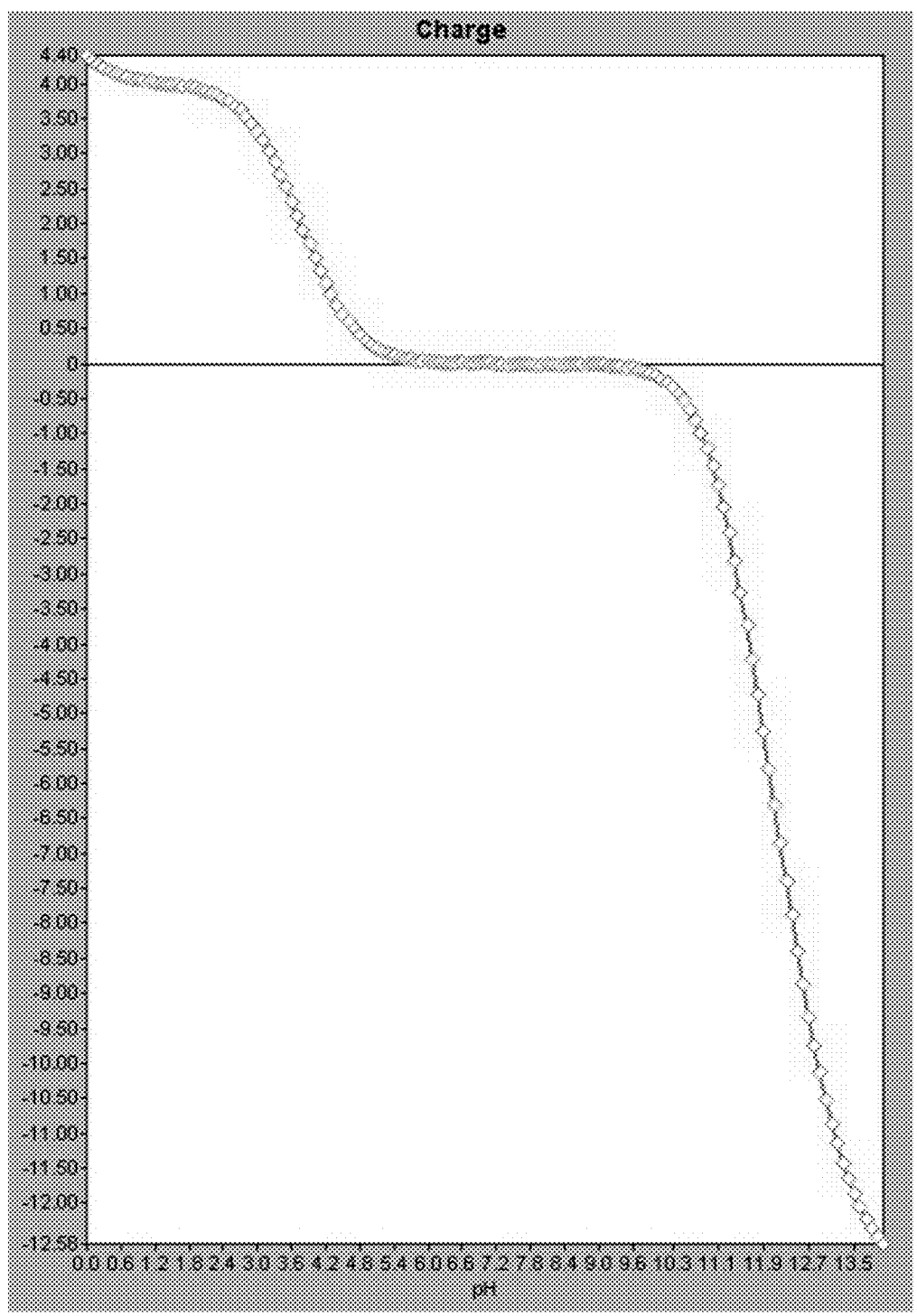
FIG. 3 shows net charge measurements of RADA16 (SEQ ID NO: 91) at various pH.

As shown in FIGS. 1-3, this net charge behavior extends around the test point of pH 7.5 shown in Table 5. For example, FIG. 1 shows net charge as a function of pH for KLNL12 (SEQ ID NO: 21, about +3 around neutral pH). FIG. 2 shows net charge as a function of pH for NLEL12 (SEQ ID NO: 33, about −3 around neutral pH). FIG. 3 shows net charge as a function of pH for RADA16 (SEQ ID NO: 91, about 0 around neutral pH).

TABLE 5

Net charge of exemplary self-assembling peptides at pH 7.5.

| Name | SEQ ID NO: | Sequence | Net charge at pH 7.5 |
|---|---|---|---|
| KLNL12 | 21 | Ac-KLNLKLNLKLNL-NH2 | +3 |
| LNLK12 | 22 | Ac-LNLKLNLKLNLK-NH2 | +3 |
| NLKL12 | 23 | Ac-NLKLNLKLNLKL-NH2 | +3 |
| LKLN12 | 24 | Ac-LKLNLKLNLKLN-NH2 | +3 |
| KLNL13 | 25 | Ac-KLNLKLNLKLNLK-NH2 | +4 |
| KLNL17 | 26 | Ac-KLNLKLNLKLNLKLNLK-NH2 | +5 |
| IQIK12 | 27 | Ac-IQIKIQIKIQIK-NH2 | +3 |
| IQIK13 | 28 | Ac-IQIKIQIKIQIKI-NH2 | +3 |
| KIQI13 | 29 | Ac-KIQIKIQIKIQIK-NH2 | +4 |
| QIKI13 | 30 | Ac-QIKIQIKIQIKIQ-NH2 | +3 |
| IKIQ13 | 31 | Ac-IKIQIKIQIKIQI-NH2 | +3 |

TABLE 5-continued

Net charge of exemplary self-assembling peptides at pH 7.5.

| Name | SEQ ID NO: | Sequence | Net charge at pH 7.5 |
|---|---|---|---|
| INIK13 | 32 | Ac-INIKINIKINIKI-NH2 | +3 |
| NLEL12 | 33 | Ac-NLELNLELNLEL-NH2 | −3 |
| NLDL12 | 34 | Ac-NLDLNLDLNLDL-NH2 | −3 |
| KANA12 | 37 | Ac-KANAKANAKANA-NH2 | +3 |
| KVNV12 | 38 | Ac-KVNVKVNVKVNV-NH2 | +3 |
| RANA16 | 39 | Ac-RANARANARANARANA-NH2 | +4 |
| KLTL12 | 40 | Ac-KLTLKLTLKLTL-NH2 | +3 |
| RADA16* | 91 | Ac-RADARADARADARADA-NH2 | 0 |
| IEIK13* | 92 | Ac-IEIKIEIKIEIKI-NH2 | 0 |
| KLDL12* | 93 | Ac-KLDLKLDLKLDL-NH2 | 0 |

*exemplary conventional self-assembling peptides for comparison

Figure 4:
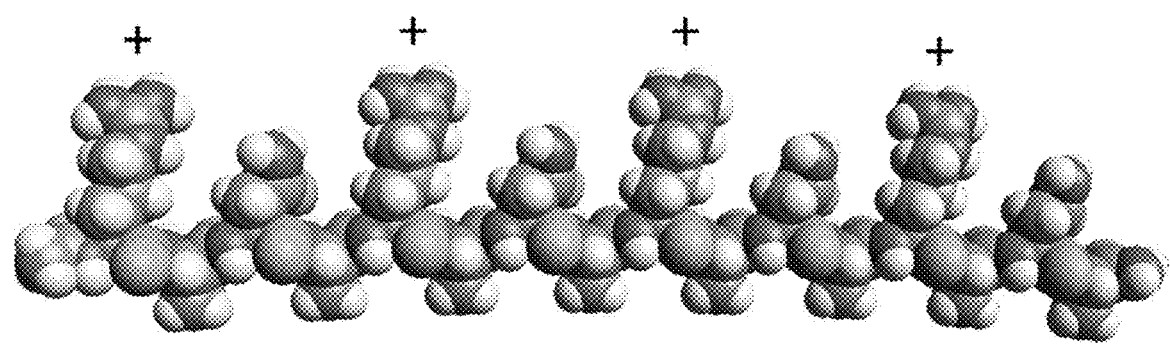
FIG. 4 shows a schematic representation of the molecular structure and the electronic charge of RANA16 (SEQ ID NO: 39) at pH 7.5.
Figure 5:
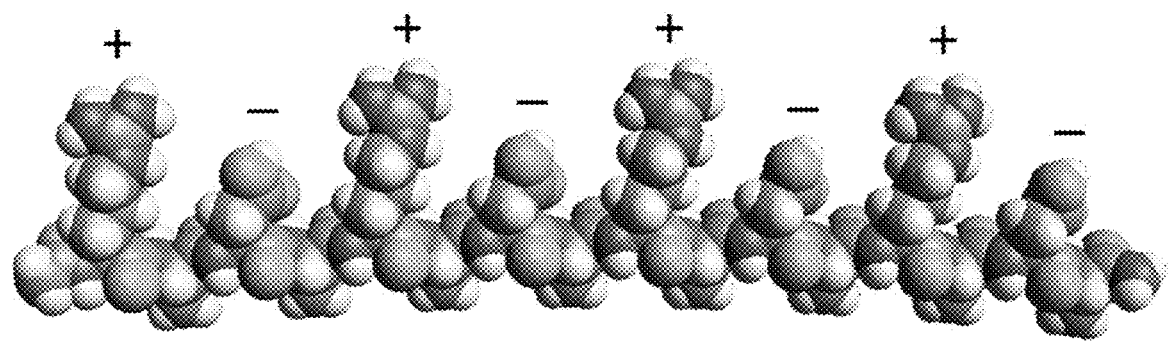
FIG. 5 shows a schematic representation of the molecular structure and the electronic charge of RADA16 (SEQ ID NO: 91) at pH 7.5.

FIGS. 4-5 provide molecular models of the atomic structure and net charge of exemplary self-assembling peptides. FIG. 4 shows that RANA16 (SEQ ID NO: 39) has a net charge of +4 at pH 7.5. In contrast, FIG. 5 shows that RADA16 (SEQ ID NO: 91) has a net charge of 0 at pH 7.5. The structures were computationally simulated using MarvinSketch and both exhibit β-sheet conformations. Despite RANA16 (SEQ ID NO: 39) and RADA 16 (SEQ ID NO: 91) exhibiting similar structural conformations at pH 7.5, the net charge of the two peptides is markedly different, with RANA16 (SEQ ID NO: 39) having a +4 net positive charge, while RADA16 (SEQ ID NO: 91) has zero net charge.

Example 2

Characterization of Solubility of Exemplary Self-Assembling Peptides in Aqueous Pharmaceutical Compositions Formulated at pH 2.5 and 7.5

Several exemplary self-assembling peptides described herein (see Table 5; SEQ ID NO: 21-40) were designed to: have a non-zero net charge, have high solubility when formulated in solution at pH 7.5, and transition from liquid state to hydrogel after administration (e.g., after injection into a subject or admixture with solutions containing specific concentrations of tonicity agents (e.g., salts)). In contrast, previously described self-assembling peptides RADA16, IEIK13, and KLDL12 (SEQ ID NO: 91-93, respectively) have a zero net charge and must be formulated in solution at acidic pH in order to retain their ability to conditionally transition from liquid state to hydrogel after administration.

To determine the solubility of exemplary self-assembling peptides in aqueous pharmaceutical compositions formulated at acidic and neutral pH, the appearance of the pharmaceutical compositions was assessed. Homogenous and transparent appearance reflects sufficient solubility of the peptides in solution and minimal hydrogel formation. Phase separation and cloudy appearance reflects poor solubility of the peptides in solution and/or the formation of hydrogel.

The appearance of exemplary self-assembling peptides at pH 2.5 and pH 7.5 is shown below in Table 6 and FIG. 20. Aqueous pharmaceutical compositions at pH 7.5 comprising the newly described self-assembling peptides were transparent and homogenous, while solutions of previously disclosed self-assembling peptides RADA16 (SEQ ID NO: 91), IEIK13 (SEQ ID NO: 92) and KLDL12 (SEQ ID NO: 93) at pH 7.5 exhibited phase separation and cloudy appearance (see Table 6 and FIGS. 20A-C).

Example 3

Characterization of Solubility of Aqueous Pharmaceutical Compositions Formulated at pH 7.5 and Varying Ionic Strengths The self-assembling peptides described herein (Table 5; SEQ ID NOs: 21-40) were designed to: have a non-zero net charge, have high solubility when formulated as aqueous

TABLE 6

Appearance of exemplary self-assembling peptides at pH 2.5 and pH 7.5.

| SEQ ID NO: | Name | Sequence | Appearance at different pH | |
|---|---|---|---|---|
| | | | At pH 2.5 | At pH 7.5 |
| 21 | KLNL12 | Ac-KLNLKLNLKLNL-NH2 | Homogeneous and transparent | Homogeneous and transparent |
| 22 | LNLK12 | Ac-LNLKLNLKLNLK-NH2 | Homogeneous and transparent | Homogeneous and transparent |
| 23 | NLKL12 | Ac-NLKLNLKLNLKL-NH2 | Homogeneous and transparent | Homogeneous and transparent |
| 24 | LKLN12 | Ac-LKLNLKLNLKLN-NH2 | Homogeneous and transparent | Homogeneous and transparent |
| 25 | KLNL13 | Ac-KLNLKLNLKLNLK-NH2 | Homogeneous and transparent | Homogeneous and transparent |
| 26 | KLNL17 | Ac-KLNLKLNLKLNLKLNLK-NH2 | Homogeneous and transparent | Homogeneous and transparent |
| 27 | IQIK12 | Ac-IQIKIQIKIQIK-NH2 | Homogeneous and transparent | Homogeneous and transparent |
| 28 | IQIK13 | Ac-IQIKIQIKIQIKI-NH2 | Homogeneous and transparent | Homogeneous and transparent |
| 29 | KIQI13 | Ac-KIQIKIQIKIQIK-NH2 | Homogeneous and transparent | Homogeneous and transparent |
| 32 | INIK13 | Ac-INIKINIKINIKI-NH2 | Homogeneous and transparent | Homogeneous and transparent |
| 33 | NLEL12 | Ac-NLELNLELNLEL-NH2 | Phase-separated and cloudy | Homogeneous and transparent |
| 34 | NLDL12 | Ac-NLDLNLDLNLDL-NH2 | Phase-separated and cloudy | Homogeneous and transparent |
| 35 | QLEL12 | Ac-QLELQLELQLEL-NH2 | Phase-separated and cloudy | Homogeneous and transparent |
| 36 | LELQ12 | Ac-LELQLELQLELQ-NH2 | Phase-separated and cloudy | Homogeneous and transparent |
| 91 | RADA16 | Ac-RADARADARADARADA-NH2 | Homogeneous and transparent | Phase-separated and cloudy |
| 92 | IEIK13 | Ac-IEIKIEIKIEIKI-NH2 | Homogeneous and transparent | Phase-separated and cloudy |
| 93 | KLDL12 | Ac-KLDLKLDLKLDL-NH2 | Homogeneous and transparent | Phase-separated and cloudy | solutions at pH 7.5 having isotonic ionic strength (e.g., 0.15 M salt ions), and to transition from liquid state to hydrogel after administration. To determine the solubility of aqueous pharmaceutical compositions formulated at pH 7.5 in the presence of varying ionic strengths, aqueous pharmaceutical compositions having different concentrations of sodium chloride were prepared, and their appearance assessed. Homogenous and transparent appearance reflects sufficient solubility of the peptides in solution and minimal hydrogel formation. Phase separation and cloudy appearance reflects poor solubility of the peptides in solution and/or the formation of hydrogel.

As shown in Table 7, in general, the increased amounts of hydrophobic residues correlated with decreased solubility at higher ionic strengths. Therefore, the amino acid composition of the self-assembling peptides can be manipulated to achieve desired solubility of at a desired ionic strength.

TABLE 7

Appearance of exemplary self-assembling peptides at different ionic strength.

| SEQ ID NO: | Name | Sequence | Appearance at different ionic strength (e.g., NaCl concentration) at around pH 7.5 | | | |
|---|---|---|---|---|---|---|
| | | | 0 M | 0.05 M | 0.1 M | 0.15 M (isotonic) |
| 21 | KLNL12 | Ac-KLNLKLNLKLNL-NH2 | Homogeneous and transparent | Homogeneous and transparent | Homogeneous and transparent | Homogeneous and transparent |
| 22 | LNLK12 | Ac-LNLKLNLKLNLK-NH2 | Homogeneous and transparent | Homogeneous and transparent | Phase-separated and cloudy | Phase-separated and cloudy |
| 23 | NLKL12 | Ac-NLKLNLKLNLKL-NH2 | Homogeneous and transparent | Homogeneous and transparent | Homogeneous and transparent | Homogeneous and transparent |
| 24 | LKLN12 | Ac-LKLNLKLNLKLN-NH2 | Homogeneous and transparent | Homogeneous and transparent | Phase-separated and cloudy | Phase-separated and cloudy |
| 25 | KLNL13 | Ac-KLNLKLNLKLNLK-NH2 | Homogeneous and transparent | Homogeneous and transparent | Homogeneous and transparent | Homogeneous and transparent |
| 26 | KLNL17 | Ac-KLNLKLNLKLNLKLNLK-NH2 | Homogeneous and transparent | Homogeneous and transparent | Homogeneous and transparent | Homogeneous and transparent |
| 27 | IQIK12 | Ac-IQIKIQIKIQIK-NH2 | Homogeneous and transparent | Homogeneous and transparent | Homogeneous and transparent | Homogeneous and transparent |
| 28 | IQIK13 | Ac-IQIKIQIKIQIKI-NH2 | Homogeneous and transparent | Phase-separated and cloudy | Phase-separated and cloudy | Phase-separated and cloudy |
| 29 | KIQI13 | Ac-KIQIKIQIKIQIK-NH2 | Homogeneous and transparent | Homogeneous and transparent | Homogeneous and transparent | Homogeneous and transparent |
| 32 | INIK13 | Ac-INIKINIKINIKI-NH2 | Homogeneous and transparent | Homogeneous and transparent | Phase-separated and cloudy | Phase-separated and cloudy |
| 33 | NLEL12 | Ac-NLELNLELNLEL-NH2 | Homogeneous and transparent | Homogeneous and transparent | Homogeneous and transparent | Homogeneous and transparent |
| 34 | NLDL12 | Ac-NLDLNLDLNLDL-NH2 | Homogeneous and transparent | Homogeneous and transparent | Homogeneous and transparent | Homogeneous and transparent |
| 35 | QLEL12 | Ac-QLELQLELQLEL-NH2 | Homogeneous and transparent | Homogeneous and transparent | Homogeneous and transparent | Homogeneous and transparent |
| 36 | LELQ12 | Ac-LELQLELQLELQ-NH2 | Homogeneous and transparent | Homogeneous and transparent | Homogeneous and transparent | Homogeneous and transparent |
| 91 | RADA16* | Ac-RADARADARADARADA-NH2 | Homogeneous and transparent | Homogeneous and transparent | Homogeneous and transparent | Homogeneous and transparent |

TABLE 7-continued

Appearance of exemplary self-assembling peptides at different ionic strength.

| SEQ ID NO: | Name | Sequence | Appearance at different ionic strength (e.g., NaCl concentration) at around pH 7.5 | | | |
|---|---|---|---|---|---|---|
| | | | 0 M | 0.05 M | 0.1 M | 0.15 M (isotonic) |
| 93 | KLDL12* | Ac-KLDLKLDLKLDL-NH2 | Homogeneous and transparent | Homogeneous and transparent | Homogeneous and transparent | Homogeneous and transparent |
| 92 | IEIK13* | Ac-IEIKIEIKIEIKI-NH2 | Homogeneous and transparent | Phase-separated and cloudy | Phase-separated and cloudy | Phase-separated and cloudy |

*peptides precipitate at around pH 7.5, and were therefore formulated at around pH 2.2-2.3

Example 4

Determination of Shear Thinning and Thixotropic Behavior of Aqueous Pharmaceutical Compositions Comprising Exemplary Self-Assembling Peptides Formulated at pH 7.5 at Varying Ionic Strengths The self-assembling peptides disclosed herein (Table 5 SEQ ID NOs: 21-40) were designed to have a non-zero net charge, high solubility when formulated in aqueous solution at pH 7.5 in presence of isotonic ionic strength (defined at 0.15M salt ions), and to transition from liquid state to hydrogel after administration to a subject. In some clinical applications, administration of pharmaceutical compositions comprising self-assembling peptides requires exposing the compositions to pressure and/or shear thinning (e.g., during injection through a syringe needle or transferred via a pump-based system). Ideally, pharmaceutical compositions comprising the self-assembling peptides described herein exhibit reduced viscosity under pressure or shear thinning forces and return to basal viscosity after removal from these forces. To determine the shear thinning properties of pharmaceutical compositions of the self-assembling peptides formulated at pH 7.5, formulations comprising varying ionic strengths were prepared using different concentrations of sodium chloride, and viscosity measured at increasing shear rates. Thixotropic properties of formulations were also determined as well as the storage modulus over time at specific frequencies and pressure.

Figure 6:
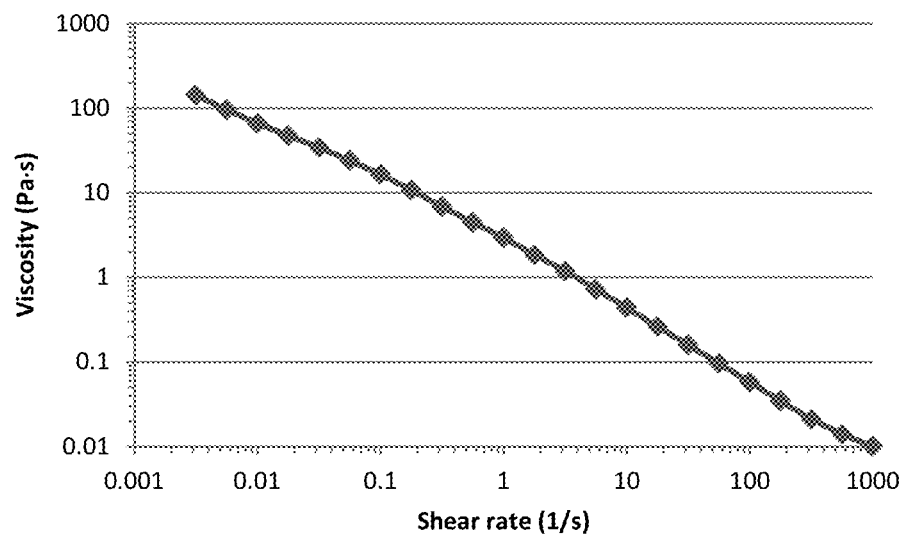
FIGS. 6-8 show shear-thinning properties of exemplary aqueous pharmaceutical compositions including the self-assembling peptides KLNL12 (SEQ ID NO: 21), IQIK13 (SEQ ID NO: 28), or NLEL12 (SEQ ID NO: 33).
Figure 7:
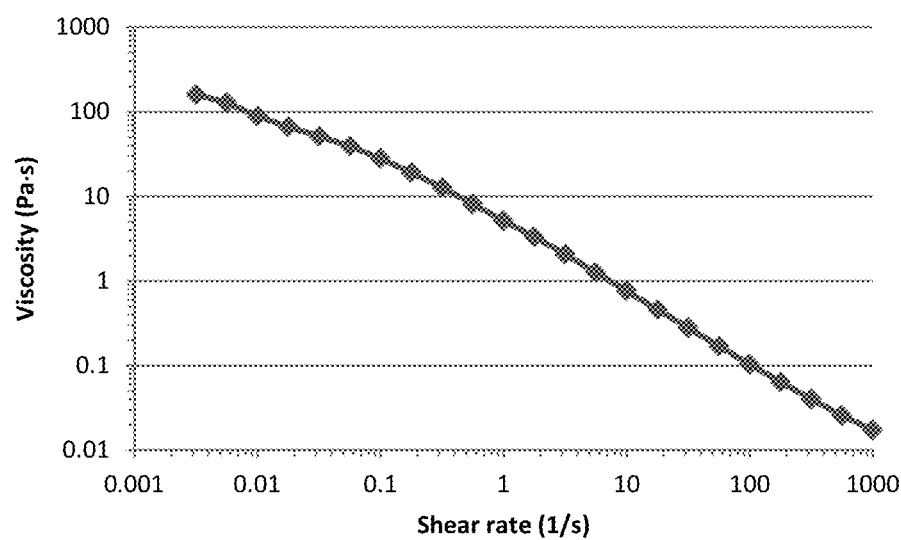
Figure 8:
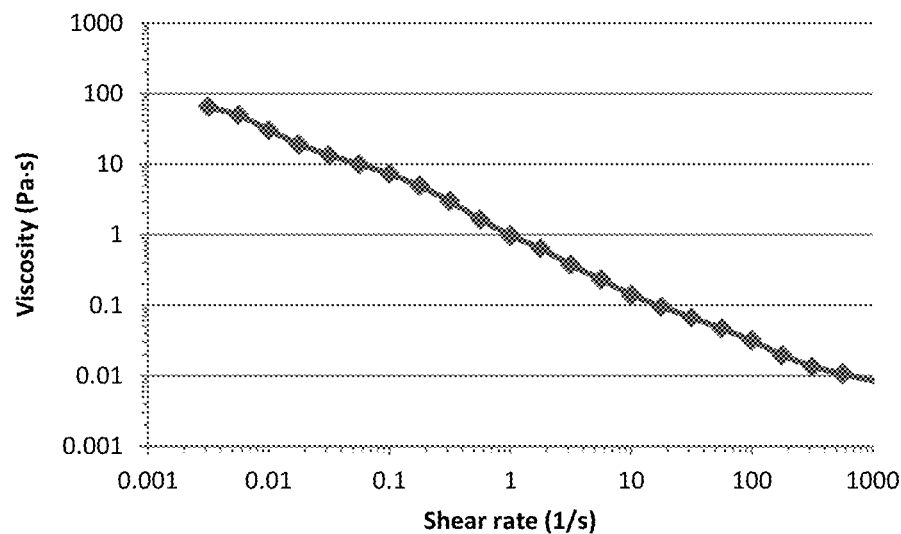
Figure 9:
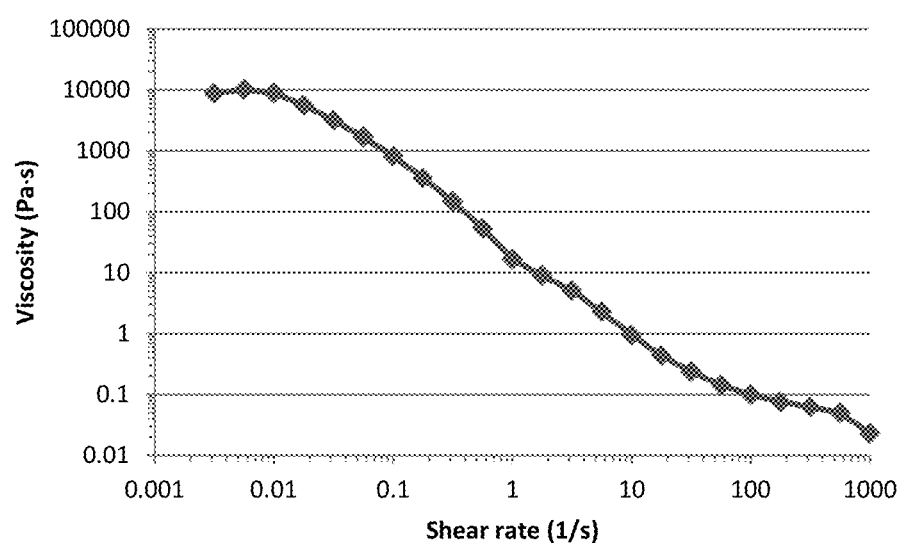
FIGS. 9-10 show shear-thinning properties of exemplary aqueous pharmaceutical compositions including the self-assembling peptides KLNL12 (SEQ ID NO: 21) or NLEL12 (SEQ ID NO: 33).
Figure 10:
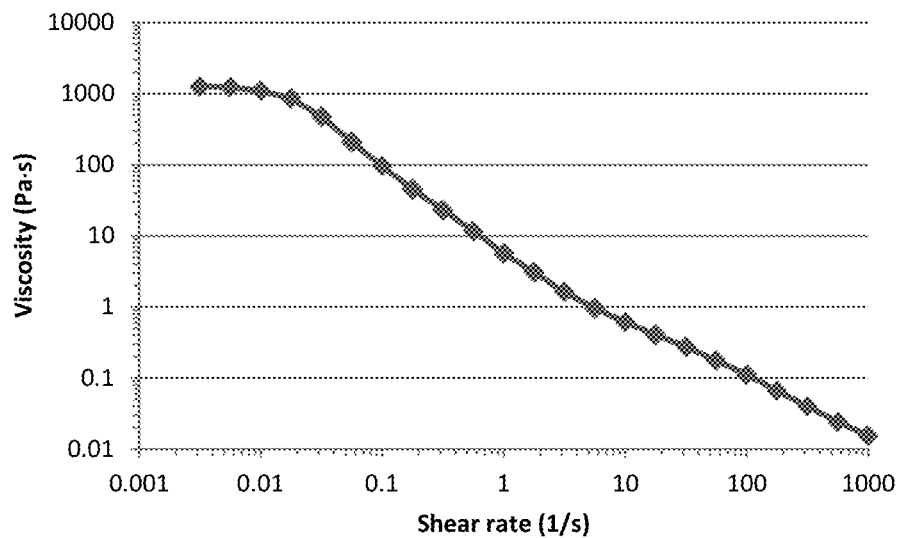

FIGS. 6-8 show the experimentally determined viscosity of aqueous pharmaceutical compositions comprising either 1% (w/v) KLNL12 (SEQ ID NO: 21), 1% (w/v) IQIK13 (SEQ ID NO: 28), or 1% (w/v) NLEL12 (SEQ ID NO: 33), at pH 7.5. FIGS. 9 and 10 show the experimentally determined viscosity of aqueous pharmaceutical compositions comprising either 1% KLNL12 (SEQ II NO: 21) or 1% NLEL12 (SEQ NO: 33), and 0.9% NaCl (to mimic physiological conditions) at pH 7.5. The data demonstrates that the aqueous pharmaceutical compositions exhibit sheer thinning. That is, decreased viscosity with increasing sheer rate. This property may advantageously facilitate application and use of the pharmaceutical compositions (e.g., due to decreased viscosity while pumping) while maintaining a desirable viscosity at a site of application (e.g., where no sheer force is being applied).

Figure 11:
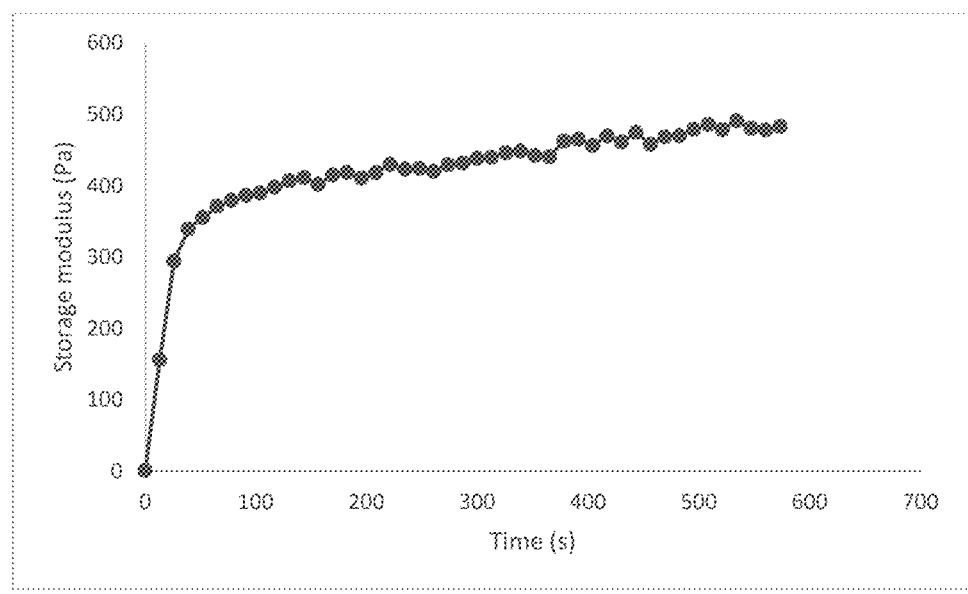
FIGS. 11-12 show thixotropic properties of exemplary aqueous pharmaceutical compositions including the self-assembling peptides KLNL12 (SEQ ID NO: 21) or NLEL12 (SEQ ID NO: 33).
Figure 12:
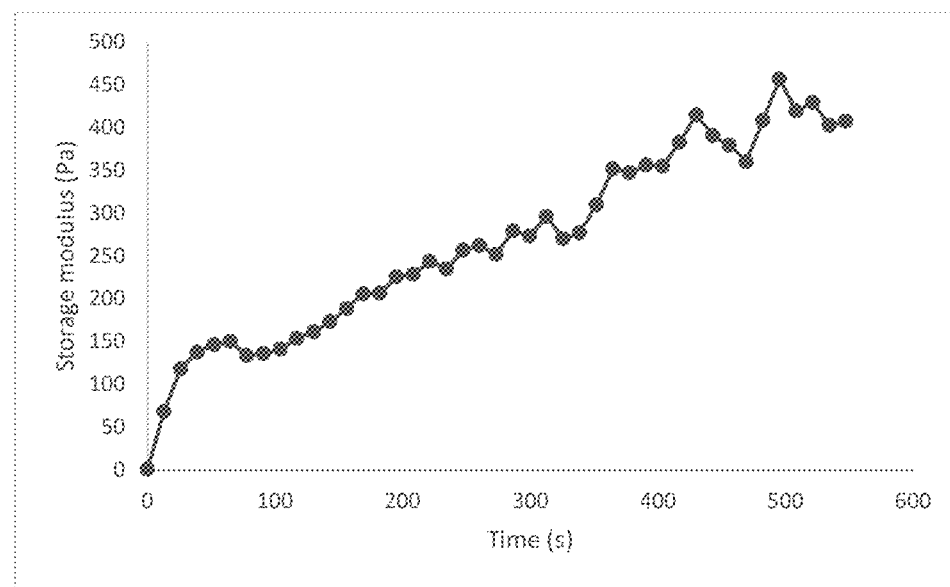

FIGS. 11 and 12 show the thixotropic properties of pharmaceutical compositions comprising 1% KLNL12 (SEQ ID NO: 21) or 1% NLEL12 (SEQ II) NO: 33), and 0.9% NaCl, at pH 7.5, after shear stress is removed. The aqueous pharmaceutical compositions were flowed at 1000 1/s of shear rate for 1 min and their storage modulus at 10 rad/s of frequency and at 0.1 Pa of stress was tested over time. The tested aqueous pharmaceutical compositions exhibited thixotropic properties. This property may advantageously facilitate application and use of the pharmaceutical compositions since they exhibit predictable and reliable properties after the application of mechanical stress.

Example 5

Determination of Rheological Properties of Pharmaceutical Compositions Comprising Self-Assembling Peptides Rheological properties of aqueous pharmaceutical compositions comprising the exemplary self-assembling peptides KLNL12 (SEQ ID NO: 21), KIQI13 (SEQ ID NO: 29), or NLEL12 (SEQ ID NO: 33) were determined by performing a frequency sweep test over storage modulus.

Figure 13:
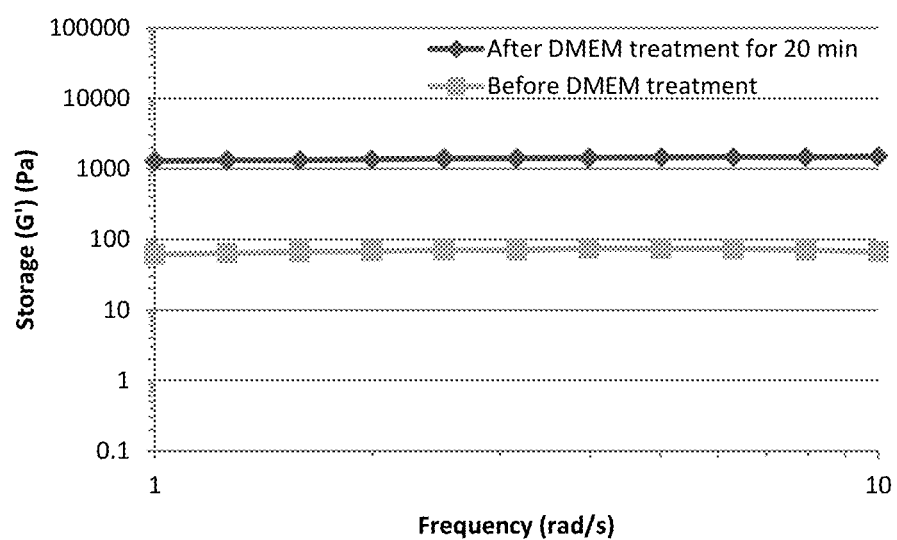
FIGS. 13-15 show changes in rheological properties of exemplary aqueous pharmaceutical compositions including the self-assembling peptides KLNL12 (SEQ ID NO: 21), KIQI13 (SEQ ID NO: 29), or NLEL12 (SEQ ID NO: 33), in response to exposure to DMEM.
Figure 14:
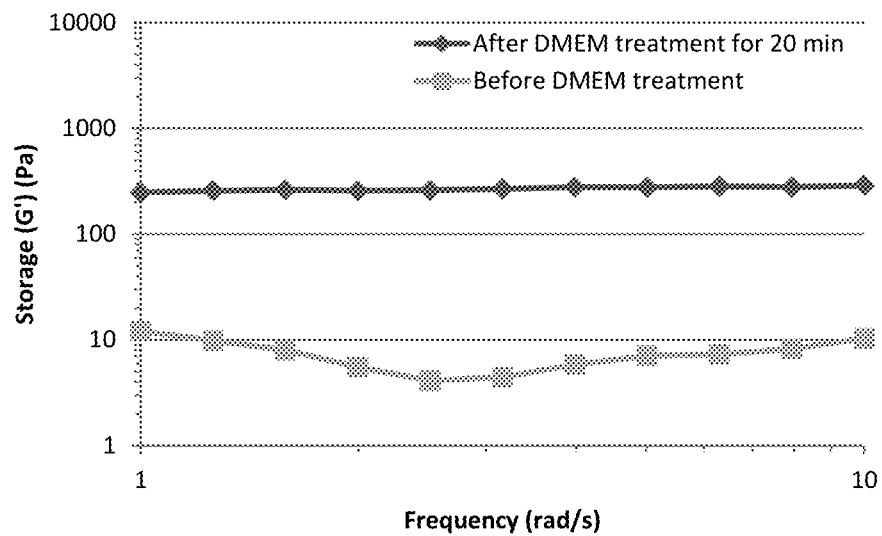
Figure 15:
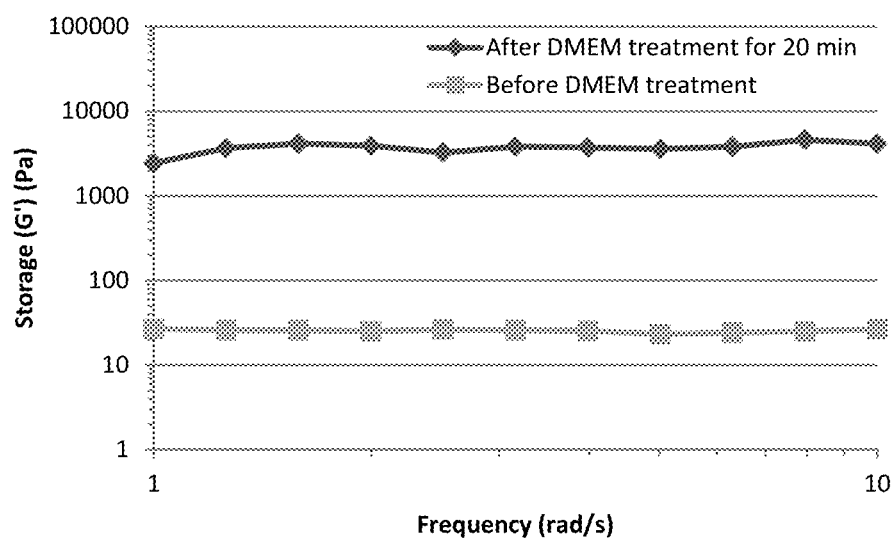

FIGS. 13-15 show the theological properties of aqueous pharmaceutical compositions comprising 1% (w/v) of KLNL12 (SEQ ID NO: 21) (FIG. 13), KIQI13 (SEQ ID NO: 29) (FIG. 14), or NLEL12 (SEQ ID NO: 33) (FIG. 15) at pH 7.5, before and after exposure to buffered Dulbecco's modified Eagle's medium (DMEM) to simulate body fluid. In each case, theological properties (e.g., mechanical strength) of the peptide solutions increased after DMEM treatment.

FIGS. 16-18 show the rheological properties of aqueous pharmaceutical compositions comprising 1% (w/v) of KLNL12 (SEQ ID NO: 21) (FIG. 16), KIQI13 (SEQ ID NO: 29) (FIG. 17), or NLEL12 (SEQ ID NO: 33) (FIG. 18) having isotonic salinity (0.9% NaCl) at pH 7.5, before and after exposure to DMEM. The rheological properties (e.g., mechanical strength) of the peptide solutions increased after DMEM treatment, The data above demonstrates that aqueous pharmaceutical compositions comprising KLNL12 (SEQ ID NO: 21), KIQI13 (SEQ ID NO: 29), or NLEL12 (SEQ ID NO: 33) exhibited increased mechanical strength in the presence of a physiological fluid, and therefore are suitable for therapeutic applications in vivo.

Example 6

Pharmaceutical Compositions Comprising Exemplary Self-Assembling Peptides Exhibited Reduced Tissue Damage as Compared to Pharmaceutical Compositions of RADA16

Given that the self-assembling peptides disclosed herein (Table 5; SEQ ID NOs: 21-40) have a non-zero net charge when formulated at neutral pH (e.g., pH 7.5), it was hypothesized that these compositions exhibited reduced adverse effects when administered or contacted with mammalian tissue, as compared to compositions comprising previously described self-assembling peptides (e.g., RADA16) which are formulated at acidic pH. Therefore, an in ivo porcine model system was used to assess the ability of these compositions to induce submucosal elevation upon injection into gastrointestinal submucosa, and the degree of tissue damage.

In this model, submucosal injections with liquid compositions were performed and the morphology of the site of injection analyzed. Submucosal injection with aqueous solutions is used during the excision of lesions from the gastrointestinal tract in order to facilitate removal of the lesion by providing a safety cushion during resection (see, e.g., Kim et al, (2013) World J. Gastroenterol. 19(20): 3069-76, incorporated herein by reference). Here, aqueous pharmaceutical compositions comprising three exemplary self-assembling peptides formulated at pH 7.5: KLNL12 (SEQ ID NO: 21), NLKL12 (SEQ ID NO: 23) or KIQI13 (SEQ ID NO: 29), were compared to an aqueous pharmaceutical composition comprising the previously described RADA16 self-assembling peptide (formulated at pH 2.5), a 0.4% solution of sodium hyaluronate (MucoUp®, Boston Scientific Japan K. K., Tokyo, Japan), and saline, pH 7.5. As shown in FIGS. 21A and 21B, injection with compositions comprising KLNL12 (SEQ ID NO: 21), NLKL12 (SEQ ID NO: 23) or KIQI13 (SEQ ID NO: 29) resulted in submucosal elevation. These compositions showed better submucosal elevation than saline and MucoUp® over time.

The effect of injection with aqueous pharmaceutical compositions comprising RADA16 (SEQ ID NO: 91), pH 2.5, with and without 0.9% (w/v) NaCl, on the morphology of submucosal tissue was analyzed after dissection of tissue at the site of injection using an electro-knife. As shown in FIGS. 22A and 22B, injection with compositions comprising RADA16 (SEQ ID NO: 91), with and without 0.9% NaCl, resulted in tissue damaged which included mucosal aggregation visualized as white precipitate near the injection site. In contrast, no tissue damage was observed when saline was injected (FIG. 22A).

The effect of injection with aqueous pharmaceutical compositions comprising the exemplary self-assembling peptides KLNL12 (SEQ ED NO: 21), NLEL12 (SEQ ID NO: 33), QLEL12 (SEQ ID NO: 35), or LELQ12 (SEQ ID NO: 36), all with 0.9% (w/v) NaCl, pH 7.5, on the morphology of submucosal tissue was also analyzed after dissection of tissue at the site of injection using an electro-knife. As shown in FIGS. 23A-23D, no mucosal aggregation was observed at the injection sites and the morphology of the sites was readily visible.

As an additional control, the effect of injection with phosphate buffered saline (PBS) at either pH 7.4 or pH 2.5 on the morphology of submucosal tissue was analyzed after dissection of tissue at the site of injection using an electro-knife. Mucosal aggregation visualized as white precipitate near the injection site was solely observed at sites injected with acidic PBS (i.e., pH 2.5) (data not shown), confirming that the changes in mucosal morphology appear to be attributable to the pH of the composition.

A summary of the appearance of stomach mucosa after injection with each composition used in this example is provided in Table 8 below.

TABLE 8

Appearance of porcine stomach mucosa at injection sites

| Injected Composition | Appearance of stomach mucosa |
| --- | --- |
| Water (neutral pH) | clear/transparent |
| Saline (0.9% NaCl) (neutral pH) | clear/transparent |
| PBS (pH 7.4) | clear/transparent |
| PBS (pH 2.5) | cloudy/aggregation |
| 0.2% RADA16 (SEQ ID NO: 91) (pH 2.5) | cloudy/aggregation |
| 0.2% RADA16 (SEQ ID NO: 91) with NaCl 0.9% (pH 2.5) | cloudy/aggregation |
| 0.1% (w/v) KLNL12 (SEQ ID NO: 21) with NaCl 0.9% (pH7.5) | clear/transparent |
| 0.1% (w/v) KIQI12 (SEQ ID NO: 99) with NaCl 0.9% (pH7.5) | Clear/transparent |
| 0.2% (w/v) NLEL12 (SEQ ID NO: 33) with NaCl 0.9% (pH 7.5) | clear/transparent |
| 0.2% (w/v) LELQ12 (SEQ ID NO: 36) with NaCl 0.9% (pH 7.5) | clear/transparent |
| 0.2% (w/v) QLEL12 (SEQ ID NO: 35) with NaCl 0.9% (pH 7.5) | clear/transparent |

The data presented in this example demonstrate that injections into porcine stomach submucosal layer with aqueous pharmaceutical compositions of RADA16 formulations (SEQ NO: 91), at pH 2.5, result in mucosal aggregation after a period of about 10-15 minutes. In contrast, injection with aqueous pharmaceutical compositions comprising the exemplary self-assembling peptides KLNL12 (SEQ ID NO: 21), KIQI12 (SEQ ID NO: 99), NLEL12 (SEQ ID NO: 33), QLEL12 (SEQ ID NO: 35), or (SEQ ID NO: 36), all at pH 7.5, do not appear to alter submucosal tissue morphology. This result is consistent with the notion that acidic compositions (e.g., those containing RADA16) damage the mucosal tissue, while injection with compositions at neutral pH results in less tissue damage.

In another embodiment, mucosal aggregation visualized as white precipitate near the injection site was evaluated in an in vivo porcine esophagus.

A summary of the appearance of esophagus mucosa after injection with each composition used in this example is provided in Table 9 below.

Mucosal aggregation was observed at sites injected with KIQI12 (SEQ ID NO: 99) as well as acidic PBS (pH 2) and RADA16 (SEQ ID NO: 91). KIQI12 (SEQ ID NO: 99) is a representative peptide among the positively charged peptides at physiological pH. However, mucosal aggregation was not observed with NLEL12 (SEQ ID NO: 33), QLEL12 (SEQ ID NO: 35), and LELQ12 (SEQ ID NO: 36), which are negatively charged at physiological pH. This result demonstrates that the changes in mucosal morphology appear to be attributable to both pH and the positive or negative charge of the composition at physiological pH in some submucosal tissues comprising esophagus.

TABLE 9

Appearance of porcine esophagus mucosa at injection sites

| Injected Composition | Appearance of stomach mucosa |
| --- | --- |
| Water (neutral pH) | clear/transparent |
| Saline (0.9% NaCl) (neutral pH) | clear/transparent |
| PBS (pH 7.4) | clear/transparent |
| PBS (pH 2.5) | cloudy/aggregation |
| 0.2% RADA16 (SEQ ID NO: 91) (pH 2.5) | cloudy/aggregation |
| 0.2% RADA16 (SEQ ID NO: 91) with NaCl 0.9% (pH 2.5) | cloudy/aggregation |

TABLE 9-continued

Appearance of porcine esophagus mucosa at injection sites

| Injected Composition | Appearance of stomach mucosa |
|---|---|
| 0.1% (w/v) KIQI12 (SEQ ID NO: 99) with NaCl 0.9% (pH7.5) | cloudy/aggregation |
| 0.2% (w/v) NLEL12 (SEQ ID NO: 33) with NaCl 0.9% (pH 7.5) | clear/transparent |
| 0.2% (w/v) LELQ12 (SEQ ID NO: 36) with NaCl 0.9% (pH 7.5) | clear/transparent |
| 0.2% (w/v) QLEL12 (SEQ ID NO: 35) with NaCl 0.9% (pH 7.5) | clear/transparent |

Example 7

Pharmaceutical Compositions with Increased Mechanical Strength

In some embodiments, peptides formulated as aqueous solutions, volume 700 μl, were placed between the plates of a rheometer (DHR-1, TA instruments, 40 mm cone and plate at a measuring geometry of 2.0° of cone angle) and frequency sweep tests were performed at 0.1 Hz to 10 Hz of frequency with 0.1% of strain; measurements were performed after 2 minutes of relaxation time at 37° C. In some embodiments, frequency sweep tests were performed after exposure to Dulbecco's Modified Eagle Medium (DMEM), where 10 mL of DMEM was added in chamber surrounding the plates, the sample in plates was submerged into the DMEM and the frequency test was performed as described after 20 minutes.

FIG. 24A shows changes in rheological properties of an aqueous pharmaceutical compositions comprising 0.15% (w/v) QLEL12 (SEQ ID NO: 35) with 0.9% NaCl (w/v) at pH 7.5, as reflected by increased mechanical strength after exposure to DMEM. At a frequency of 0.1 Hz, the mechanical strength of the composition comprising a self-assembling peptide was increased 23-fold. At a frequency of 1 Hz, the mechanical strength of the composition comprising a self-assembling peptide was increased 20-fold. At a frequency of 10 HZ, the mechanical strength of the composition comprising a self-assembling peptide was increased 9-fold.

FIG. 24B shows rheological properties of an aqueous pharmaceutical compositions comprising QLEL12 (SEQ ID NO: 35) with 0.9% NaCl (w/v) at pH 7.5 at various concentrations between 0.1% (w/V) and 0.3% (w/v). There was a linear relationship between the rheological property and concentration of the self-assembling peptide. Increased concertation of the self-assembling peptide within the composition resulted in increased mechanical strength.

Example 8

Pharmaceutical Compositions with Elevated Submucosal Layer and Increased Lifting Capability In some embodiments, the capability of peptide solution to elevate the submucosal layer was evaluated using an ex-vivo canine model. For this test, QLEL12 (SEQ ID NO: 35) was selected because it showed good rheological properties as well as no unclear/cloudy sites in the submucosa layer. QLEL12 (SEQ ID NO: 35) solutions of 0.1%, 0.15%, 0.2%, 0.3% (w/v) were prepared with 0.9% NaCl at pH 7.5. Normal saline was used as a reference solution. Each sample of 0.5 mL was injected to the submucosal layer of either stomach and colon in the ex-vivo canine model. The elevation heights were measured using electronic caliper at the point of 0 min, 10 min, 20 min, 30 min, 40 min, 50 min and 60 min after the initial injection. The elevation heights were measured using electronic caliper after each sample solution was injected using a syringe needle under the submucosal layer of stomach and colon. The elevation height is a distance between the bottom of the flat surface of skin and the top of the swollen bulla after injection under the submucosal layer.

The lifting capability of injected solution to lift the submucosal layer from the muscle layer after the solution is injected was measured. In some embodiments, the muscle layer was gastrointestinal. If initial elevation heights and overall elevation heights over time are high enough for submucosal removal procedure, this is considered to have good lifting capability.

Figure 25A:
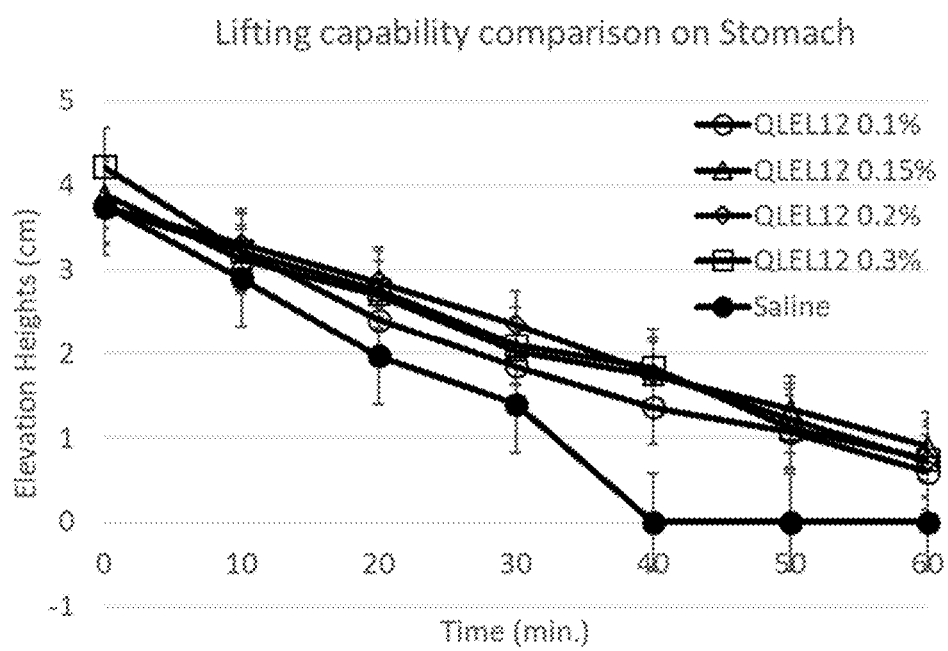

FIG. 25A shows elevation heights of the submucosal layer in the canine stomach after injecting 0.5 mL of QLEL12 (SEQ ID NO: 35) with 0.9% NaCl (w/v) at pH 7.5 at various concentrations between 0.1% (w/v) and 0.3% (w/v).

Figure 25B:
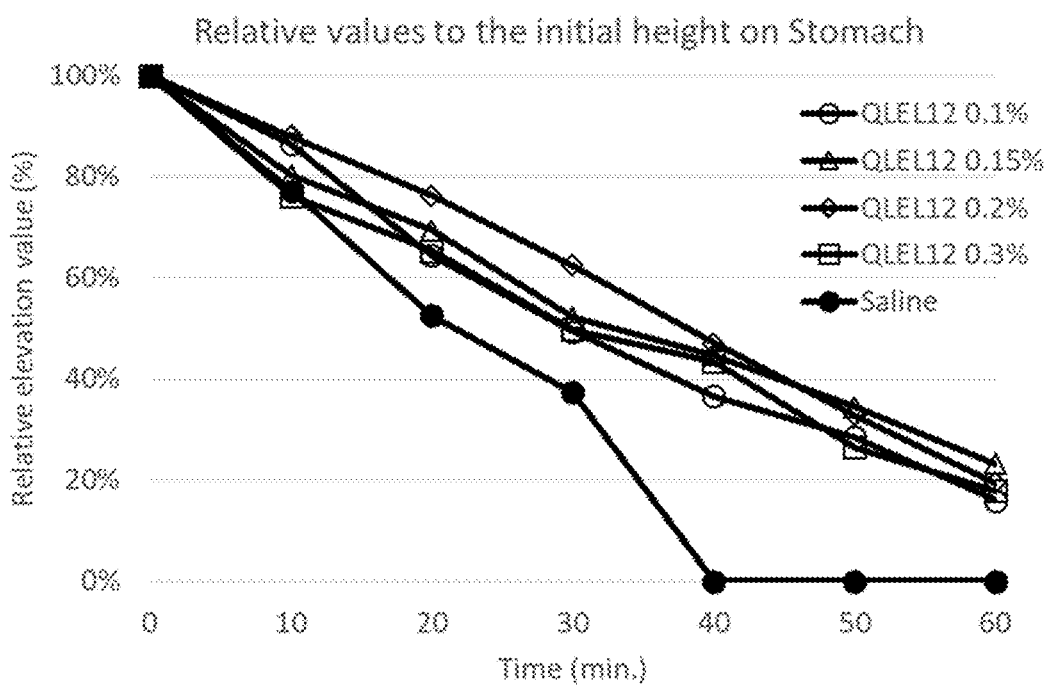

FIG. 25B shows relative elevation value to the initial height in the canine colon after injecting 0.5 mL of QLEL12 (SEQ ID NO: 35) with 0.9% NaCl (w/v) at pH 7.5 at various concentrations between 0.1% (w/v) and 0.3% (w/v).

Figure 25C:
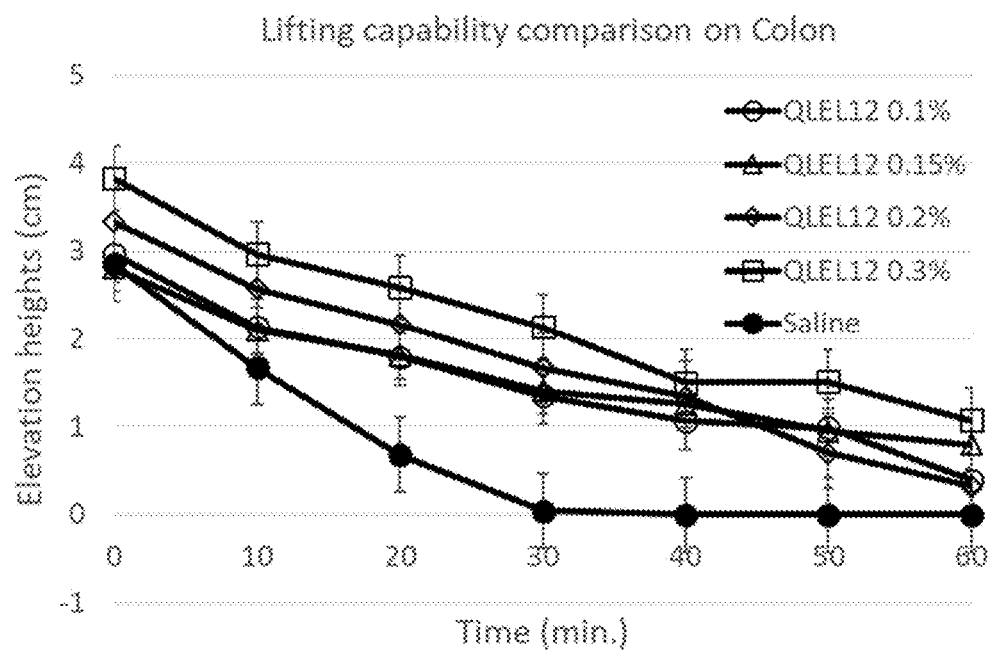

FIG. 25C shows elevation heights of the submucosal layer in the canine colon after injecting 0.5 mL of QLEL12 (SEQ ID NO: 35) with 0.9% NaCl (w/v) at pH 7.5 at various concentrations between 0.1% (w/v) and 0.3% (w/v).

Figure 25D:
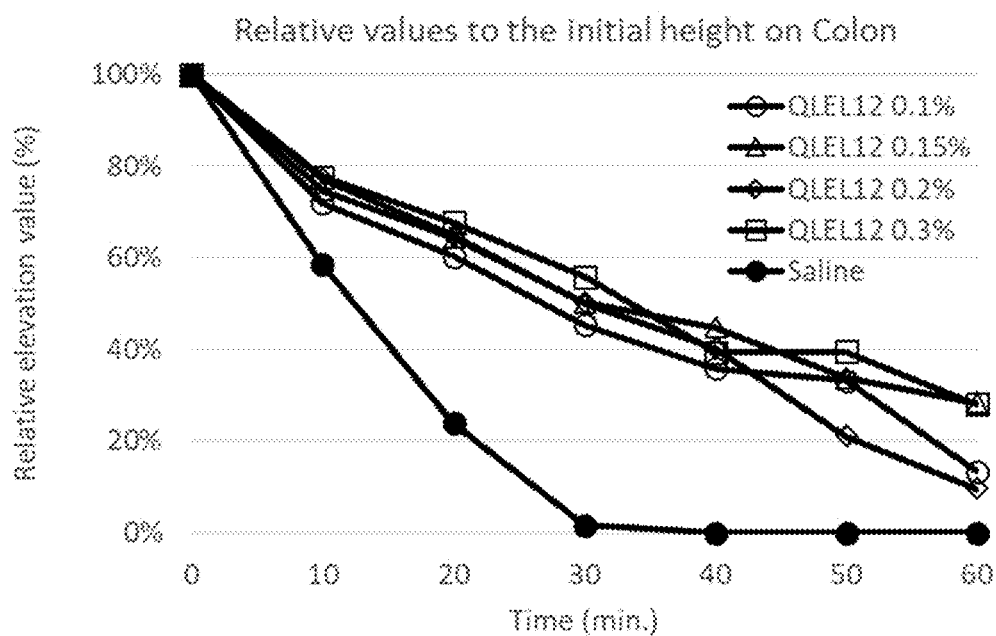

FIG. 25D shows relative elevation value to the initial height in the canine colon after injecting 0.5 mL of QLEL12 (SEQ ID NO: 35) with 0.9% NaCl (w/v) at pH 7.5 at various concentrations between 0.1% (w/v) and 0.3? (w/v).

Treatment with a composition comprising a representative self-assembling peptide resulted in increased retention of elevation heights of the submucosal layer in both the colon and stomach for all concentrations tested. Treatment with a composition comprising a representative self-assembling peptide also resulted in increased retention of relative elevation of the submucosal layer in both the colon and stomach for all concentrations tested. The lifting capability of a composition comprising a representative self-assembling peptide also showed good lifting capability, which aids in ease of removal of certain sections of the submucosal layer.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

What is claimed is:

1. A pharmaceutical composition comprising a self-assembling peptide, wherein the self-assembling peptide comprises the amino acid sequence set forth in SEQ ID NO:35.

2. The pharmaceutical composition of claim 1, wherein the self-assembling peptide comprises one or both of,
- an N-terminal functional group selected from the group consisting of an acetyl, a formyl, pyroglutamyl (pGlu), biotin, polyethylene glycol (PEG), urea, alkylamine, a carbamate, a sulfonamide, dansyl, 2,4-dintrophenyl, fluorescein, 7-methoxycoumarin acetic acid, 9-fluorenylmethyloxycarbonyl, palmitic acid, succinyl, chloroacetyl, maleimide, benzyloxycarbonyl, bromoacetyl, nitrilotriacetyl, tertbutoxycarbonyl, 4-hydroxyphenylpropionic acid, allyloxycarbonyl, butyric acid, a fatty acid, and trityl, and
- a C-terminal functional group selected from the group consisting of an amine, an amido, an N-alkyl amide, an aldehyde, an ester, an alcohol, para-nitroanilide (pNA), 7-amino-4-methylcoumarin (Amc), a hydrazide, hydroxamic acid, chloromethylketone, p-nitroaniline, para-nitrophenol, hydroxysucinimide ester, fluoromethylketone, cysteamide, 9-fluorenemethyl (Fm) ester, allyl ester, 2,4-dimethoxybenzyl ester, 2-phenylisopropyl ester, p-nitrobenzyl ester, and 2-chlorotrityl ester.

3. The pharmaceutical composition of claim 1, wherein the self-assembling peptide further comprises at least one biologically-active peptide motif at the N-terminal end, or the C-terminal end, or both, of the self-assembling peptide.

4. The pharmaceutical composition of claim 3, wherein the at least one biologically-active peptide motif is derived from laminin-1, collagen IV, fibronectin, elastin, bone marrow homing peptide 1, bone marrow homing peptide 2, or myelopeptide.

5. The pharmaceutical composition of claim 1, further comprising a tonicity agent wherein the tonicity agent comprises:
- one or more salts selected from the group consisting of NaCl, KCl, $MgCl_2$, $CaCl_2$, $NH_4Cl$, $Na_2HPO_4$, $KH_2PO_4$, and $CaSO_4$; or
- one or more sugars selected from the group consisting of dextrose, mannitol, glycerin, sucrose, and trehalose.

6. The pharmaceutical composition of claim 5, wherein the tonicity agent comprises one or more salts and is present in a concentration of about 0.01 M to about 0.3 M or about 0.15 M.

7. The pharmaceutical composition of claim 5, wherein the tonicity agent comprises one or more sugars and is present in a concentration of about 0.1-10% (w/v), or about 10% (w/v).

8. The pharmaceutical composition of claim 1, having a pH of from about 6 to about 8.

9. The pharmaceutical composition of claim 8, wherein the net charge of the self-assembling peptide is greater than or equal to +1 or less than or equal to −1.

10. The pharmaceutical composition of claim 1, wherein the concentration of the self-assembling peptide from about 0.01% (w/v) to about 10% (w/v), about 0.1% (w/v) to about 5% (w/v), about 0.5% (w/v) to about 1.5% (w/v), or about 1% (w/v).

11. The pharmaceutical composition of claim 1, further comprising an isolated cell.

12. The pharmaceutical composition of claim 11, wherein the isolated cell is a mammalian cell selected from the group consisting of: an immune cell, a stem cell, chondrocyte progenitor cells, pancreatic progenitor cells, myoblasts, fibroblasts, keratinocytes, neuronal cells, glial cells, astrocytes, pre-adipocytes, adipocytes, vascular endothelial cells, endothelial progenitor cells, mesenchymal cells, neural stem cells, immune cells, (e.g., B-cells and T-cells), smooth muscle progenitor cells, cardiac myocytes, fetal dermal fibroblasts, epidermal keratinocytes, myoblasts, and capillary endothelial cells.

13. The pharmaceutical composition of claim 1, wherein the pharmaceutical composition further comprises a bioactive agent.

14. The pharmaceutical composition of claim 13, wherein the bioactive agent is selected from the group consisting of a hormone, a growth factor, insulin, an enzyme, an siRNA, an shRNA, an antisense-RNA, an antibiotic, an antibody, and an anti-inflammatory agent.

15. The pharmaceutical composition of claim 1, wherein the pharmaceutical composition is an aqueous solution.

16. The pharmaceutical composition of claim 1, wherein the pharmaceutical composition is a hydrogel.

17. The pharmaceutical composition of claim 16, wherein the hydrogel comprises a storage modulus of at least about 10 Pascal (Pa).

18. An article of manufacture comprising the pharmaceutical composition of claim 1, wherein the article is a syringe, a vial, an auto-injector, tubing, or a catheter.

19. A method of promoting tissue repair or regeneration in a subject in need thereof, comprising administering to a tissue of the subject an effective amount of the pharmaceutical composition according to claim 1, thereby promoting tissue repair or regeneration of the tissue.

20. The method of claim 19, wherein the tissue is skin, bone, cartilage, neural, ligament, tendon, vascular tissue, optic, muscle, or cardiac tissue.

21. The method of claim 19, wherein the subject has a congenital disease or disorder resulting in a need for the tissue repair or regeneration; or the subject has suffered an injury resulting in a need for the tissue repair or regeneration, wherein the injury is a result of surgery, trauma, stroke, tumor, or a disease or disorder.

22. A method of promoting wound healing in a subject in need thereof, comprising administering to a subject's wound an effective amount of the pharmaceutical composition according to claim 1, thereby promoting wound healing and/or anti-microbial activity, wherein the wound comprises an abrasion, a burn, a chap, a detrition, a cut, an ulcer, a laceration, an incision, or a scratch.

23. A method of reducing bleeding at a site within a subject, comprising administering to the site an effective amount of the pharmaceutical composition according to claim 1, wherein the pharmaceutical composition creates a physical barrier thereby reducing bleeding at the site within the subject.

24. A method of excising a lesion from a site in the gastrointestinal tract of a subject, comprising:
   administering to the submucosa below the lesion a pharmaceutical composition according to claim 1 in an amount sufficient to lift the lesion; and
   excising the lesion from the site in the gastrointestinal tract of the subject.

25. The method of claim 24, wherein the lesion comprises a polyp, an ulcer, or a tumor.

26. The method of claim 24, wherein the lesion is present in a region of the gastrointestinal tract selected from the group consisting of: mouth, throat, esophagus, stomach, small intestine, large intestine, colon, and rectum.

27. A method of culturing a cell, comprising contacting the cell with the pharmaceutical composition according to claim 1.

28. A method of treating a pulmonary bulla in a subject, comprising:
   introducing a delivery device to a target area of the pulmonary bulla of the subject; positioning an end of the delivery device in the target area in which a treatment of the pulmonary bulla is desired;
   administering, through the delivery device, the pharmaceutical composition according to claim 1 in an effective amount and in an effective concentration to the target area to form a barrier under physiological conditions of the target area to treat the pulmonary bulla;
   removing the delivery device from the target area; and
   collapsing the pulmonary bulla prior or subsequent to administering the solution.

29. A method for mitigating adhesion to a biological tissue, the method comprising administering to the biological tissue an effective amount of the pharmaceutical composition according to claim 1, to thereby mitigate adhesion to the biological tissue.

30. A method of filling a bone void in a subject, comprising
   introducing a delivery device to a bone of a subject;
   positioning an end of the delivery device proximate a void in the bone where promotion of bone growth is desired;
   administering the pharmaceutical composition according to claim 1 in a concentration sufficient to form a hydrogel scaffold under physiological conditions through the delivery device; and
   removing the delivery device.

31. A method of treating dry eye in a subject, comprising administering to an eye of the subject an effective amount of the pharmaceutical composition according to claim 1.

32. A self-assembling peptide comprising the amino acid sequence set forth in SEQ ID NO:35.

* * * * *

SEQUENCE LISTING

<160> NUMBER OF SEQ ID NOS: 99

<210> SEQ ID NO 1
<211> LENGTH: 12
<212> TYPE: PRT
<213> ORGANISM: Artificial
<220> FEATURE:
<223> OTHER INFORMATION: Self-assembling peptides

<400> SEQUENCE: 1

Lys Leu Asn Leu Lys Leu Asn Leu Lys Leu Asn Leu
1               5                   10

<210> SEQ ID NO 2
<211> LENGTH: 12
<212> TYPE: PRT
<213> ORGANISM: Artificial
<220> FEATURE:
<223> OTHER INFORMATION: Self-assembling peptides

<400> SEQUENCE: 2

Leu Asn Leu Lys Leu Asn Leu Lys Leu Asn Leu Lys
1               5                   10

<210> SEQ ID NO 3
<211> LENGTH: 12
<212> TYPE: PRT
<213> ORGANISM: Artificial
<220> FEATURE:
<223> OTHER INFORMATION: Self-assembling peptides

<400> SEQUENCE: 3

Asn Leu Lys Leu Asn Leu Lys Leu Asn Leu Lys Leu
1               5                   10

<210> SEQ ID NO 4
<211> LENGTH: 12
<212> TYPE: PRT
<213> ORGANISM: Artificial
<220> FEATURE:
<223> OTHER INFORMATION: Self-assembling peptides

<400> SEQUENCE: 4

Leu Lys Leu Asn Leu Lys Leu Asn Leu Lys Leu Asn
1               5                   10

<210> SEQ ID NO 5
<211> LENGTH: 13
<212> TYPE: PRT
<213> ORGANISM: Artificial
<220> FEATURE:
<223> OTHER INFORMATION: Self-assembling peptides

<400> SEQUENCE: 5

Lys Leu Asn Leu Lys Leu Asn Leu Lys Leu Asn Leu Lys
1               5                   10

<210> SEQ ID NO 6
<211> LENGTH: 17
<212> TYPE: PRT
<213> ORGANISM: Artificial
<220> FEATURE:
<223> OTHER INFORMATION: Self-assembling peptides

<400> SEQUENCE: 6

Lys Leu Asn Leu Lys Leu Asn Leu Lys Leu Asn Leu Lys Leu Asn Leu
1               5                   10                  15

Lys

<210> SEQ ID NO 7
<211> LENGTH: 12
<212> TYPE: PRT
<213> ORGANISM: Artificial
<220> FEATURE:
<223> OTHER INFORMATION: Self-assembling peptides

<400> SEQUENCE: 7

Ile Gln Ile Lys Ile Gln Ile Lys Ile Gln Ile Lys
1               5                   10

<210> SEQ ID NO 8
<211> LENGTH: 13
<212> TYPE: PRT
<213> ORGANISM: Artificial
<220> FEATURE:
<223> OTHER INFORMATION: Self-assembling peptides

<400> SEQUENCE: 8

Ile Gln Ile Lys Ile Gln Ile Lys Ile Gln Ile Lys Ile
1               5                   10

<210> SEQ ID NO 9
<211> LENGTH: 13
<212> TYPE: PRT
<213> ORGANISM: Artificial
<220> FEATURE:
<223> OTHER INFORMATION: Self-assembling peptides

<400> SEQUENCE: 9

Ile Gln Ile Lys Ile Gln Ile Lys Ile Gln Ile Lys Ile
1               5                   10

<210> SEQ ID NO 10
<211> LENGTH: 13
<212> TYPE: PRT
<213> ORGANISM: Artificial
<220> FEATURE:
<223> OTHER INFORMATION: Self-assembling peptides

<400> SEQUENCE: 10

Gln Ile Lys Ile Gln Ile Lys Ile Gln Ile Lys Ile Gln
1               5                   10

<210> SEQ ID NO 11
<211> LENGTH: 13
<212> TYPE: PRT
<213> ORGANISM: Artificial
<220> FEATURE:
<223> OTHER INFORMATION: Self-assembling peptides

<400> SEQUENCE: 11

Ile Lys Ile Gln Ile Lys Ile Gln Ile Lys Ile Gln Ile
1               5                   10

<210> SEQ ID NO 12
<211> LENGTH: 13
<212> TYPE: PRT
<213> ORGANISM: Artificial
<220> FEATURE:
<223> OTHER INFORMATION: Self-assembling peptides

<400> SEQUENCE: 12

Ile Asn Ile Lys Ile Asn Ile Lys Ile Asn Ile Lys Ile

```
1               5                  10
```

<210> SEQ ID NO 13
<211> LENGTH: 12
<212> TYPE: PRT
<213> ORGANISM: Artificial
<220> FEATURE:
<223> OTHER INFORMATION: Self-assembling peptides

<400> SEQUENCE: 13

```
Asn Leu Glu Leu Asn Leu Glu Leu Asn Leu Glu Leu
1               5                  10
```

<210> SEQ ID NO 14
<211> LENGTH: 12
<212> TYPE: PRT
<213> ORGANISM: Artificial
<220> FEATURE:
<223> OTHER INFORMATION: Self-assembling peptides

<400> SEQUENCE: 14

```
Asn Leu Asp Leu Asn Leu Asp Leu Asn Leu Asp Leu
1               5                  10
```

<210> SEQ ID NO 15
<211> LENGTH: 12
<212> TYPE: PRT
<213> ORGANISM: Artificial
<220> FEATURE:
<223> OTHER INFORMATION: Self-assembling peptides

<400> SEQUENCE: 15

```
Gln Leu Glu Leu Gln Leu Glu Leu Gln Leu Glu Leu
1               5                  10
```

<210> SEQ ID NO 16
<211> LENGTH: 12
<212> TYPE: PRT
<213> ORGANISM: Artificial
<220> FEATURE:
<223> OTHER INFORMATION: self-assembling peptides

<400> SEQUENCE: 16

```
Leu Glu Leu Gln Leu Glu Leu Gln Leu Glu Leu Gln
1               5                  10
```

<210> SEQ ID NO 17
<211> LENGTH: 12
<212> TYPE: PRT
<213> ORGANISM: Artificial
<220> FEATURE:
<223> OTHER INFORMATION: Self-assembling peptides

<400> SEQUENCE: 17

```
Lys Ala Asn Ala Lys Ala Asn Ala Lys Ala Asn Ala
1               5                  10
```

<210> SEQ ID NO 18
<211> LENGTH: 12
<212> TYPE: PRT
<213> ORGANISM: Artificial
<220> FEATURE:
<223> OTHER INFORMATION: Self-assembling peptides

<400> SEQUENCE: 18

```
Lys Val Asn Val Lys Val Asn Val Lys Val Asn Val
1               5                  10
```

```
<210> SEQ ID NO 19
<211> LENGTH: 16
<212> TYPE: PRT
<213> ORGANISM: Artificial
<220> FEATURE:
<223> OTHER INFORMATION: Self-assembling peptides

<400> SEQUENCE: 19

Arg Ala Asn Ala Arg Ala Asn Ala Arg Ala Asn Ala Arg Ala Asn Ala
1               5                   10                  15

<210> SEQ ID NO 20
<211> LENGTH: 12
<212> TYPE: PRT
<213> ORGANISM: Artificial
<220> FEATURE:
<223> OTHER INFORMATION: self-assembling peptides

<400> SEQUENCE: 20

Lys Leu Thr Leu Lys Leu Thr Leu Lys Leu Thr Leu
1               5                   10

<210> SEQ ID NO 21
<211> LENGTH: 12
<212> TYPE: PRT
<213> ORGANISM: Artificial
<220> FEATURE:
<223> OTHER INFORMATION: self-assembling peptides

<400> SEQUENCE: 21

Lys Leu Asn Leu Lys Leu Asn Leu Lys Leu Asn Leu
1               5                   10

<210> SEQ ID NO 22
<211> LENGTH: 12
<212> TYPE: PRT
<213> ORGANISM: Artificial
<220> FEATURE:
<223> OTHER INFORMATION: self-assembling peptides

<400> SEQUENCE: 22

Leu Asn Leu Lys Leu Asn Leu Lys Leu Asn Leu Lys
1               5                   10

<210> SEQ ID NO 23
<211> LENGTH: 12
<212> TYPE: PRT
<213> ORGANISM: Artificial
<220> FEATURE:
<223> OTHER INFORMATION: self-assembling peptides

<400> SEQUENCE: 23

Asn Leu Lys Leu Asn Leu Lys Leu Asn Leu Lys Leu
1               5                   10

<210> SEQ ID NO 24
<211> LENGTH: 12
<212> TYPE: PRT
<213> ORGANISM: Artificial
<220> FEATURE:
<223> OTHER INFORMATION: self-assembling peptides

<400> SEQUENCE: 24

Leu Lys Leu Asn Leu Lys Leu Asn Leu Lys Leu Asn
1               5                   10
```

```
<210> SEQ ID NO 25
<211> LENGTH: 13
<212> TYPE: PRT
<213> ORGANISM: Artificial
<220> FEATURE:
<223> OTHER INFORMATION: self-assembling peptides

<400> SEQUENCE: 25

Lys Leu Asn Leu Lys Leu Asn Leu Lys Leu Asn Leu Lys
1               5                   10

<210> SEQ ID NO 26
<211> LENGTH: 17
<212> TYPE: PRT
<213> ORGANISM: Artificial
<220> FEATURE:
<223> OTHER INFORMATION: self-assembling peptides

<400> SEQUENCE: 26

Lys Leu Asn Leu Lys Leu Asn Leu Lys Leu Asn Leu Lys Leu Asn Leu
1               5                   10                  15

Lys

<210> SEQ ID NO 27
<211> LENGTH: 12
<212> TYPE: PRT
<213> ORGANISM: Artificial
<220> FEATURE:
<223> OTHER INFORMATION: self-assembling peptides

<400> SEQUENCE: 27

Ile Gln Ile Lys Ile Gln Ile Lys Ile Gln Ile Lys
1               5                   10

<210> SEQ ID NO 28
<211> LENGTH: 13
<212> TYPE: PRT
<213> ORGANISM: Artificial
<220> FEATURE:
<223> OTHER INFORMATION: self-assembling peptides

<400> SEQUENCE: 28

Ile Gln Ile Lys Ile Gln Ile Lys Ile Gln Ile Lys Ile
1               5                   10

<210> SEQ ID NO 29
<211> LENGTH: 13
<212> TYPE: PRT
<213> ORGANISM: Artificial
<220> FEATURE:
<223> OTHER INFORMATION: self-assembling peptides

<400> SEQUENCE: 29

Lys Ile Gln Ile Lys Ile Gln Ile Lys Ile Gln Ile Lys
1               5                   10

<210> SEQ ID NO 30
<211> LENGTH: 13
<212> TYPE: PRT
<213> ORGANISM: Artificial
<220> FEATURE:
<223> OTHER INFORMATION: self-assembling peptides

<400> SEQUENCE: 30

Gln Ile Lys Ile Gln Ile Lys Ile Gln Ile Lys Ile Gln
1               5                   10
```

```
<210> SEQ ID NO 31
<211> LENGTH: 13
<212> TYPE: PRT
<213> ORGANISM: Artificial
<220> FEATURE:
<223> OTHER INFORMATION: self-assembling peptides

<400> SEQUENCE: 31

Ile Lys Ile Gln Ile Lys Ile Gln Ile Lys Ile Gln Ile
1               5                   10

<210> SEQ ID NO 32
<211> LENGTH: 13
<212> TYPE: PRT
<213> ORGANISM: Artificial
<220> FEATURE:
<223> OTHER INFORMATION: self-assembling peptides

<400> SEQUENCE: 32

Ile Asn Ile Lys Ile Asn Ile Lys Ile Asn Ile Lys Ile
1               5                   10

<210> SEQ ID NO 33
<211> LENGTH: 12
<212> TYPE: PRT
<213> ORGANISM: Artificial
<220> FEATURE:
<223> OTHER INFORMATION: self-assembling peptides

<400> SEQUENCE: 33

Asn Leu Glu Leu Asn Leu Glu Leu Asn Leu Glu Leu
1               5                   10

<210> SEQ ID NO 34
<211> LENGTH: 12
<212> TYPE: PRT
<213> ORGANISM: Artificial
<220> FEATURE:
<223> OTHER INFORMATION: self-assembling peptides

<400> SEQUENCE: 34

Asn Leu Asp Leu Asn Leu Asp Leu Asn Leu Asp Leu
1               5                   10

<210> SEQ ID NO 35
<211> LENGTH: 12
<212> TYPE: PRT
<213> ORGANISM: Artificial
<220> FEATURE:
<223> OTHER INFORMATION: self-assembling peptides

<400> SEQUENCE: 35

Gln Leu Glu Leu Gln Leu Glu Leu Gln Leu Glu Leu
1               5                   10

<210> SEQ ID NO 36
<211> LENGTH: 12
<212> TYPE: PRT
<213> ORGANISM: Artificial
<220> FEATURE:
<223> OTHER INFORMATION: self-assembling peptides

<400> SEQUENCE: 36

Leu Glu Leu Gln Leu Glu Leu Gln Leu Glu Leu Gln
1               5                   10
```

```
<210> SEQ ID NO 37
<211> LENGTH: 12
<212> TYPE: PRT
<213> ORGANISM: Artificial
<220> FEATURE:
<223> OTHER INFORMATION: self-assembling peptides

<400> SEQUENCE: 37

Lys Ala Asn Ala Lys Ala Asn Ala Lys Ala Asn Ala
1               5                   10

<210> SEQ ID NO 38
<211> LENGTH: 12
<212> TYPE: PRT
<213> ORGANISM: Artificial
<220> FEATURE:
<223> OTHER INFORMATION: self-assembling peptides

<400> SEQUENCE: 38

Lys Val Asn Val Lys Val Asn Val Lys Val Asn Val
1               5                   10

<210> SEQ ID NO 39
<211> LENGTH: 16
<212> TYPE: PRT
<213> ORGANISM: Artificial
<220> FEATURE:
<223> OTHER INFORMATION: self-assembling peptides

<400> SEQUENCE: 39

Arg Ala Asn Ala Arg Ala Asn Ala Arg Ala Asn Ala Arg Ala Asn Ala
1               5                   10                  15

<210> SEQ ID NO 40
<211> LENGTH: 12
<212> TYPE: PRT
<213> ORGANISM: Artificial
<220> FEATURE:
<223> OTHER INFORMATION: self-assembling peptides

<400> SEQUENCE: 40

Lys Leu Thr Leu Lys Leu Thr Leu Lys Leu Thr Leu
1               5                   10

<210> SEQ ID NO 41
<211> LENGTH: 12
<212> TYPE: PRT
<213> ORGANISM: Artificial
<220> FEATURE:
<223> OTHER INFORMATION: Laminin-1

<400> SEQUENCE: 41

Ala Ala Ser Ile Lys Val Ala Val Ser Ala Asp Arg
1               5                   10

<210> SEQ ID NO 42
<211> LENGTH: 19
<212> TYPE: PRT
<213> ORGANISM: Artificial
<220> FEATURE:
<223> OTHER INFORMATION: Laminin-1

<400> SEQUENCE: 42

Cys Ser Arg Ala Arg Lys Gln Ala Ala Ser Ile Lys Val Ala Val Ser
1               5                   10                  15

Ala Asp Arg
```

```
<210> SEQ ID NO 43
<211> LENGTH: 5
<212> TYPE: PRT
<213> ORGANISM: Artificial
<220> FEATURE:
<223> OTHER INFORMATION: Laminin-1

<400> SEQUENCE: 43

Tyr Ile Gly Ser Arg
1               5

<210> SEQ ID NO 44
<211> LENGTH: 5
<212> TYPE: PRT
<213> ORGANISM: Artificial
<220> FEATURE:
<223> OTHER INFORMATION: Laminin-1

<400> SEQUENCE: 44

Pro Asp Gly Ser Arg
1               5

<210> SEQ ID NO 45
<211> LENGTH: 7
<212> TYPE: PRT
<213> ORGANISM: Artificial
<220> FEATURE:
<223> OTHER INFORMATION: Laminin-1

<400> SEQUENCE: 45

Arg Tyr Val Val Leu Pro Arg
1               5

<210> SEQ ID NO 46
<211> LENGTH: 12
<212> TYPE: PRT
<213> ORGANISM: Artificial
<220> FEATURE:
<223> OTHER INFORMATION: Laminin-1

<400> SEQUENCE: 46

Lys Ala Phe Asp Ile Thr Tyr Val Arg Leu Lys Phe
1               5                   10

<210> SEQ ID NO 47
<211> LENGTH: 12
<212> TYPE: PRT
<213> ORGANISM: Artificial
<220> FEATURE:
<223> OTHER INFORMATION: Collagen IV

<400> SEQUENCE: 47

Thr Ala Gly Ser Cys Leu Arg Lys Phe Ser Thr Met
1               5                   10

<210> SEQ ID NO 48
<211> LENGTH: 10
<212> TYPE: PRT
<213> ORGANISM: Artificial
<220> FEATURE:
<223> OTHER INFORMATION: Laminin-1

<400> SEQUENCE: 48

Arg Asn Ile Ala Glu Ile Ile Lys Asp Ile
1               5                   10
```

<210> SEQ ID NO 49
<211> LENGTH: 4
<212> TYPE: PRT
<213> ORGANISM: Artificial
<220> FEATURE:
<223> OTHER INFORMATION: Laminin-1

<400> SEQUENCE: 49

Tyr Val Arg Leu
1

<210> SEQ ID NO 50
<211> LENGTH: 6
<212> TYPE: PRT
<213> ORGANISM: Artificial
<220> FEATURE:
<223> OTHER INFORMATION: Laminin-1

<400> SEQUENCE: 50

Ile Arg Val Thr Leu Asn
1               5

<210> SEQ ID NO 51
<211> LENGTH: 8
<212> TYPE: PRT
<213> ORGANISM: Artificial
<220> FEATURE:
<223> OTHER INFORMATION: Laminin-1

<400> SEQUENCE: 51

Thr Thr Val Lys Tyr Ile Phe Arg
1               5

<210> SEQ ID NO 52
<211> LENGTH: 8
<212> TYPE: PRT
<213> ORGANISM: Artificial
<220> FEATURE:
<223> OTHER INFORMATION: Laminin-1

<400> SEQUENCE: 52

Ser Ile Lys Ile Arg Gly Thr Tyr
1               5

<210> SEQ ID NO 53
<211> LENGTH: 13
<212> TYPE: PRT
<213> ORGANISM: Artificial
<220> FEATURE:
<223> OTHER INFORMATION: Laminin-1

<400> SEQUENCE: 53

Arg Gln Val Phe Gln Val Ala Tyr Ile Ile Ile Lys Ala
1               5                   10

<210> SEQ ID NO 54
<211> LENGTH: 10
<212> TYPE: PRT
<213> ORGANISM: Artificial
<220> FEATURE:
<223> OTHER INFORMATION: Laminin-1

<400> SEQUENCE: 54

Phe Gln Ile Ala Tyr Val Ile Val Lys Ala
1               5                   10

```
<210> SEQ ID NO 55
<211> LENGTH: 13
<212> TYPE: PRT
<213> ORGANISM: Artificial
<220> FEATURE:
<223> OTHER INFORMATION: Laminin-1

<400> SEQUENCE: 55

Gly Gln Leu Phe His Val Ala Tyr Ile Ile Ile Lys Ala
1               5                   10

<210> SEQ ID NO 56
<211> LENGTH: 10
<212> TYPE: PRT
<213> ORGANISM: Artificial
<220> FEATURE:
<223> OTHER INFORMATION: Laminin-1

<400> SEQUENCE: 56

Phe His Val Ala Tyr Val Leu Ile Lys Ala
1               5                   10

<210> SEQ ID NO 57
<211> LENGTH: 13
<212> TYPE: PRT
<213> ORGANISM: Artificial
<220> FEATURE:
<223> OTHER INFORMATION: Laminin-1

<400> SEQUENCE: 57

Leu Glu Asn Gly Glu Ile Val Ser Leu Val Asn Gly Arg
1               5                   10

<210> SEQ ID NO 58
<211> LENGTH: 6
<212> TYPE: PRT
<213> ORGANISM: Artificial
<220> FEATURE:
<223> OTHER INFORMATION: Fibronectin

<400> SEQUENCE: 58

Leu Gly Thr Ile Pro Gly
1               5

<210> SEQ ID NO 59
<211> LENGTH: 4
<212> TYPE: PRT
<213> ORGANISM: Artificial
<220> FEATURE:
<223> OTHER INFORMATION: Fibronectin

<400> SEQUENCE: 59

Asp Gly Glu Ala
1

<210> SEQ ID NO 60
<211> LENGTH: 4
<212> TYPE: PRT
<213> ORGANISM: Artificial
<220> FEATURE:
<223> OTHER INFORMATION: Fibronectin

<400> SEQUENCE: 60

Arg Glu Asp Val
1

<210> SEQ ID NO 61
```

```
<211> LENGTH: 5
<212> TYPE: PRT
<213> ORGANISM: Artificial
<220> FEATURE:
<223> OTHER INFORMATION: Elastin

<400> SEQUENCE: 61

Gly Val Gly Val Pro
1               5

<210> SEQ ID NO 62
<211> LENGTH: 6
<212> TYPE: PRT
<213> ORGANISM: Artificial
<220> FEATURE:
<223> OTHER INFORMATION: Elastin

<400> SEQUENCE: 62

Gly Val Gly Val Ala Pro
1               5

<210> SEQ ID NO 63
<211> LENGTH: 5
<212> TYPE: PRT
<213> ORGANISM: Artificial
<220> FEATURE:
<223> OTHER INFORMATION: Laminin-1

<400> SEQUENCE: 63

Ile Lys Val Ala Val
1               5

<210> SEQ ID NO 64
<211> LENGTH: 7
<212> TYPE: PRT
<213> ORGANISM: Artificial
<220> FEATURE:
<223> OTHER INFORMATION: Bone marrow homing peptide 2

<400> SEQUENCE: 64

Pro Phe Ser Ser Thr Lys Thr
1               5

<210> SEQ ID NO 65
<211> LENGTH: 8
<212> TYPE: PRT
<213> ORGANISM: Artificial
<220> FEATURE:
<223> OTHER INFORMATION: Bone marrow homing peptide 1

<400> SEQUENCE: 65

Ser Lys Pro Pro Gly Thr Ser Ser
1               5

<210> SEQ ID NO 66
<211> LENGTH: 9
<212> TYPE: PRT
<213> ORGANISM: Artificial
<220> FEATURE:
<223> OTHER INFORMATION: Laminin-1

<400> SEQUENCE: 66

Ser Asp Pro Gly Tyr Ile Gly Ser Arg
1               5

<210> SEQ ID NO 67
<211> LENGTH: 10
```

```
<212> TYPE: PRT
<213> ORGANISM: Artificial
<220> FEATURE:
<223> OTHER INFORMATION: Laminin-1

<400> SEQUENCE: 67

Arg Asn Ile Ala Glu Leu Leu Lys Asp Ile
1               5                   10

<210> SEQ ID NO 68
<211> LENGTH: 12
<212> TYPE: PRT
<213> ORGANISM: Artificial
<220> FEATURE:
<223> OTHER INFORMATION: Collagen IV

<400> SEQUENCE: 68

Pro Arg Gly Asp Ser Gly Tyr Arg Gly Asp Ser Gly
1               5                   10

<210> SEQ ID NO 69
<211> LENGTH: 7
<212> TYPE: PRT
<213> ORGANISM: Artificial
<220> FEATURE:
<223> OTHER INFORMATION: Myelopeptide

<400> SEQUENCE: 69

Gly Phe Leu Gly Phe Pro Thr
1               5

<210> SEQ ID NO 70
<211> LENGTH: 7
<212> TYPE: PRT
<213> ORGANISM: Artificial
<220> FEATURE:
<223> OTHER INFORMATION: Laminin-1

<400> SEQUENCE: 70

Tyr Gly Pro Asp Ser Gly Arg
1               5

<210> SEQ ID NO 71
<211> LENGTH: 18
<212> TYPE: PRT
<213> ORGANISM: Artificial
<220> FEATURE:
<223> OTHER INFORMATION: self-assembling peptides

<400> SEQUENCE: 71

Lys Leu Asn Leu Lys Leu Asn Leu Lys Leu Asn Leu Gly Tyr Ile Gly
1               5                   10                  15

Ser Arg

<210> SEQ ID NO 72
<211> LENGTH: 18
<212> TYPE: PRT
<213> ORGANISM: Artificial
<220> FEATURE:
<223> OTHER INFORMATION: self-assembling peptides

<400> SEQUENCE: 72

Lys Leu Asn Leu Lys Leu Asn Leu Lys Leu Asn Leu Gly Pro Asp Gly
1               5                   10                  15

Ser Arg
```

```
<210> SEQ ID NO 73
<211> LENGTH: 19
<212> TYPE: PRT
<213> ORGANISM: Artificial
<220> FEATURE:
<223> OTHER INFORMATION: self-assembling peptides

<400> SEQUENCE: 73

Lys Leu Asn Leu Lys Leu Asn Leu Lys Leu Asn Leu Gly Gly Val Gly
1               5                   10                  15

Val Ala Pro

<210> SEQ ID NO 74
<211> LENGTH: 20
<212> TYPE: PRT
<213> ORGANISM: Artificial
<220> FEATURE:
<223> OTHER INFORMATION: self-assembling peptides

<400> SEQUENCE: 74

Lys Leu Asn Leu Lys Leu Asn Leu Lys Leu Asn Leu Gly Pro Phe Ser
1               5                   10                  15

Ser Thr Lys Thr
            20

<210> SEQ ID NO 75
<211> LENGTH: 25
<212> TYPE: PRT
<213> ORGANISM: Artificial
<220> FEATURE:
<223> OTHER INFORMATION: self-assembling peptides

<400> SEQUENCE: 75

Lys Leu Asn Leu Lys Leu Asn Leu Lys Leu Asn Leu Gly Pro Arg Gly
1               5                   10                  15

Asp Ser Gly Tyr Arg Gly Asp Ser Gly
            20                  25

<210> SEQ ID NO 76
<211> LENGTH: 19
<212> TYPE: PRT
<213> ORGANISM: Artificial
<220> FEATURE:
<223> OTHER INFORMATION: self-assembling peptides

<400> SEQUENCE: 76

Lys Ile Gln Ile Lys Ile Gln Ile Lys Ile Gln Ile Lys Gly Tyr Ile
1               5                   10                  15

Gly Ser Arg

<210> SEQ ID NO 77
<211> LENGTH: 19
<212> TYPE: PRT
<213> ORGANISM: Artificial
<220> FEATURE:
<223> OTHER INFORMATION: self-assembling peptides

<400> SEQUENCE: 77

Lys Ile Gln Ile Lys Ile Gln Ile Lys Ile Gln Ile Lys Gly Pro Asp
1               5                   10                  15

Gly Ser Arg

<210> SEQ ID NO 78
```

```
<211> LENGTH: 20
<212> TYPE: PRT
<213> ORGANISM: Artificial
<220> FEATURE:
<223> OTHER INFORMATION: self-assembling peptides

<400> SEQUENCE: 78

Lys Ile Gln Ile Lys Ile Gln Ile Lys Ile Gln Ile Lys Gly Gly Val
1               5                   10                  15

Gly Val Ala Pro
            20

<210> SEQ ID NO 79
<211> LENGTH: 21
<212> TYPE: PRT
<213> ORGANISM: Artificial
<220> FEATURE:
<223> OTHER INFORMATION: self-assembling peptides

<400> SEQUENCE: 79

Lys Ile Gln Ile Lys Ile Gln Ile Lys Ile Gln Ile Lys Gly Pro Phe
1               5                   10                  15

Ser Ser Thr Lys Thr
            20

<210> SEQ ID NO 80
<211> LENGTH: 26
<212> TYPE: PRT
<213> ORGANISM: Artificial
<220> FEATURE:
<223> OTHER INFORMATION: self-assembling peptides

<400> SEQUENCE: 80

Lys Ile Gln Ile Lys Ile Gln Ile Lys Ile Gln Ile Lys Gly Pro Arg
1               5                   10                  15

Gly Asp Ser Gly Tyr Arg Gly Asp Ser Gly
            20                  25

<210> SEQ ID NO 81
<211> LENGTH: 18
<212> TYPE: PRT
<213> ORGANISM: Artificial
<220> FEATURE:
<223> OTHER INFORMATION: self-assembling peptides

<400> SEQUENCE: 81

Asn Leu Glu Leu Asn Leu Glu Leu Asn Leu Glu Leu Gly Tyr Ile Gly
1               5                   10                  15

Ser Arg

<210> SEQ ID NO 82
<211> LENGTH: 18
<212> TYPE: PRT
<213> ORGANISM: Artificial
<220> FEATURE:
<223> OTHER INFORMATION: self-assembling peptides

<400> SEQUENCE: 82

Asn Leu Glu Leu Asn Leu Glu Leu Asn Leu Glu Leu Gly Pro Asp Gly
1               5                   10                  15

Ser Arg

<210> SEQ ID NO 83
<211> LENGTH: 19
```

```
-continued

<212> TYPE: PRT
<213> ORGANISM: Artificial
<220> FEATURE:
<223> OTHER INFORMATION: self-assembling peptides

<400> SEQUENCE: 83

Asn Leu Glu Leu Asn Leu Glu Leu Asn Leu Glu Leu Gly Gly Val Gly
1               5                   10                  15

Val Ala Pro

<210> SEQ ID NO 84
<211> LENGTH: 20
<212> TYPE: PRT
<213> ORGANISM: Artificial
<220> FEATURE:
<223> OTHER INFORMATION: self-assembling peptides

<400> SEQUENCE: 84

Asn Leu Glu Leu Asn Leu Glu Leu Asn Leu Glu Leu Gly Pro Phe Ser
1               5                   10                  15

Ser Thr Lys Thr
            20

<210> SEQ ID NO 85
<211> LENGTH: 25
<212> TYPE: PRT
<213> ORGANISM: Artificial
<220> FEATURE:
<223> OTHER INFORMATION: self-assembling peptides

<400> SEQUENCE: 85

Asn Leu Glu Leu Asn Leu Glu Leu Asn Leu Glu Leu Gly Pro Arg Gly
1               5                   10                  15

Asp Ser Gly Tyr Arg Gly Asp Ser Gly
            20                  25

<210> SEQ ID NO 86
<211> LENGTH: 22
<212> TYPE: PRT
<213> ORGANISM: Artificial
<220> FEATURE:
<223> OTHER INFORMATION: self-assembling peptides

<400> SEQUENCE: 86

Arg Ala Asn Ala Arg Ala Asn Ala Arg Ala Asn Ala Arg Ala Asn Ala
1               5                   10                  15

Gly Tyr Ile Gly Ser Arg
            20

<210> SEQ ID NO 87
<211> LENGTH: 22
<212> TYPE: PRT
<213> ORGANISM: Artificial
<220> FEATURE:
<223> OTHER INFORMATION: self-assembling peptides

<400> SEQUENCE: 87

Arg Ala Asn Ala Arg Ala Asn Ala Arg Ala Asn Ala Arg Ala Asn Ala
1               5                   10                  15

Gly Pro Asp Gly Ser Arg
            20

<210> SEQ ID NO 88
<211> LENGTH: 23
```

```
<212> TYPE: PRT
<213> ORGANISM: Artificial
<220> FEATURE:
<223> OTHER INFORMATION: self-assembling peptides

<400> SEQUENCE: 88

Arg Ala Asn Ala Arg Ala Asn Ala Arg Ala Asn Ala Arg Ala Asn Ala
1               5                   10                  15

Gly Gly Val Gly Val Ala Pro
            20

<210> SEQ ID NO 89
<211> LENGTH: 24
<212> TYPE: PRT
<213> ORGANISM: Artificial
<220> FEATURE:
<223> OTHER INFORMATION: self-assembling peptides

<400> SEQUENCE: 89

Arg Ala Asn Ala Arg Ala Asn Ala Arg Ala Asn Ala Arg Ala Asn Ala
1               5                   10                  15

Gly Pro Phe Ser Ser Thr Lys Thr
            20

<210> SEQ ID NO 90
<211> LENGTH: 29
<212> TYPE: PRT
<213> ORGANISM: Artificial
<220> FEATURE:
<223> OTHER INFORMATION: self-assembling peptides

<400> SEQUENCE: 90

Arg Ala Asn Ala Arg Ala Asn Ala Arg Ala Asn Ala Arg Ala Asn Ala
1               5                   10                  15

Gly Pro Arg Gly Asp Ser Gly Tyr Arg Gly Asp Ser Gly
            20                  25

<210> SEQ ID NO 91
<211> LENGTH: 13
<212> TYPE: PRT
<213> ORGANISM: Artificial
<220> FEATURE:
<223> OTHER INFORMATION: self-assembling peptides

<400> SEQUENCE: 91

Ile Glu Ile Lys Ile Glu Ile Lys Ile Glu Ile Lys Ile
1               5                   10

<210> SEQ ID NO 92
<211> LENGTH: 13
<212> TYPE: PRT
<213> ORGANISM: Artificial
<220> FEATURE:
<223> OTHER INFORMATION: self-assembling peptides

<400> SEQUENCE: 92

Ile Glu Ile Lys Ile Glu Ile Lys Ile Glu Ile Lys Ile
1               5                   10

<210> SEQ ID NO 93
<211> LENGTH: 11
<212> TYPE: PRT
<213> ORGANISM: Artificial
<220> FEATURE:
<223> OTHER INFORMATION: self-assembling peptides
```

```
<400> SEQUENCE: 93

Lys Leu Asp Leu Lys Leu Asp Leu Lys Leu Asp
1               5                   10

<210> SEQ ID NO 94
<211> LENGTH: 13
<212> TYPE: PRT
<213> ORGANISM: Artificial
<220> FEATURE:
<223> OTHER INFORMATION: self-assembling peptides

<400> SEQUENCE: 94

Ile Glu Ile Thr Ile Glu Ile Thr Ile Glu Ile Thr Ile
1               5                   10

<210> SEQ ID NO 95
<211> LENGTH: 13
<212> TYPE: PRT
<213> ORGANISM: Artificial
<220> FEATURE:
<223> OTHER INFORMATION: self-assembling peptides

<400> SEQUENCE: 95

Ile Thr Ile Lys Ile Thr Ile Lys Ile Thr Ile Lys Ile
1               5                   10

<210> SEQ ID NO 96
<211> LENGTH: 12
<212> TYPE: PRT
<213> ORGANISM: Artificial
<220> FEATURE:
<223> OTHER INFORMATION: self-assembling peptides

<400> SEQUENCE: 96

Lys Ile Gln Ile Lys Ile Gln Ile Lys Ile Gln Ile
1               5                   10

<210> SEQ ID NO 97
<211> LENGTH: 13
<212> TYPE: PRT
<213> ORGANISM: Artificial
<220> FEATURE:
<223> OTHER INFORMATION: self-assembling peptides

<400> SEQUENCE: 97

Ile Glu Ile Thr Ile Glu Ile Thr Ile Glu Ile Thr Ile
1               5                   10

<210> SEQ ID NO 98
<211> LENGTH: 13
<212> TYPE: PRT
<213> ORGANISM: Artificial
<220> FEATURE:
<223> OTHER INFORMATION: self-assembling peptides

<400> SEQUENCE: 98

Ile Thr Ile Lys Ile Thr Ile Lys Ile Thr Ile Lys Ile
1               5                   10

<210> SEQ ID NO 99
<211> LENGTH: 12
<212> TYPE: PRT
<213> ORGANISM: Artificial
<220> FEATURE:
<223> OTHER INFORMATION: self-assembling peptides
```

```
<400> SEQUENCE: 99

Lys Ile Gln Ile Lys Ile Gln Ile Lys Ile Gln Ile
1               5                   10
```